(12) United States Patent
Theodoridis et al.

(10) Patent No.: US 6,753,429 B2
(45) Date of Patent: Jun. 22, 2004

(54) 1,4-DISUBSTITUTED BENZENES AS INSECTICIDES

(75) Inventors: George Theodoridis, Princeton, NJ (US); Edward Barron, Trenton, NJ (US); Daniel H. Cohen, Princeton, NJ (US); Ellen M. Crawford, Jackson, NJ (US); Thomas G. Cullen, Andover, MA (US); Hongyan Qi, Plainsboro, NJ (US); Elizabeth Rowley, Kendall Park, NJ (US); Syed F. Ali, Yardville, NJ (US); Walter H. Yeager, Yardley, PA (US); Christina B. Duggan, Plainsboro, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 09/941,812

(22) Filed: Aug. 29, 2001

(65) Prior Publication Data

US 2002/0183342 A1 Dec. 5, 2002

Related U.S. Application Data

(60) Provisional application No. 60/229,701, filed on Sep. 1, 2000, and provisional application No. 60/277,203, filed on Mar. 20, 2001.

(51) Int. Cl.$^7$ .................... C07D 241/04; C07D 211/06; C07D 317/44; C07C 291/00; C07C 215/00
(52) U.S. Cl. ................ 544/395; 546/206; 549/443; 564/299; 564/308; 564/341; 564/347; 514/277; 514/278; 514/649; 514/657
(58) Field of Search ................. 546/206; 549/443; 564/299, 308, 341, 347

(56) References Cited

U.S. PATENT DOCUMENTS

| | | |
|---|---|---|
| 3,987,102 A | 10/1976 | Karrer |
| 4,016,195 A | 4/1977 | Pintschovius et al. |
| 4,145,439 A | 3/1979 | Schultze et al. |
| 4,183,949 A | 1/1980 | Hamprecht et al. |
| 4,822,775 A * | 4/1989 | Hansen, Jr. et al. |
| 4,837,217 A | 6/1989 | Ogura et al. |
| 4,859,706 A | 8/1989 | Buerstinghaus et al. |
| 5,569,664 A | 10/1996 | Silverman et al. |

FOREIGN PATENT DOCUMENTS

| | | |
|---|---|---|
| DE | 234 795 | 5/1911 |
| DE | 40 10 325 | 10/1990 |
| EP | 0 331 529 | 9/1989 |

OTHER PUBLICATIONS

Aldrich Chemical Company, Inc., 1994, Milwaukee, WI, p. 1129.*
Arzneimittel Forschung Drug Research, Synthesis of Several Phenoxymethylphenyl Derivatives with Local Anesthetic Activity, 1979, 29(4), pp. 591–594. English Abstract.*

International Search Report for PCT/US01/26962 dated Feb. 4, 2003.
XP–002213708, Belstein Registry No. 3325434 (1990) (abstract).
XP–002226603, Belstein Registry No. 2520198 (1989) (abstract).
XP–002226604, Belstein Registry No. 2527029 (1989) (abstract).
XP–002226605, Belstein Registry No. 2558639 (1989) (abstract).
XP–002226606, Belstein Registry No. 2944661 (1989) (abstract).
XP–002226607, Belstein Registry No. 6718497 (1994) (abstract).
XP–002226608, Belstein Registry No. 2103329 (1989) (abstract).
XP–002226609, Belstein Registry No. 2831482 (1989) (abstract).
XP–002226610, Belstein Registry No. 3325434 (1990) (abstract).
XP–002226611, Belstein Registry No. 5433887 (1993) (abstract).
XP–002213707, Belstein Registry Number 2452671 (1989) (abstract).
XP–002226612, Belstein Registry Number 2619465 (1989) (abstract).
XP–002226613, Belstein Registry Number 4442848 (1991) (abstract).

* cited by examiner

Primary Examiner—Porfirio Nazario-Gonzalez
Assistant Examiner—Paul A. Zucker
(74) Attorney, Agent, or Firm—FMC Corporation

(57) ABSTRACT

Compounds of formula I:

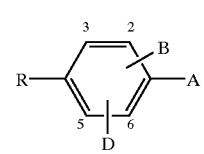

wherein A, B, D, and R are as defined herein and their agriculturally acceptable salts are disclosed as effective insecticides. In addition, compositions comprising an insecticidally effective amount of a compound of Formula I in admixture with at least one agriculturally acceptable extender or adjuvant and methods of controlling insects comprising applying said compositions to locus on crops where control is desired are disclosed. It is emphasized that this abstract is provided to comply with the rules requiring an abstract that will allow a searcher or other reader to quickly ascertain the subject matter of the technical disclosure. It is submitted with the understanding that it will not be used to interpret or limit the scope or meaning of the claims (see 37 C.F.R. 1.72(b)).

19 Claims, No Drawings

1,4-DISUBSTITUTED BENZENES AS INSECTICIDES

This is a nonprovisional of Application Nos. 60/229,701 and 60/277,203 filed on Sep. 1, 2000 and Mar. 20, 2001, respectively.

FIELD OF THE INVENTION

The present invention relates to methods for controlling insects. In particular, it relates to control by the application of certain novel substituted benzenes.

BACKGROUND OF THE INVENTION

The present invention relates to methods for controlling insects. In particular, it relates to control by the application of certain novel substituted benzenes. More particularly, it pertains to 1,4-disubstituted benzene compounds and compositions containing the same which are useful for controlling insects in agricultural crops. Even more particularly, this invention relates 1,4-disubstituted benzene compounds and compositions and their uses as insecticides against a variety of insects, including larvae, such as tobacco budworm.

SUMMARY OF THE INVENTION

It has now been found that certain substituted benzenes, particularly 1,4-disubstituted benzenes, and their agriculturally acceptable salts, are effective as insecticides. These benzenes may be represented by the following formula I:

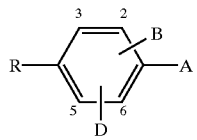

in which:

A is hydrogen; aryl; alkylheterocyclyl; alkenylaminopolycyclyl; alkenylaminoheterocyclyl; alkylaminopolycyclyl; carbonylaminopolycyclyl; and Formula III, where Formula III is

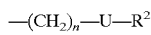   III where n is 0 or 1;

U is —CH$_2$—, —O—CH$_2$—, oxygen, sulfur, sulfonyl, alkyl, oxyalkyloxy, alkenylamino, cabonylamino and —NR$^5$, where R$^5$ is hydrogen, hydroxy, alkyl, haloalkyl, sulfonylalkyl, cabonylamino, and carbonylalkyl;

R$^2$ is aryl; alkylpolycyclyl; heterocyclyl; polycyclyl; 1-R$^3$; 1-R$^4$; and 2-R$^4$, where:

R$^3$ is

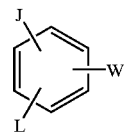

where

J, L, and W are independently hydrogen, halogen, cyano, nitro, amino, carboxyl, alkyl, haloalkyl, alkenyl, alkoxy, haloalkoxy, aminoalkoxy, nitrilyl, carbonyl, alkylcarbonyl, haloalkylcarbonyl, alkoxycarbonyl, haloalkoxycarbonyl, aryl, aryloxy, and heterocyclyl;

R$^4$ is

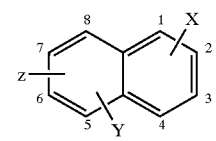

where

X, Y, and Z are independently hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, aryloxy, and heterocyclyl;

B and D are independently hydrogen, halogen, alkyl, haloalkyl, alkoxy, haloalkoxy, alkoxyaminoalkyl, 2-(Formula III), 3-(Formula III), 5-(Formula III), and 6-(Formula III), where Formula III, n, U, R$^2$, R$^3$, R$^4$, R$^5$, J, L, W, X, Y, and Z are as defined above;

R is —T—(CH$_2$)$_m$—R$^1$, —N(R$^6$)(R$^7$) or heterocyclyl;

T is —CH$_2$—, carbonyl, oxygen, nitrogen, and sulfur;

m is 0, 1, 2, 3, or 4;

R$^1$ is —N(R$^8$)(R$^9$); alkyl; aryl; —C(O)N(R$^{12}$)(R$^{13}$); oxyalkyl; haloalkyl; heterocyclyl; cycloalkyl; —N(O)(R$^{14}$)(R$^{15}$); —P(O)(R$^{14}$)(R$^{15}$); —P(S)(R$^{14}$)(R$^{15}$); alkylamino, where the cyclohexyl, aryl and heterocyclyl moieties may be optionally substituted with halogen, hydroxy, alkyl, haloalkyl, alkoxy, haloalkoxy, alkoxycarbonyl, aryl, arylcarbonyl, alkylamino; where R$^6$, R$^7$, R$^8$, R$^9$, R$^{12}$, R$^{13}$, R$^{14}$ and R$^{15}$ are independently hydrogen, alkyl, alkoxy, alkylthio, acetyl, alkoxycarbonyl, alkoxyalkyl, aminoalkyl, carbonylamino, and —(CH$_2$)$_p$—N(R$^{16}$)(R$^{17}$), where p is 1 or 2; and R$^{16}$ and R$^{17}$ are independently hydrogen, alkyl, alkoxy, alkoxyalkyl, and aminoalkyl.

The present invention is also directed to a composition containing an insecticidally effective amount of a compound of Formula I in admixture with at least one agriculturally acceptable extender or adjuvant, wherein A, B, D, and R are as defined above.

In addition, the present invention relates to a method of controlling insects that comprises applying to locus on crops, such as cotton, vegetables, fruits, where control is desired an insecticidally effective amount of a the above composition.

DETAILED DESCRIPTION OF THE INVENTION

In one aspect of the present invention, certain substituted benzenes, particularly 1,4-disubstituted benzenes, and the agriculturally acceptable salts thereof, have now been found to be effective as insecticides. These benzenes may be represented by the following formula I:

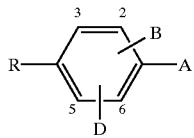

I in which:

A is selected from the group consisting of hydrogen; aryl; alkylheterocyclyl; alkenylaminopolycyclyl; alkenylaminoheterocyclyl; alkylaminopolycyclyl; carbonylaminopolycyclyl; where the aryl, heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and Formula III, where Formula III is

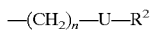 III wherein n is 0 or 1;

U is selected from the group consisting of —CH$_2$—, —O—CH$_2$—, oxygen, sulfur, sulfonyl, alkyl, oxyalkyloxy, alkenylamino, cabonylamino and —NR$^5$, where R$^5$ is selected from the group consisting of hydrogen, hydroxy, alkyl, haloalkyl, sulfonylalkyl, cabonylamino, and carbonylalkyl;

R$^2$ is selected from aryl; alkylpolycyclyl; heterocyclyl; polycyclyl; where the aryl, heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; 1-R$^3$; 1-R$^4$; and 2-R$^4$, wherein:

R$^3$ is

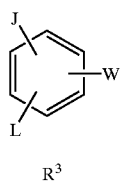

where

J, L, and W are independently selected from the group consisting of hydrogen, halogen, cyano, nitro, amino, carboxyl, alkyl, haloalkyl, alkenyl, alkoxy, haloalkoxy, aminoalkoxy, nitrilyl, carbonyl, alkylcarbonyl, haloalkylcarbonyl, alkoxycarbonyl, haloalkoxycarbonyl, aryl, aryloxy, and heterocyclyl, where the aryl and heterocyclyl moieties may be optionally substituted with halogen, alkyl, haloalkyl, alkoxy, or haloalkoxy;

R$^4$ is

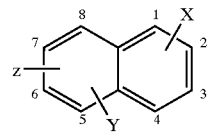

where

X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, aryloxy, and heterocyclyl, where the phenyl, aryl, and heterocyclyl moieties may be optionally substituted with halogen, haloalkyl, haloalkyl, alkoxy, or haloalkoxy;

B and D are independently selected from hydrogen, halogen, alkyl, haloalkyl, alkoxy, haloalkoxy, alkoxyaminoalkyl, 2-(Formula III), 3-(Formula III), 5-(Formula III), and 6-(Formula III), wherein Formula III, n, U, R$^2$, R$^3$, R$^4$, R$^5$, J, L, W, X, Y, and Z are as defined above;

R is —T—(CH$_2$)$_m$—R$^1$, —N(R$^6$)(R$^7$) or heterocyclyl, where the heterocyclyl moiety may be optionally substituted with halogen, hydroxy, alkyl, haloalkyl, alkoxy, haloalkoxy, alkoxycarbonyl, aryl, alkylaza, arylcarbonyl, benzyl, allyl, propargyl, alkylamino; where the aryl moiety may be optionally substituted with halogen, hydroxy, alkyl, haloalkyl, alkoxy, haloalkoxy, alkoxycarbonyl, aryl, arylcarbonyl T is selected from the group consisting of —CH$_2$—, carbonyl, oxygen, nitrogen, and sulfur;

m is 0, 1, 2, 3, or 4;

R$^1$ is selected from the group consisting of —N(R$^8$)(R$^9$); alkyl; aryl; —C(O)N(R$^{12}$)(R$^{13}$); oxyalkyl; haloalkyl; heterocyclyl; cycloalkyl; —N(O)(R$^{14}$)(R$^{15}$); —P(O)(R$^{14}$)(R$^{15}$); —P(S)(R$^{14}$)(R$^{15}$); alkylamino, where the cycloalkyl, aryl and heterocyclyl moieties may be optionally substituted with halogen, hydroxy, alkyl, haloalkyl, alkoxy, haloalkoxy, alkoxycarbonyl, aryl, arylcarbonyl, alkylamino; where R$^6$, R$^7$, R$^8$, R$^9$, R$^{12}$, R$^{13}$, R$^{14}$ and R$^{15}$ are independently selected from the group consisting of hydrogen, alkyl, alkoxy, alkylthio, acetyl, alkoxycarbonyl, alkoxyalkyl, aminoalkyl, carbonylamino, and —(CH$_2$)$_p$—N(R$^{16}$)(R$^{17}$), where p is 1 or 2;

R$^{16}$ and R$^{17}$ are independently selected from the group consisting of hydrogen, alkyl, alkoxy, alkoxyalkyl, and aminoalkyl.

Agriculturally acceptable salts of the 1,4-disubstituted benzenes include, but are not limited to, for example, the salts of hydrochloric acid, sulfonic acid, ethanesulfonic acid, trifluoroacetic acid, methylbenzenesulfonic acid, phosphoric acid, gluconic, acid, and pamoic acid.

Some preferred compounds are those in which

A is selected from the group consisting of hydrogen; alkylaminopolycyclyl; carbonylaminopolycyclyl; where the polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkyl-carbonyl, alkoxycarbonyl, haloalkoxycarbonyl, or aryl; and Formula III, where Formula III is

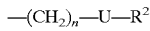  III wherein n is 0 or 1;

U is selected from the group consisting of —CH$_2$—, oxygen, and —NR$^5$, where R$^5$ is selected from the group consisting of hydrogen, hydroxy, alkyl, sulfonylalkyl, cabonylamino, and carbonylalkyl;

R$^2$ is selected from aryl, alkylpolycyclyl; heterocyclyl; polycyclyl; where the aryl, heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and 1-R$^3$, wherein R$^3$ is:

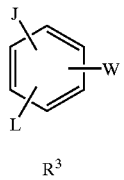

where

J, L, and W are independently selected from the group consisting of hydrogen, halogen, cyano, nitro, amino, carboxyl, alkyl, haloalkyl, alkenyl, alkoxy, haloalkoxy, nitrilyl, carbonyl, alkylcarbonyl, haloalkylcarbonyl, alkoxycarbonyl, haloalkoxycarbonyl, aryl, and aryloxy, where the aryl moieties may be optionally substituted with halogen, alkyl, haloalkyl, alkoxy, or haloalkoxy;

B and D are independently selected from hydrogen, halogen, alkyl, haloalkyl, alkoxy, haloalkoxy, alkoxyaminoalkyl;

R is —T—(CH$_2$)$_m$—R$^1$, where

T is selected from the group consisting of —CH$_2$—, oxygen, nitrogen, and sulfur;

m is 1, 2, 3, or 4;

R$^1$ is —N(R$^8$)(R$^9$), where

R$^8$ and R$^9$ are independently selected from the group consisting of hydrogen, alkyl, alkoxy, acetyl, alkoxycarbonyl, alkoxyalkyl, aminoalkyl, carbonylamino, and —(CH$_2$)$_p$—N(R$^{16}$)(R$^{17}$), where p is 1 or 2;

R$^{16}$ and R$^{17}$ are independently selected from the group consisting of hydrogen, alkyl, alkoxy, alkoxyalkyl, and aminoalkyl;

and the corresponding agriculturally acceptable salts thereof.

Some particularly preferred compounds are those in which

A is hydrogen or Formula III, where Formula III is

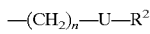  III wherein n is 0 or 1;

U is selected from the group consisting of —CH$_2$—, oxygen, and —NR$^5$, where R$^5$ is selected from the group consisting of hydrogen, hydroxy, alkyl, sulfonylalkyl, cabonylamino, and carbonylalkyl;

R$^2$ is selected from heterocyclyl; polycyclyl; where the heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkyl-carbonyl, alkoxycarbonyl, haloalkoxycarbonyl, or aryl; and 1-R$^3$, wherein R$^3$ is:

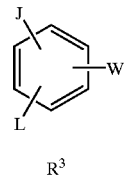

where

J, L, and W are independently selected from the group consisting of hydrogen, halogen, cyano, nitro, ammo, carboxyl, alkyl, haloalkyl, alkenyl, alkoxy, haloalkoxy, nitrilyl, carbonyl, alkylcarbonyl, haloalkylcarbonyl, alkoxycarbonyl, haloalkoxycarbonyl, aryl, and aryloxy, where the aryl moieties may be optionally substituted with halogen, alkyl, haloalkyl, alkoxy, or haloalkoxy;

B and D are independently selected from hydrogen, halogen, alkyl, haloalkyl, alkoxy, haloalkoxy, alkoxyamninoalkyl;

T is oxygen or nitrogen m is 2, 3, or 4;

R$^1$ is —N(R$^8$)(R$^9$), where

R$^8$ and R$^9$ are independently selected from the group consisting of hydrogen, alkyl, alkoxy, acetyl, alkoxycarbonyl, alkoxyalkyl, aminoalkyl, carbonylamino, and —(CH$_2$)$_p$—N(R$^{16}$)(R$^{17}$), where p is 1 or 2;

R$^{16}$ and R$^{17}$ are independently selected from the group consisting of hydrogen, alkyl, alkoxy, alkoxyalkyl, and aminoalkyl.

Some more particularly preferred compounds are those in which A is Formula III, where Formula III is

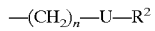  III wherein n is 1;

U is oxygen or —NR$^5$, where R$^5$ is selected from the group consisting of hydrogen, hydroxy, alkyl, sulfonylalkyl, cabonylamino, and carbonylalkyl;

R$^2$ is 1-R$^3$, wherein R$^3$ is:

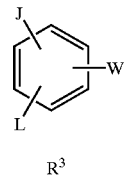

where

J, L, and W are independently selected from the group consisting of hydrogen, halogen, cyano, nitro, amino, carboxyl, alkyl, haloalkyl, alkenyl, alkoxy, haloalkoxy, nitrilyl, carbonyl, alkylcarbonyl, haloalkylcarbonyl, alkoxycarbonyl, haloalkoxycarbonyl, aryl, and aryloxy, where the aryl moieties may be optionally substituted with halogen, alkyl, haloalkyl, alkoxy, or haloalkoxy;

B and D are independently selected from hydrogen, halogen, alkyl, haloalkyl, alkoxy, haloalkoxy, alkoxyaminoalkyl;

T is oxygen or nitrogen m is 2;

$R^1$ is —$N(R^8)(R^9)$, where $R^8$ and $R^9$ are independently selected from the group consisting of hydrogen, alkyl, alkoxy, acetyl, alkoxycarbonyl, alkoxyalkyl, aminoalkyl, carbonylamino, and —$(CH_2)_p$—$N(R^{16})(R^{17})$, where p is 1 or 2;

$R^{16}$ and $R^{17}$ are independently selected from the group consisting of hydrogen, alkyl, alkoxy, alkoxyalkyl, and aminoalkyl;

Some yet even more particularly preferred compounds are those in which

U is oxygen or —$NR^5$, where $R^5$ is selected from the group consisting of hydrogen, hydroxy, alkyl, sulfonylalkyl, cabonylamino, and carbonylalkyl;

$R^2$ is 1-$R^3$, wherein $R^3$ is:

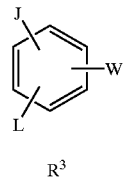

where

J, L, and W are independently selected from the group consisting of hydrogen, halogen, cyano, nitro, amino, carboxyl, alkyl, haloalkyl, alkenyl, alkoxy, haloalkoxy, nitrilyl, carbonyl, alkylcarbonyl, haloalkylcarbonyl, alkoxycarbonyl, haloalkoxycarbonyl, aryl, and aryloxy, where the aryl moieties may be optionally substituted with halogen, alkyl, haloalkyl, alkoxy, or haloalkoxy;

B and D are independently selected from hydrogen, halogen, and alkoxy;

T is oxygen;

$R^1$ is —$N(R^8)(R^9)$; where $R^8$ and $R^9$ are independently selected from the group consisting of hydrogen, alkyl, alkoxy, acetyl, alkoxycarbonyl, alkoxyalkyl, aminoalkyl, carbonylamino, and —$(CH_2)_p$—$N(R^{16})(R^{17})$, where p is 1 or 2;

$R^{16}$ and $R^{17}$ are independently selected from the group consisting of hydrogen, alkyl, alkoxy, alkoxyalkyl, and aminoalkyl;

Some still yet even more particularly preferred compounds are those in which U is oxygen or —$NR^5$, where $R^5$ is hydrogen; $R^2$ is 1-$R^3$, wherein $R^3$ is:

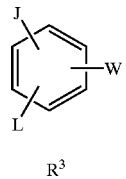

where

J, L, and W are independently selected from the group consisting of hydrogen, halogen, cyano, nitro, amino, carboxyl, alkyl, haloalkyl, alkenyl, alkoxy, haloalkoxy, nitrilyl, carbonyl, alkylcarbonyl, haloalkylcarbonyl, alkoxycarbonyl, haloalkoxycarbonyl, aryl, and aryloxy, where the aryl moieties may be optionally substituted with halogen, alkyl, haloalkyl, alkoxy, or haloalkoxy;

B and D are hydrogen;

$R^1$ is —$N(R^8)(R^9)$; where $R^8$ and $R^9$ are alkyl.

In another aspect, the present invention is directed to certain novel 1,4-disubstituted benzenes per se and agriculturally acceptable salts thereof falling within the scope of formula I above. These compounds include, for example, the following novel 1,4-disubstituted benzenes:

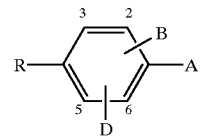

I in which:

A is Formula III, where Formula III is $$—(CH_2)_n—U—R^2 \qquad III$$

wherein n is 1;

U is oxygen;

$R^2$ is 1-$R^3$; wherein:

$R^3$ is

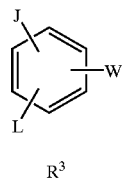

where

J is 2-chloro or 2-fluoro, L is 3-chloro or 5-fluoro, and W is hydrogen or 4-chloro, B and D are hydrogen;

R is —T—$(CH_2)_m$—$R^1$, where

T is oxygen;

m is 2;

$R^1$ is —$N(R^8)(R^9)$, where $R^8$ and $R^9$ are ethyl.

Additional preferred compounds are those in which A is selected from the group consisting of hydrogen; alkylaminopolycyclyl; and carbonylaminopolycyclyl; where the polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and Formula III, where Formula III is —(CH$_2$)$_n$—U—R$^2$      III wherein
n is 0 or 1;
U is selected from the group consisting of —CH$_2$—, oxygen, alkyl, oxyalkyloxy, alkenylamino, cabonylamino and —NR$^5$, where R$^5$ is selected from the group consisting of hydrogen, hydroxy, alkyl, sulfonylalkyl, cabonylamino, and carbonylalkyl;
R$^2$ is selected from aryl; alkylpolycyclyl; heterocyclyl; polycyclyl; where the aryl, heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and 1-R$^4$, wherein R$^4$ is

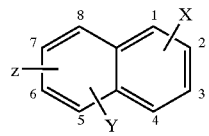

R$^4$ where
X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;
B and D are independently selected from hydrogen, halogen, alkyl, haloalkyl, alkoxy, haloalkoxy, and alkoxyaminoalkyl;
R is —T—(CH$_2$)$_m$—R$^1$ or heterocyclyl; where
the heterocyclyl moiety may be optionally substituted with halogen, alkyl, haloalkyl, alkoxy, haloalkoxy, alkoxycarbonyl, aryl, arylcarbonyl, benzyl, allyl, propargyl;
T is selected from the group consisting of —CH$_2$—, oxygen, nitrogen, and sulfur;
m is 1, 2, 3, or 4;
R$^1$ is selected from the group consisting of —N(R$^8$)(R$^9$); alkyl; aryl; —C(O)N(R$^{12}$)(R$^{13}$); oxyalkyl; haloalkyl; heterocyclyl; cycloalkyl; and —N(O)(R$^{14}$)(R$^{15}$), where the aryl and heterocyclyl moieties may be optionally substituted with halogen, alkyl, haloalkyl, alkoxy, haloalkoxy, alkoxycarbonyl, aryl, arylcarbonyl; where
R$^8$, R$^9$, R$^{12}$, R$^{13}$, R$^{14}$ and R$^{15}$ are independently selected from the group consisting of hydrogen, alkyl, alkoxy, acetyl, alkoxycarbonyl, alkoxyalkyl, aminoalkyl, carbonylamino, and —(CH$_2$)$_p$—N(R$^{16}$)(R$^{17}$), where
p is 1 or 2;
R$^{16}$ and R$^{17}$ are independently selected from the group consisting of hydrogen, alkyl, alkoxy, alkoxyalkyl, and aminoalkyl;

and the corresponding agriculturally acceptable salts thereof.

Additional particularly preferred compounds are those in which A is hydrogen or Formula III, where Formula III is —(CH$_2$)$_n$—U—R$^2$      III wherein
n is 0 or 1;
U is selected from the group consisting of —CH$_2$—, oxygen, and —NR$^5$, where R$^5$ is selected from the group consisting of hydrogen, hydroxy, alkyl, sulfonylalkyl, cabonylamino, and carbonylalkyl;
R$^2$ is selected from alkylpolycyclyl; heterocyclyl; polycyclyl; where the heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and R$^4$, wherein R$^4$ is

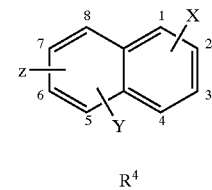

R$^4$ where
X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;
B and D are independently selected from hydrogen, halogen, alkyl, haloalkyl, alkoxy, haloalkoxy, and alkoxyaminoalkyl;
R is —T—(CH$_2$)$_m$—R$^1$ or heterocyclyl; where
the heterocyclyl moiety may be optionally substituted with halogen, alkyl, haloalkyl, alkoxy, haloalkoxy, alkoxycarbonyl, aryl, arylcarbonyl, benzyl, allyl, propargyl;
T is selected from the group consisting of oxygen, nitrogen, and sulfur;
m is 1, 2, 3, or 4;
R$^1$ is selected from the group consisting of —N(R$^8$)(R$^9$); alkyl; aryl; —C(O)N(R$^{12}$)(R$^{13}$); oxyalkyl; haloalkyl; heterocyclyl; cycloalkyl; and —N(O)(R$^{14}$)(R$^{15}$), where the aryl and heterocyclyl moieties may be optionally substituted with halogen, alkyl, haloalkyl, alkoxy, haloalkoxy, alkoxycarbonyl, aryl, arylcarbonyl; where
R$^8$, R$^9$, R$^{10}$, R$^{13}$, R$^{14}$ and R$^{15}$ are independently selected from the group consisting of hydrogen, alkyl, alkoxy, acetyl, alkoxycarbonyl, alkoxyalkyl, aminoalkyl, carbonylamino, and —(CH$_2$)$_p$—N(R$^{16}$)(R$^{17}$), where
p is 1 or 2;
R$^{16}$ and R$^{17}$ are independently selected from the group consisting of hydrogen, alkyl, alkoxy, alkoxyalkyl, and aminoalkyl;
and the corresponding agriculturally acceptable salts thereof.

Additional more particularly preferred compounds are those in which A is Formula III, where Formula III is —(CH$_2$)$_n$—U—R$^2$   III wherein n is 1;

U is oxygen or —NR$^5$, where R$^5$ is selected from the group consisting of hydrogen, hydroxy, alkyl, sulfonylalkyl, cabonylamino, and carbonylalkyl;

R$^2$ is 1-R$^4$, wherein R$^4$ is

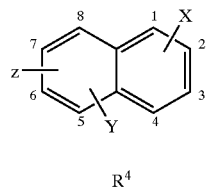

where

X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

B and D are independently selected from hydrogen, halogen, alkyl, haloalkyl, alkoxy, haloalkoxy, and alkoxyaminoalkyl;

R is —T—(CH$_2$)$_m$—R$^1$ or heterocyclyl; where the heterocyclyl moiety may be optionally substituted with halogen, alkyl, haloalkyl, alkoxy, haloalkoxy, alkoxycarbonyl, aryl, arylcarbonyl, benzyl, allyl, propargyl;

T is oxygen or nitrogen;

m is 1, 2, 3, or 4;

R$^1$ is selected from the group consisting of —N(R$^8$)(R$^9$); alkyl; aryl; —C(O)N(R$^{12}$)(R$^{13}$); oxyalkyl; haloalkyl; heterocyclyl; cycloalkyl; and —N(O)(R$^{14}$)(R$^{15}$), where the aryl and heterocyclyl moieties may be optionally substituted with halogen, alkyl, haloalkyl, alkoxy, haloalkoxy, alkoxycarbonyl, aryl, arylcarbonyl; where R$^8$, R$^9$, R$^{12}$, R$^{13}$, R$^{14}$ and R$^{15}$ are independently selected from the group consisting of hydrogen, alkyl, alkoxy, acetyl, alkoxycarbonyl, alkoxyalkyl, aminoalkyl, carbonylamino, and —(CH$_2$)$_p$—N(R$^{16}$)(R$^{17}$), where p is 1 or 2;

R$^{16}$ and R$^{17}$ are independently selected from the group consisting of hydrogen, alkyl, alkoxy, alkoxyalkyl, and aminoalkyl;

and the corresponding agriculturally acceptable salts thereof.

Additional yet even more particularly preferred compounds are those in which A is Formula III, where Formula III is —(CH$_2$)$_n$—U—R$^2$   III wherein U is oxygen or —NR$^5$, where R$^5$ is hydrogen;

R$^2$ is 1-R$^4$, wherein R$^4$ is

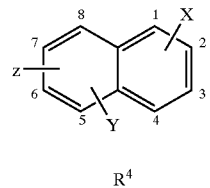

where

X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

B and D are independently selected from hydrogen, halogen, alkyl, haloalkyl, alkoxy, haloalkoxy, and alkoxyaminoalkyl;

R is —T—(CH$_2$)$_m$—R$^1$ or heterocyclyl; where the heterocyclyl moiety may be optionally substituted with halogen, alkyl, haloalkyl, alkoxy, haloalkoxy, alkoxycarbonyl, aryl, arylcarbonyl, benzyl, allyl, propargyl;

T is oxygen or nitrogen;

m is 2;

R$^1$ is —N(R$^8$)(R$^9$) or —N(O)(R$^{14}$)(R$^{15}$), where R$^8$, R$^9$, R$^{14}$, and R$^{15}$ are independently selected from the group consisting of hydrogen, alkyl, alkoxy, acetyl, alkoxycarbonyl, alkoxyalkyl, aminoalkyl, carbonylamino, and —(CH$_2$)$_p$—N(R$^{16}$)(R$^{17}$), where p is 1 or 2;

R$^{16}$ and R$^{17}$ are independently selected from the group consisting of hydrogen, alkyl, alkoxy, alkoxyalkyl, and aminoalkyl;

and the corresponding agriculturally acceptable salts thereof.

Additional still yet even more particularly preferred compounds are those in which A is Formula III, where Formula III is —(CH$_2$)$_n$—U—R$^2$   III wherein U is O or —NR$^5$, where R$^5$ is hydrogen;

R$^2$ is selected from 1-R$^4$, wherein R$^4$ is

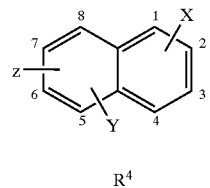

where

X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

B and D are hydrogen;

the heterocyclyl is a piperazinyl moiety, where the the piperazinyl moiety may be optionally substituted with halogen, alkyl, haloalkyl, alkoxy, haloalkoxy, alkoxycarbonyl, aryl, arylcarbonyl, benzyl, allyl, propargyl;

T is oxygen;

$R^1$ is —$N(R^8)(R^9)$ or —$N(O)(R^{14})(R^{15})$, where $R^8$, $R^9$, $R^{14}$, and $R^{15}$ are independently selected from the group consisting of hydrogen, alkyl, alkoxy, acetyl, alkoxycarbonyl, alkoxyalkyl, aminoalkyl, and carbonylamino;

and the corresponding agriculturally acceptable salts thereof.

Further preferred compounds are those in which

A is Formula III, where Formula III is

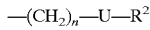  III wherein

U is O;

$R^2$ is selected from 1-$R^4$, wherein $R^4$ is

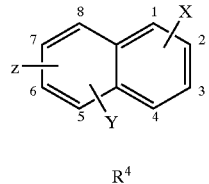

where

X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

$R^1$ is —$N(R^8)(R^9)$ or —$N(O)(R^{14})(R^{15})$, where $R^8$, $R^9$, $R^{14}$ and $R^{15}$ are alkyl;

and the corresponding agriculturally acceptable salts thereof.

In addition to those compounds set forth above, the present invention is also directed to certain novel 1,4-disubstituted benzenes per se and agriculturally acceptable salts thereof falling within the scope of formula I above. These compounds include, for example, the following novel 1,4-disubstituted benzenes:

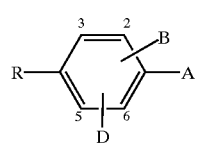  I in which:

A is Formula III, where Formula III is

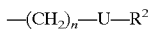  III wherein n is 1;

U is oxygen;

$R^2$ is 1-$R^4$; wherein:

$R^4$ is

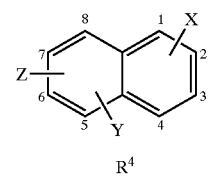

where

X is 4-chloro or 5-chloro, Y is 6-chloro or 6-bromo, and Z is hydrogen;

B and D are hydrogen;

R is —T—$(CH_2)_m$—$R^1$ or a piperazinyl moiety; where the piperazinyl moiety is substituted with 4-ethyl;

T is oxygen;

m is 2;

$R^1$ is —$N(R^8)(R^9)$ or —$N(O)(R^{14})(R^{15})$, where $R^8$, $R^9$, $R^{14}$ and $R^{15}$ are ethyl;

and the agriculturally acceptable salts thereof, preferably the hydrochloride salts.

In another aspect, the present invention is directed to a composition containing an insecticidally effective amount of a compound of Formula I, including, without limitation, those compounds disclosed above as being preferred, particularly preferred, and per se novel, in admixture with at least one agriculturally acceptable extender or adjuvant, wherein A, B, D, and R are as defined above.

In another aspect, the present invention relates to a method of controlling insects that comprises applying to locus on crops, such as cotton, vegetables, fruits, where control is desired an insecticidally effective amount of the above compositions.

Certain intermediates or the present invention are novel. These include compounds of formula XII:

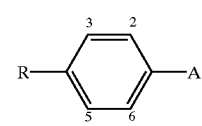  XII wherein:

A is —$(CH_2)_n$—U—$R^2$ wherein n is 0 or 1;

U is —C(O)—, —$CH_2$—, oxygen, or —$NR^5$, where $R^5$ is selected from the group consisting of hydrogen, hydroxy, alkyl, sulfonylalkyl, cabonylamino, and carbonylalkyl;

$R^2$ is selected from hydrogen, halo, hydroxy, and 1-$R^4$, wherein:

$R^4$ is

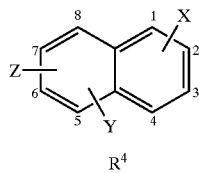

where

X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

R is —T—$(CH_2)_m$—$R^1$, where

T is selected from the group consisting of oxygen, nitrogen, and sulfur;

m is 0, 1, 2, 3, or 4;

$R^1$ is hydrogen, halo, alkyl, or —$N(R^8)(R^9)$; where $R^8$ and $R^9$ are independently selected from the group consisting of hydrogen, alkyl, alkoxy, acetyl, alkoxycarbonyl, alkoxyalkyl, aminoalkyl, carbonylamino, and —$(CH_2)_p$—$N(R^{16})(R^{17})$, where p is 1 or 2;

$R^{16}$ and $R^{17}$ are independently selected from the group consisting of hydrogen, alkyl, alkoxy, alkoxyalkyl, and aminoalkyl.

Some preferred intermediates are those in which n is 1; U is oxygen; $R^2$ is 1-$R^4$, wherein:

$R^4$ is

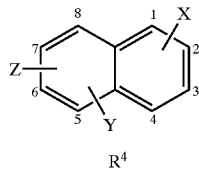

where

X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

T is oxygen or sulfur;

m is 2; and $R^1$ is halo.

Some particularly preferred intermediates are those in which n is 1; U is —$CH_2$—; $R^2$ is 1-$R^4$, wherein:

$R^4$ is

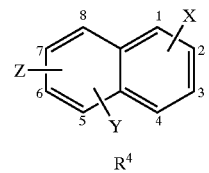

where

X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

T is oxygen;

m is 0; and $R^1$ is hydrogen or alkyl.

Additional preferred intermediates are those in which n is 0; U is —C(O) or —$CH_2$—; $R^2$ is hydrogen, halo or hydroxy; T is oxygen; m is 2; and $R^1$ is —$N(R^8)(R^9)$, where $R^8$ and $R^9$ are alkyl.

Additional novel intermediates are compounds of formula UU:

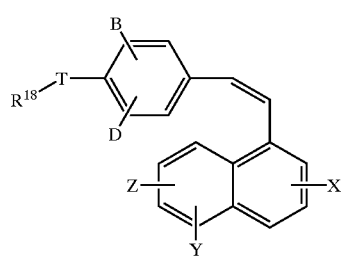

UU where

X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy; T is selected from the group consisting of oxygen, nitrogen, and sulfur; and $R^{18}$ is alkyl.

For the purposes of this invention, as regards to the above substituents, the following definitions apply:

The terms "alkyl" and "alkoxy", alone or as part of a larger moiety, include chains of 1 to 14 carbon atoms, preferably straight or branched alkyls of 1 to 6 carbon atoms; while "halogen" or "halo", alone or as part of a larger moiety, includes chlorine, bromine, fluorine, and iodine atoms. The terms "alkenyl" or "alkynyl", used alone or as part of a larger moiety, includes straight or branched chains of at least two carbon atoms containing at least one carbon—carbon double or triple bond, preferably upto 12 carbon atoms, more preferably, up to ten carbon atoms, most preferably up to seven c carbon atoms. The term "cycloalkyl" includes rings of three to twelve carbon atoms, preferably rings of three to six carbon atoms. The terms "haloalkyl" and "haloalkoxy", alone or as part of a larger moiety, include straight or branched chain alkyls of 1 to 14 carbon atoms, preferably lower straight or branched chain alkyls of 1 to 6 carbon atoms, wherein one or more hydrogen atoms have been replaced with halogen atoms, as, for example, trifluoromethyl or 2,2,2-trifluoroethoxy, respectively. "Aryl" refers to an aromatic ring structure, including fused rings, having 5 to 10 carbon atoms. "Heterocyclyl" refers to an aromatic ring structure, including fused rings, having at least one nitrogen, sulfur or oxygen atom. "Amino" refers to compounds of nitrogen that may be considered derived from ammonia and includes primary, secondary and tertiary amines wherein one or more of the hydrogen atoms is replaced with alkyl groups. "THF" refers to tetrahydrofuran, "DMF" refers to N,N-dimethylformamide, "DPAD" refers to 1,1'-(azodicarbonyl) dipiperidine, and "A.T." refers to ambient temperature.

The compounds of the present invention were prepared by methods generally known to those skilled in the art. Many of the compounds of the present invention in which $R^1$ is naphthyl were prepared in the manner shown in Schema 1. In Schema 1, a 4-hydroxy-benzaldehyde (SM1) was reacted with the appropriately substituted alkyl chloride hydrochloride salt (SM2) in a solvent, for example, DMF or THF, at 0° C. to ambient temperature in the presence of a base, for example, potassium carbonate, to yield the appropriately substituted alkoxy benzaldehyde (BB). The appropriately substituted benzaldehyde (BB) was then reduced in a solvent, for example methanol, with a reducing agent, for example, lithium aluminum hydride, sodium borohydride, or triacetoxyborohydride, to yield the appropriately substituted phenyl alkoxy alcohol (CC). The appropriately substituted phenyl alkoxy alcohol (CC) can also be prepared by reacting the appropriately substituted alkyl chloride hydrochloride salt (SM2) with either the appropriately substituted acid (SM3) or phenyl alcohol (SM4) in a solvent in the presence of a reducing agent as set forth above. The appropriately substituted phenyl alkoxy alcohol (CC) can then be reacted with either p-toluene sulfonyl chloride (SM5) and a base, for example triethylamine, in a solvent to form the appropriately substituted phenyl alkylthio- or alkoxysulfonyl toluene (DD) or sulfonyl chloride in a solvent to form the appropriately substituted phenylalkylthio or phenylalkoxy chloride hydrochloride (EE).

If necessary, the naphthyl ring can be prepared at this time. In general, the naphthyl ring was prepared via the formation of the appropriate naphthol. The preparation of the naphthol begins by reacting: 1) the appropriately substituted benzaldehyde (SM6) with either sodium hydride and 3-(triphenylphosphino)propanoate hydrochloride in THF and N-N-dimethylsulfoxide (DMF) or with succinic acid, disodium salt and acetic anhydride to form the appropriately substituted phenylbutenoic acid (FF); 2) the appropriately substituted phenyl iodide (SM7) with but-3-ynol, a base, for example, triethylamine, copper iodide and a palladium phosphine complex to yield the appropriately substituted phenylbutynol (GG); 3) the appropriately substituted phenylcarbonylpropanoic acid (SM8) with zinc and mercury (II) chloride in water to form the appropriately substituted phenylbutanoic acid (HH), which can also be preprepared by hydrogenating the appropriately substituted phenylbutenoic acid (FF) or phenylbutynol (GG) in alcohol with palladium on carbon followed by treatment with chromium oxide and sulfuric acid; 4) the appropriately substituted 2-(diethylaminocarbonyl)benzene (SM9) with n-butyllithium followed by prop-2-enylbromide and a dimethylthio-copper chloride complex to yield the appropriately substituted 2-(diethylaminocarbonyl)-3-prop-2-enylbenzene (JJ); or 5) the appropriately substituted benzene (SM10) with oxolan-2-one and aluminium chloride at elevated temperature to form the appropriately substituted trihydronaphthalen-1-one (KK). The trihydronaphthalen-1-one (KK) can also be prepared by reacting the appropriately substituted phenylbutanoic acid (HH) with an acid, for example polyphosphoric acid, or reacting the appropriately substituted 2-(diethylaminocarbonyl)-3-prop-2-enylbenzene (JJ) with methyllithium. The appropriately substituted trihydronaphthalen-1-one (KK) is then reacted with bromine in a solvent, for example methylene chloride, to form the the appropriately substituted 2-bromo-trihydronaphthalen-1-one (LL). The appropriately substituted 2-bromo-trihydronaphthalen-1-one (LL) is then reduced with a reducing agent and lithiumbromide in a solvent, for example, DMF, in the manner described above to form the appropriately substituted naphthol (MM), which is commercially available when (MM) is 4-chloronaphthol. The appropriately substituted naphthol (MM) was then reacted with either the appropriately substituted benzaldehyde (BB), alcohol (CC), toluene (DD), or hydrochloride (EE) to form the targeted 1-substitutedalkylthio or alkoxy-4-((substituted naphth-1-yl)oxyalkyl)benzene (I), for example, (2-(4-(((4-chloronaphthyl)methoxy)methyl)phenoxy)ethyl) diethylamine.

Additional substituents can be added to the naphthol ring by reacting a 6-aminonaphth-1-ol (SM11) with toluene sulfonyl chloride in the manner disclosed above to yield the 6-amino-1-(methylphenylsulfonyloxy)naphthalene (NN). The 6-amino-1-(methylphenylsulfonyloxy)naphthalene (NN) was then reacted with t-butyl nitrite in a solvent, for example at 0° C. followed by a copper (II) halide, for example, copper (II) chloride, to yield the appropriate 6-halo-1-(methylphenylsulfonyloxy)naphthalene (PP). The 6-amino-1-(methylphenylsulfonyloxy)naphthalene (NN) was also reacted with an excess of a copper (II) halide, for example, copper (II) chloride, in a solvent followed by t-butylnitrite in the manner disclosed above to form the appropriate 5,6-dihalo-1-(methylphenylsulfonyloxy) naphthalene (QQ). The appropriately substituted naphthalene (QQ) or (PP) can then reacted with a base, for example, potassium hydroxide, and an alcohol, for example, ethanol, in a mixture of a solvent, for example, THF, and water to yield the appropriately substituted naphthol (RR), for example 5,6-dichloronaphthol. When the naphthol was a 5,6-dihalonaphthol (RR) it was reacted with either the appropriately substituted benzaldehyde (BB), alcohol (CC), toluene (DD), or hydrochloride (EE) and a borane-pyridine complex under acidic conditions, or a base, for example, sodium hydride or triethylamine, in a solvent, for example DMF, or a phosphine complex, for example n-butylphosphine, and DPAD in a solvent, for example, THF, to form the targeted 1-substitutedalkylthio or alkoxy-4-((5,6-substituted naphth-1-yl)oxyalkyl)benzene (Ia), for example, (2-(4-((5,6-dichloronaphthyloxy)methyl)phenoxy) ethyl)diethylamine.

A halo substituent, for example chloro, can be added to the 4-position of naphthol ring at this time by reacting the appropriately substituted naphthol (MM) or (RR) with a sulfuryl halide, for example, sulfuryl chloride, in a solvent to yield the appropriately substituted 4-halonaphthol (SS). The appropriately substituted 4-halonaphthol (SS) can be reacted either the appropriately substituted benzaldehyde (BB), alcohol (CC), toluene (DD), or hydrochloride (EE) in the manner described above to form the targeted 1-substitutedalkylthio or alkoxy-4-((5,6-substituted naphth-1-yl)oxyalkyl)benzene (Ib), for example, (2-(4-((4,6-dichloronaphthyloxy)methyl)phenoxy)ethyl)diethylamine.

As depicted in Schema 2, compounds of the present invention wherein U is nitrogen and n is 1 were prepared by reacting the appropriately substituted benzaldehyde (BB) with the appropriately substituted 1-aminonaphthalene (SM12), for example, 1-amino-4-chloronaphthalene, under acidic conditions to form the appropriately substituted 1-aza-1-naphthyl-2-phenylethene (TT), which was then reduced with a reducing agent in the manner disclosed above to yield the targeted targeted 1-substituted-4-((substituted naphth-1-yl)aminoalkyl)benzene (IV), for example, (2-(4-(((4-chloronaphthyl)amino)methyl)phenoxy)-ethyl) diethylamine.

As depicted in Schema 3, compounds of the present invention wherein U is —CH$_2$— and n is 1 were prepared by reacting the appropriately substituted 1-aminonaphthalene (SM12) with the appropriately substituted 4-methylthio-, 4-methoxy-, or 4-methylamino-1-vinylbenzene (SM13) with t-butylnitrite, in a solvent, for example, acetonitrile, in the presence of palladium acetate to form the appropriately substituted 2-(4-methylthio-, 4-methoxy-, or 4-methylaminophenyl)vinylnaphthalene (UU). The vinylnaphthalene was then hydrogenated in a solvent, for example, ethanol, with a palladium on carbon to form the appropriately substituted 2-(4-methylthio-, 4-methoxy-, or 4-methylaminophenyl)ethylnaphthalene (WW). The ethylnaphthalene (WW) was then reacted in solvent, for example methylene chloride, with boron tribromide to form the appropriately substituted 2-(4-thio-, 4-hydroxy-, or 4-aminophenyl)ethylnaphthalene (XX). The ethylnaphthalene (XX) was in turn reacted with the appropriately substituted alkyl chloride hydrochloride salt (SM2) and an excess of a base, for example, potassium carbonate, in solvent, for example, DMF, to form the targeted 1-substituted-4-((substituted naphth-1-yl)ethyl)benzene (V), for example, (2-(4-(((4-chloronaphthyl)amino)methyl) phenoxy)-ethyl)diethylamine.

Schema 4 depicts another route in which the compounds of the present invention may be prepared. In Schema 4, the appropriately substituted benzaldehyde (SM3) is reacted with a haloalkylbromide, for example, 1-bromo-2-chloromoethane, to yield the appropriately substituted 4-haloalkoxybenzaldehdye (YY), which in turn is reduced with a reducing agent in an alcohol, for example methanol, in the manner described above to form the appropriately substituted 4-haloalkoxyphenylmethan-1-ol (ZZ). The phenylmethan-1-ol (ZZ) was then reacted at 0° C. to ambient temperature with the appropriately substituted naphthol or phenol (SM14), a phosphine complex, and DPAD in a solvent in the manner described above to yield the corresponding halo-1-(4-substituted naphthyl- or 4-substituted phenyl)oxy)methyl)phenoxy)alkane (AAA), for example, 2-chloro-1-(4-((4-chloronaphthyloxy)methyl)phenoxy) ethane. The alkane (AAA) was then reacted with the appropriate substituent, for example, cis-2,6-dimethylpiperidine, and a base in acetonitrile to form the corresponding, 1-(substituted alkoxy)-4-((4-substituted naphthyl or phenyl) oxy)methyl)benzene (VI), for example 1-(2-(2,6-dimethylpiperidyl)ethoxy)-4-((4-chloronaphthyloxy) methyl)benzene. At this point, the benzene (VI) can optionally be reacted with 3-chloroperoxybenzoic acid in chloroform at 0 C. to form the corresponding 2-(4-substituted naphthyl or phenyl)oxy)methyl)phenoxy)alkyl) alkanone (VII), for example, amino(2-(4-((5,6-dichloronaphthyloxy)methyl)phenoxy)ethyl)diethyl-1-one.

Schema 5 illustrates yet another route for preparing the compounds of the present invention wherein R$^1$ is a disubstituted amino. In schema 5, the appropriately substituted (4-hydroxyphenyl)methan-1-ol (SM4) was reacted with a bromomethylisocyanate and a reducing agent, for example potassium carbonate, in a solvent, for example, DMF, in the manner disclosed above to form the corresponding (4-(cyanomethoxy)phenyl)methan-1-ol (BBB). The methan-1-ol (BBB) was then reacted with sulfinyl chloride in a solvent, for example, chloroform, at 0° C. to form the corresponding 4-(cyanomethoxy)-1-(chloromethyl)benzene (CCC), which was in turn reacted with the appropriately substituted naphthol or phenol (SM14) and a reducing agent, for example, potassium carbonate, in a solvent, for example DMF, in the manner described above to yield the corresponding 1-(((4-substituted naphthyl- or 4-substituted phenyl)oxy)methyl)-4-(cyanomethoxy)benzene (DDD). The 4-(cyanomethoxy)benzene (DDD) was reacted with borane in a solvent, for example, THF, at 0° C. to form the appropriately substituted 1-(((4-substituted naphthyl- or 4-substituted phenyl)oxy)methyl)-4-(aminomethoxy) benzene (EEE). The 4-(aminomethoxy)benzene (EEE) was in turn reacted with the appropriate oxoalkyl chloride, for example, acetyl chloride, in a solvent, for example, pyridine or THF, at 0° C. to yield the corresponding 1-(((4-substituted naphthyl- or 4-substituted phenyl)oxy)methyl)-4-(oxoalkylaminomethoxy)benzene (FFF). The 4-(oxoalkylaminomethoxy)benzene (FFF) was then reacted with borane in a solvent in the manner described above to yield the targeted 1-(((4-substituted naphthyl- or 4-substituted phenyl)oxy)methyl)-4-(alkylaminomethoxy) benzene (VIII). At this point, additional moieties can be optionally added to the amino group by reacting the 4-(alkylaminomethoxy)benzene (VIII) with the appropriate substituted alkyl, alkoxy, or alkoxyalkyl halide and a base, for example, triethylamine, to yield the target 1-(((4-substituted naphthyl- or 4-substituted phenyl)oxy)methyl)-4-((disubstituted amino)methoxy)benzene (IX).

Schema 1

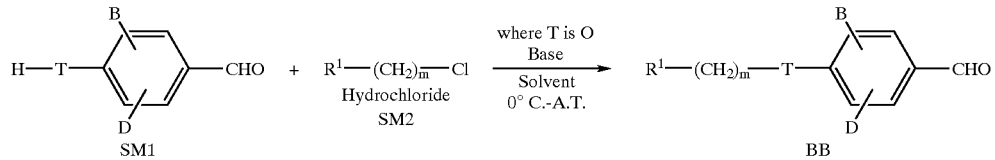

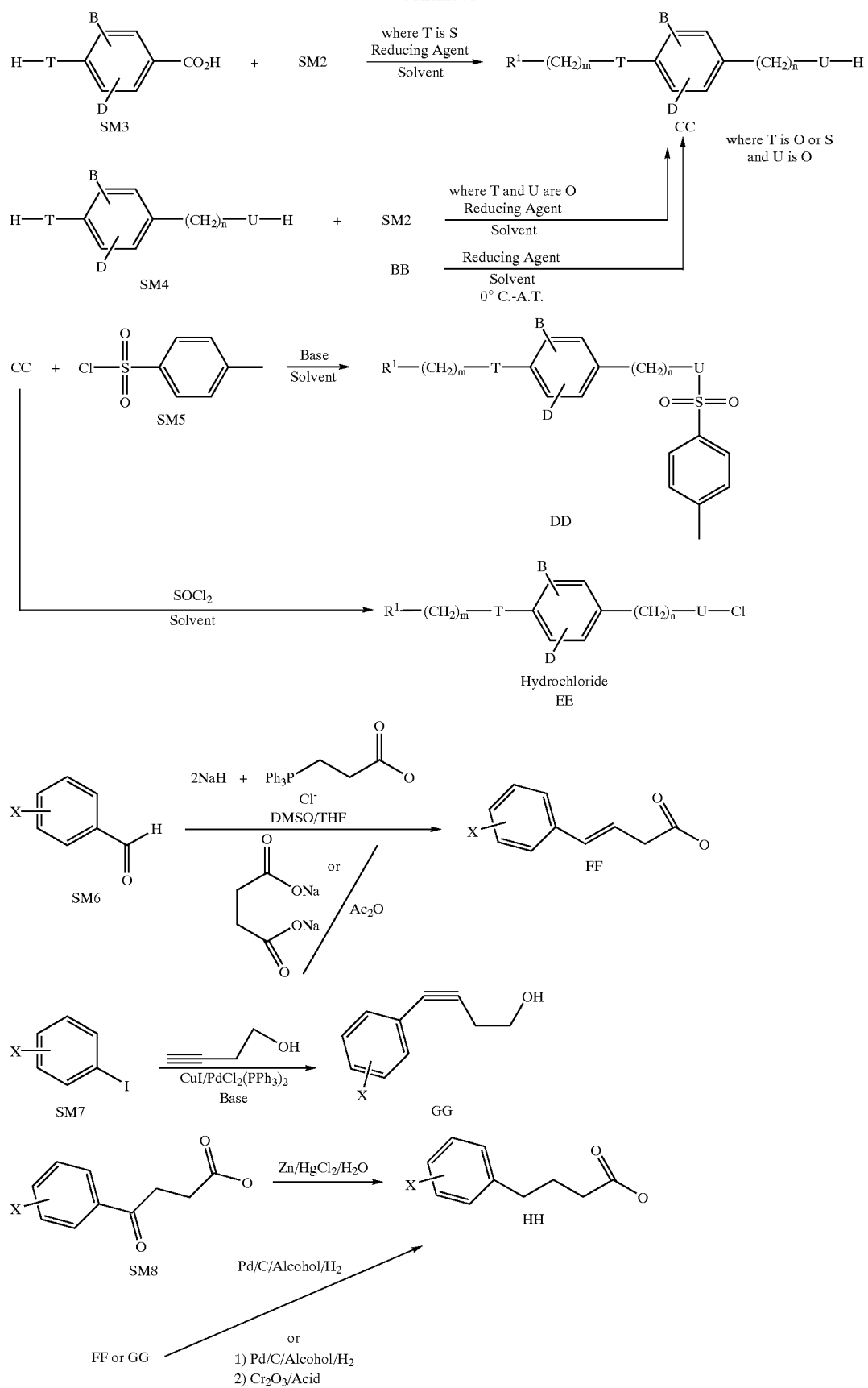

-continued
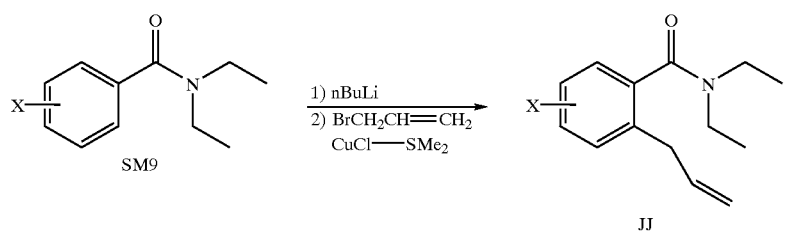
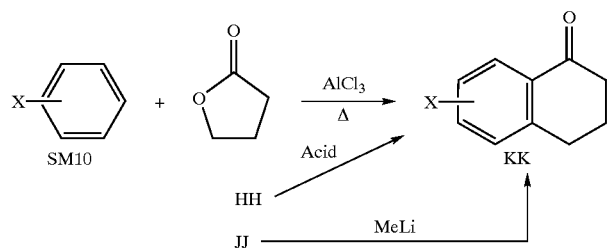
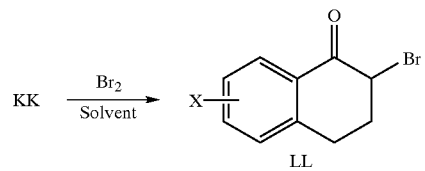
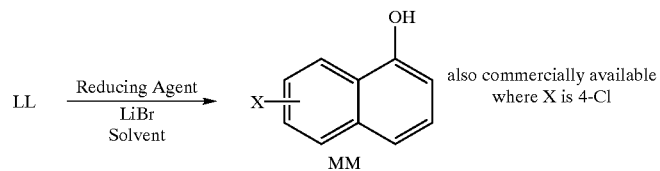
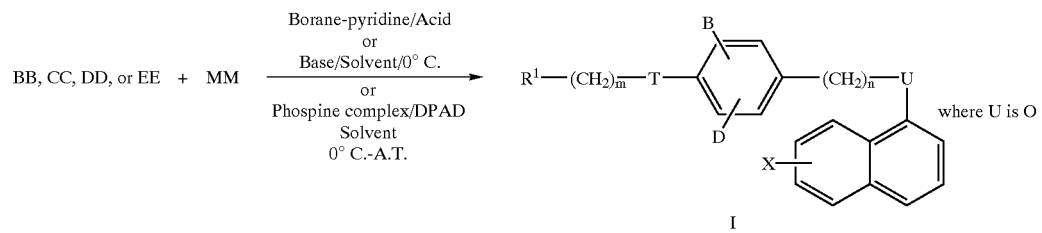
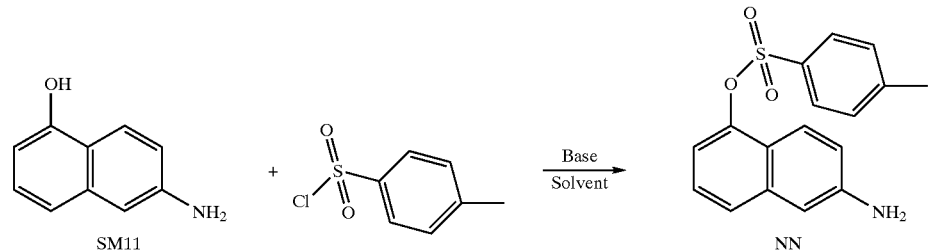

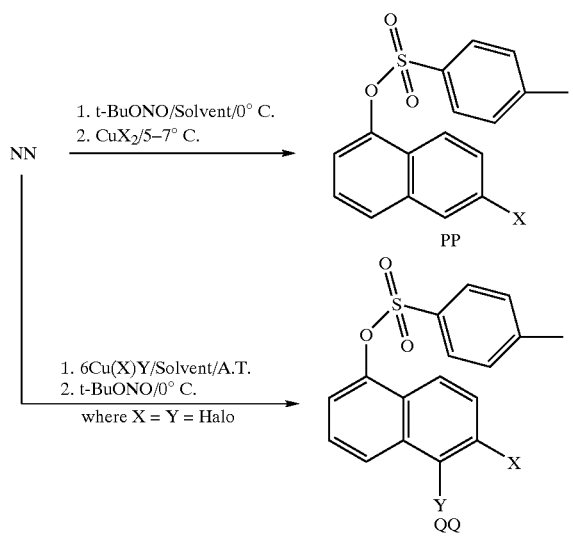
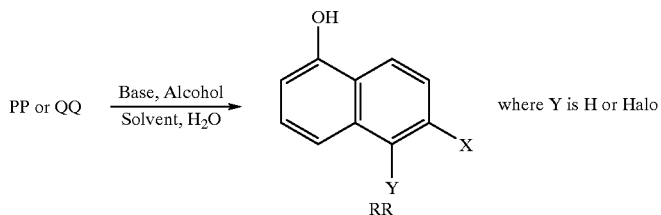
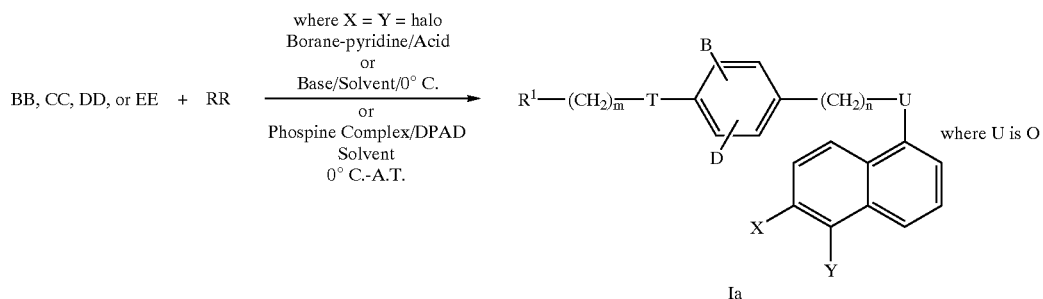
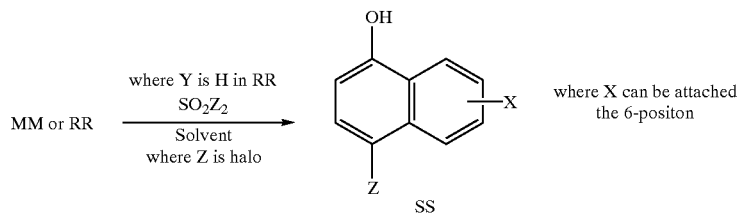
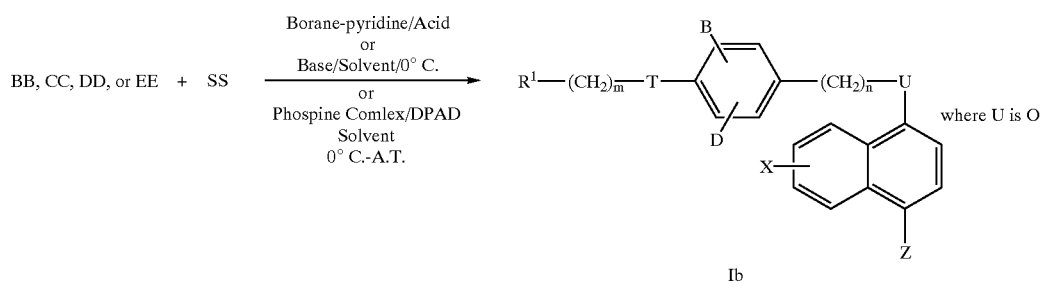

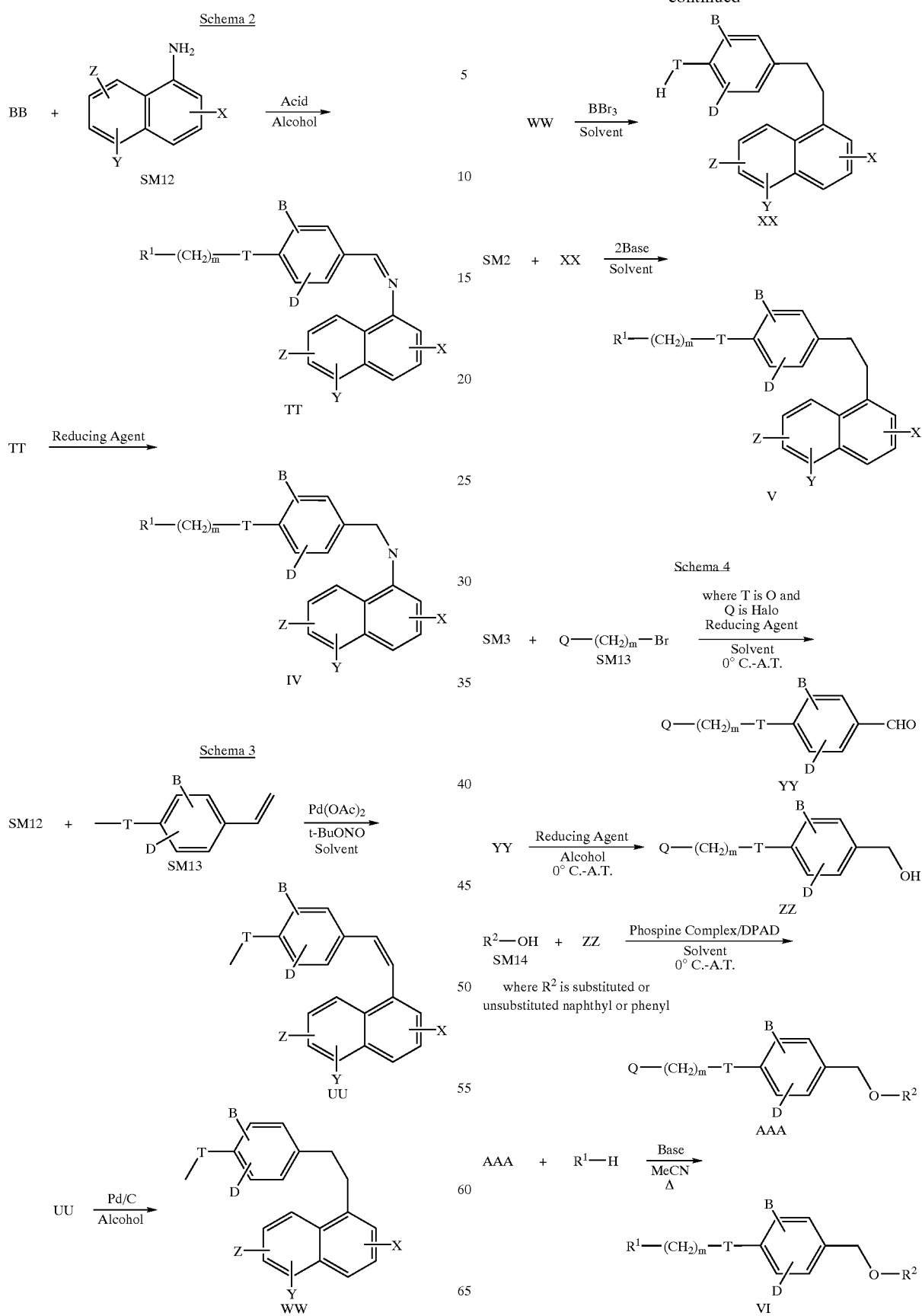

VI + ClC₆H₄CO₃H $\xrightarrow[0°C.]{CHCl_3}$

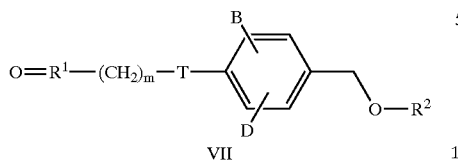
VII

Schema 5 where T and U are O
and m and n are 1

SM4 + NC—(CH₂)ₘ—Br $\xrightarrow[\substack{Solvent \\ A.T.}]{Reducing\ Agent}$

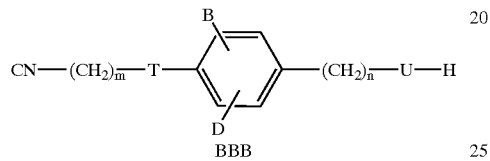
BBB

BBB $\xrightarrow[\substack{Solvent \\ 0°C.}]{SOCl_2}$

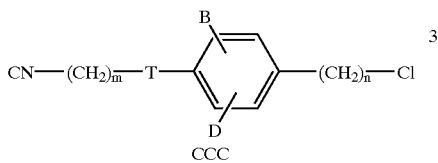
CCC

SM14 + CCC $\xrightarrow[Solvent]{Reducing\ Agent}$

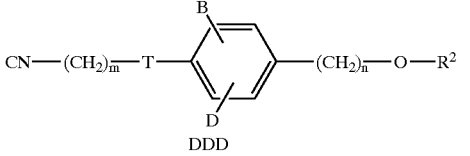
DDD

DDD $\xrightarrow[\substack{Solvent \\ 0°C.}]{Borane}$

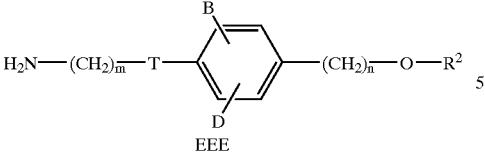
EEE where R⁸ is alkyl

EEE $\xrightarrow[\substack{Solvent \\ 0°C.}]{O=R^8—Cl}$

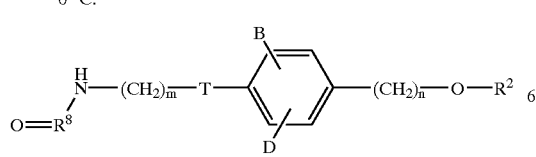
FFF

FFF $\xrightarrow[\substack{Solvent \\ 0°C.}]{Borane}$

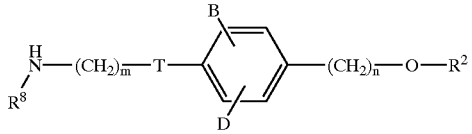
VIII

GGG + R⁹—Q $\xrightarrow{Base}$ where Q is halo and R⁹
is alkyl, alkoxy, or
alkoxyalkyl

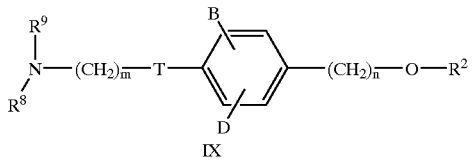
IX

The present invention is now described in more detail by reference to the following examples, but it should be understood that the invention is not construed as being limited thereto.

EXAMPLE 1

This example illustrates one protocol for the preparation of (2-(4-((5,6-dichloronaphthyloxy)methyl)phenoxy)ethyl) diethylamine (Compound 223).

Step A (6-aminonapthyl)((4-methylphenyl)-sulfonyl)oxy

A stirred solution of 5.0 grams (0.031 mole) of 6-amino-1-naphthol (available from TCI America, Portland, Oreg.) and 6.1 grams (0.032 mole) of p-toluenesulfonyl chloride (available from Aldrich Chemical Company, Milwaukee, Wis.) in 225 mL of methylene chloride (available from J. T. Baker Inc., Phillipsburg, N.J.) was cooled in an ice bath, and 5.3 grams (0.038 mole) of triethylamine was added dropwise. The reaction mixture was then allowed to warm to ambient temperature where it stirred for about 18 hours. After this time, the reaction mixture was washed with three 75 mL portions of water, dried with sodium sulfate, and filtered. The filtrate was concentrated under reduced pressure, yielding 9.1 grams of title compound. The NMR spectrum was consistent with the proposed structure.

Step B (5,6-dichloronapthyl)((4-methylphenyl) sulfonyl)oxy

Under a nitrogen atmosphere, 2.0 grams (0.0064 mole) of (6-aminonapthyl)((4-methylphenyl)sulfonyl)oxy was taken up in 6 mL of acetonitrile (available from EM Sciences, Gibbstown, N.J.). The mixture was stirred at ambient temperature for ten minutes and then 5.1 grams (0.038 mole) of copper (II) chloride was added. The resulting mixture was stirred at ambient temperature for ten minutes. At the conclusion of this period, the mixture was cooled in an ice bath and 0.85 mL (0.0064 mole) of t-butyl nitrite was added dropwise during a ten minute period. Upon completion of addition, the reaction mixture was stirred at 7–8° C. for 1.25 hours. At the conclusion of this period, the reaction mixture was poured into an ice-cold aqueous 10% hydrochloric acid solution and extracted with ethyl acetate. The extract was washed with one 25 mL portion of an aqueous solution saturated with sodium chloride, dried with sodium sulfate and filtered. The filtrate was concentrated under reduced pressure, yielding about 2.0 grams of crude product. The crude product was purified by column chromatography on silica gel, yielding 1.0 grams of title compound; mp 104–109° C. The NMR spectrum was consistent with the proposed structure.

Step C 5,6-dichloronaphthol

To a mixture of 0.85 gram (0.0023 mole) of (5,6-dichloronapthyl)((4-methylphenyl)sulfonyl)oxy in 40 mL of ethanol (available from J. T. Baker Inc.) was added 5 mL of tetrahydrofuran (THF, available from Aldrich Chemical Company). The resulting mixture was stirred to effect dissolution and then a solution of 1.3 grams (0.023 mole) of potassium hydroxide (available from VWR Scientific Products, Bridgeport, N.J.) in 40 mL of water was added. Upon completion of addition, the reaction mixture was under reflux for one hour. After this time, most of the solvent was removed under reduced pressure to yield a residue. The residue was extracted with one 20 mL portion of diethyl ether. The extract was acidified to a pH of 5–6 with ice-cold aqueous 5% hydrochloric acid and then extracted with ethyl acetate. The ethyl acetate extract was washed with an aqueous solution saturated with sodium chloride, dried with sodium sulfate and filtered. The filtrate was concentrated under reduced pressure, yielding 0.33 gram of title compound. The NMR spectrum was consistent with the proposed structure.

Step D (4-(2-diethylamino)ethoxy)phenyl)-methan-1-ol

A solution of 37.2 grams (0.22 mole) of 2-(diethylamino) ethyl chloride hydrochloride (available from Aldrich Chemical Company), 26.8 grams (0.22 mole) of 4-hydroxybenzyl alcohol (available from Aldrich Chemical Company) and 89 grams (0.65 moles) of potassium carbonate (available from VWR Scientific Products) in 1200 mL of N,N-dimethylformamide (DMF, available from EM Sciences) was stirred at ambient temperature for about 18 hours. After this time, the solvent was remove under reduced pressure, yielding a residue. The residue was taken up in water and then extracted with ethyl acetate. The extract was washed with one portion of an aqueous 10% sodium hydroxide solution followed by one portion of water and then one portion of an aqueous solution saturated with sodium chloride, dried with sodium sulfate and filtered. The filtrate was concentrated under reduced pressure, yielding 2.38 grams of title compound. The NMR spectrum was consistent with the proposed structure.

Step E Compound 223

A stirred solution of 0.33 gram gram (0.0016 mole) of 5,6-dichloronapthol and 0.35 gram (0.0016 mole) of (4-(2-diethylamino)ethoxy)phenyl)methan-1-ol in 15 mL of THF was cooled in an ice bath, and 0.24 mL (0.0017 mole) of tributylphosphine (available from Aldrich Chemical Company) followed by 0.42 gram (0.0017 mole) of 1-1'-(azadicarbomyl)dipiperidine (available from Aldrich Chemical Company) were added. Upon completion of addition, the reaction mixture was allowed to warm to ambient temperature where it stirred for 72 hours. After this time, the reaction mixture was diluted with ethyl acetate, and an aqueous solution saturated with sodium chloride was added. The organic layer was separated, dried with magnesium sulfate, and filtered. The filtrate was concentrated under reduced pressure, yielding about 0.45 gram of crude product. The crude product was purified by column chromatography on silica gel, yielding 0.13 gram of Compound 223. The NMR spectrum was consistent with the proposed structure.

EXAMPLE 2

This example illustrates one protocol for the preparation of the hydrochloride salt of (2-(4-((5,6-dichloronaphthyloxy)methyl)phenoxy)ethyl)diethylamine (Compound 224).

Compound 225 (prepared in the manner of Example 1), 0.07 gram (0.00017 mole), was taken up in 1 mL of methylene chloride (available from EM Sciences) and 1 mL of one molar hydrochloric acid in diethyl ether (available from Aldrich Chemical Company) was added. The solvent was removed under reduced pressure to yield a solid. The solid was taken up in heptane. The resulting precipitate was collected by vacuum filtration, yielding 0.07 gram of Compound 226; mp 204–206° C. The NMR spectrum was consistent with the proposed structure.

EXAMPLE 3

This example illustrates one protocol for the preparation of (2-(4-((6-quinolylamino)methyl)phenoxy)ethyl) diethylamine (Compound 15).

Step A 4-(2-(diethylamino)ethoxy)benzaldehyde

A solution of 5.0 grams (0.041 mole) of 4-hydroxybenzaldehdye (available from Aldrich Chemical Company), 8.5 grams (0.049 mole) of 2-diethylaminoethyl chloride hydrochloride (available from Aldrich Chemical Company), and 13.5 grams (0.098 mole) of potassium carbonate (available from J. T. Baker Inc.) in 100 mL of DMF was stirred at ambient temperature for 72 hours. At the conclusion of this period, the reaction mixture was poured into 100 mL of water and extracted with three 50 mL portions of diethyl ether. The combined extracts were washed with one 25 mL portion of water, dried with sodium sulfate, and filtered. The filtrate was concentrated under reduced pressure, yielding 5.1 grams of title compound. The NMR spectrum was consistent with the proposed structure.

Step B Compound 15

To a stirred solution of 1.0 gram (0.0045 mole) of 4-(2-(diethylamino)ethoxy)benzaldehyde and 0.65 gram (0.0045 mole) of 6-aminoquinoline (available from Aldrich Chemical Company) in 25 mL of 1,2-dichloroethane (DCE, available from Aldrich Chemical Company) was added 0.3 mL (0.0045 mole) of glacial acetic acid (available from J. T. Baker Inc.) followed by 1.4 grams (0.0068 mole) of sodium triacetoxyborohydride (available from Aldrich Chemical Company). Upon completion of addition, the reaction mixture was stirred at ambient temperature for three hours. At the conclusion of this period, 50 mL of 10% aqueous sodium hydroxide was added dropwise. The resulting solution was extracted with three 25 mL portions of diethyl ether. The extracts were combined, washed with one 25 mL portion of an aqueous solution saturated with sodium chloride, dried with sodium sulfate and filtered. The filtrate was concentrated under reduced pressure, yielding 1.25 grams of a dark brown paste. The dark brown paste was purified by column chromatography on silica gel, yielding 0.13 gram of Compound 15. The NMR spectrum was consistent with the proposed structure.

EXAMPLE 4

This example illustrates one protocol for the preparation of (2-(4-(((4-chloronaphthyl)amino)methyl)-2-methoxyphenoxy)ethyl)diethylamine (Compound 263).

Step A 4-(2-(diethylamino)ethoxy)-2-methoxybenzaldehyde

This compound was prepared in the manner of Step A, Example 3, using 2.5 grams (0.016 mole) of 4-hydroxy-2- methoxybenzaldehdye (available from Lancaster Synthesis Inc., Windham, N.H.), 3.4 grams (0.02 mole) of 2-diethylaminoethyl chloride hydrochloride, and 5.5 grams (0.04 mole) of potassium carbonate in 75 mL of DMF. The yield of the title compound was 2.6 grams. The NMR spectrum was consistent with the proposed structure.

Step B Compound 263

This compound was prepared in the manner of Step B, Example 3, using 1.0 gram (0.004 mole) of 4-(2-(diethylamino)ethoxy)-2-methoxybenzaldehyde, 0.71 gram (0.004 mole) of 1-amino-4-chloronaphthalene (available from Aldrich Chemical Company), 0.25 mL (0.004 mole) of glacial acetic acid, 1.3 grams (0.006 mole) of sodium triacetoxyborohydride and 50 mL of 1,2-dichloroethane (DCE). The yield of Compound 263 was 0.52 gram. The NMR spectrum was consistent with the proposed structure.

EXAMPLE 5

This example illustrates one protocol for the preparation of (2-(4-(((4-chloronaphthyl)methoxy)methyl)phenoxy)ethyl)diethylamine (Compound 8).

Step A (4-(2-diethylamino)ethoxy)phenyl)-methan-1-ol

A solution of 4.0 grams (0.08 mole) of 4-(2-(diethylamino)ethoxy)benzaldehyde (prepared in the manner of Step A, Example 3) and 2.7 grams (0.08 mole) of sodium borohydride (available from Aldrich Chemical Company) in 40 mL of methanol (available from J. T. Baker Inc,) was stirred at ambient temperature for about 18 hours. After this time, the reaction mixture was quenched with water and extracted with several portions of methylene chloride. The organic extracts were combined, dried with magnesium sulfate, and filtered. The filtrate was concentrated under reduced pressure, yielding 4.1 grams of title compound.

Step B 4-chloronaphthalenecarbaldehye

To a stirred solution of 6.7 grams (0.026 mole) of a 1.0M solution of tin(iv) chloride in dichloromethane (available from Aldrich Chemical Company) in 10 mL of methylene chloride was added 3.0 grams (0.026 mole) of ↻,↻-dichloromethyl methyl ether (available from Aldrich Chemical Company). The resulting solution was stirred for one hour at ambient temperature. After this time, a solution of 2.8 mL (0.021 mole) of 4-chloronaphthalene was added. Upon completion of addition, the reaction mixture was stirred at ambient temperature for about 18 hours. At the conclusion of this period, the reaction mixture was quenched with water, washed with water followed by an aqueous solution saturated with sodium chloride, dried with sodium sulfate and filtered. The filtrate was concentrated under reduced pressure, yielding about 2.1 grams of title compound.

Step C (4-chloronaphthyl)methan-1-ol

This compound was prepared in the manner of Step C, Example 1, using 2.1 grams (0.011 mole) of 4-chloronaphthalenecarbaldehye, 70 mL of methanol, 20 mL of THF, and 2 grams (0.054 mole) of sodium borohydride. This preparation differs in that sodium borohydride was used rather than a solution of potassium hydroxide in water. The yield of the title compound was 1.9 grams.

Step D Compound 8

This compound was prepared in the manner of Step E, Example 1, using 0.5 gram (0.0026 mole) of (4-chloronaphthyl)methan-1-ol, 0.6 gram of (4-(2-diethylamino)ethoxy)phenyl)methan-1-ol, 70 mL of THF, 0.79 mL (0.0031 mole) of tributylphosphine, and 0.73 gram (0.0029 mole) of 1-1'-(azadicarbomyl)dipiperidine. The yield of Compound 8 was 0.3 gram.

EXAMPLE 6

This example illustrates one protocol for the preparation of 1-(2-(2,6-dimethylpiperidyl)ethoxy)-4-((4-chloronaphthyloxy)methyl)benzene (Compound 106).

Step A Mixture of 4-(2-bromoethoxy)benzaldehyde and 4-(2-chloroethoxy)benzaldehyde Sodium hydride (60% dispersion in mineral oil, available from Aldrich Chemical Company), 4.4 grams (0.11 mole), was washed with three portion of hexane (available from J. T. Baker Inc.) and 200 mL of DMF was added. The resulting mixture was cooled to 0 C. and 50 mL (0.6 mole) of 1-bromo-2-chloromoethane (available from Aldrich Chemical Company) followed by 12.2 grams (0.1 mole) 4-hydroxybenzaldehyde were added. Upon completion of addition, the reaction mixture was heated to 40° C. where it stirred for about 72 hours. After this time, the reaction mixture was extracted with several portions of ethyl acetate. The organic extracts were combined, dried with magnesium sulfate, and filtered. The filtrate was concentrated under reduced pressure, yielding 7.4 grams of title mixture. The NMR spectrum was consistent with the proposed structure. This compound was prepared several times in the manner described above.

Step B Mixture of (4-(2-bromoethoxy)phenyl) methan-1-ol and (4-(2-chloroethoxy)phenyl)-methan-1-ol This compound was prepared in the manner of Step C, Example 1, using 8.7 grams (0.047 mole) of the mixture of 4-(2-bromoethoxy)benzaldehyde and (4-(2-chloroethoxy) phenyl)methan-1-ol, 400 mL of methanol, and 3.5 grams (0.094 mole) of sodium borohydride. This preparation differs in that no THF was used and sodium borohydride was used rather than a solution of potassium carbonate in water. The yield of the title mixture was 8.4 grams. The NMR spectrum was consistent with the proposed structure.

Step C. 2-chloro-1-(4-((4-chloronaphthyloxy) methyl)phenoxy)ethane

A stirred solution of 8.4 grams (0.045 mole) of the mixture of (4-(2-bromoethoxy)phenyl)methan-1-ol and (4-(2-chloroethoxy)phenyl)methan-1-ol, 8.1 grams (0.045 mole) of 4-chloronaphthol, and 13.7 mL (0.054 mole) of tributylphosphine in 500 mL of THF was cooled in an ice bath and 12.6 grams (0.049 mole) of 1-1'-(azodicarbomyl) dipiperidine was added. Upon completion of addition, the reaction mixture was allowed to warm to ambient temperature where it stirred for 24 hours. After this time, the solvent was reduced under reduce pressure, yielding a solid. The solid was purified by column chromatography on silica gel, yielding 15 grams of crude product. The crude product was further purified by column chromatography on silca gel, yielding 6.7 grams of title compound.

Step D Compound 106

A stirred mixture of 0.4 grams (0.001 mole) of 2-chloro-1-(4-((4-chloronaphthyloxy)methyl)phenoxy)ethane and 5 mL (0.037 mole) of cis-2,6-dimethylpiperidine was heated to just below reflux for about 72 hours. After this time, the reaction mixture was analyzed by thin layer chromatography (TLC), which indicated the reaction was incomplete. The reaction mixture was concentrated under reduced pressure and subject to column chromatography on silica gel, yielding 0.2 gram of compound 106. The NMR spectrum was consistent with the proposed structure.

EXAMPLE 7

This example illustrates one protocol for the preparation of amino(2-(4-((5,6-dichloronaphthyloxy)methyl)phenoxy) ethyl)diethyl-1-one (Compound 183).

(2-(4-((5,6-Dichloronaphthyloxy)methyl)phenoxy)ethyl) diethylamine (prepared in the manner of Example 1), 0.1 gram (0.0003 mole), was taken up in 10 mL of chloroform (available from EM Sciences). The resulting solution was cooled to 0° C. in an ice bath and 0.09 gram (0.0004 mole) of 3-chloroperoxybenzoic acid (available from Aldrich Chemical Company) was added. Upon completion of addition, the resulting mixture was stirred for ten minutes and then the ice bath was removed. The reaction mixture was allowed to warm to ambient temperature where it stirred for 35 minutes. At the conclusion of this period, the reaction mixture was poured into a solution of 25 mL of chloroform and 10 mL of aqueous 5% sodium hydroxide. The organic layer was separated, dried with sodium sulfate and filtered. The filtrate was concentrated under reduced pressure, yielding 0.15 gram of compound 183; mp 81–87° C. The NMR spectrum was consistent with the proposed structure.

EXAMPLE 8

This example illustrates one protocol for the preparation of (2-(4-((4,6-dichloronaphthyloxy)methyl)phenoxy)ethyl) diethylamine (Compound 216).

Step A 4,6-dichloronaphthol

This compound was prepared in the manner of Step B, Example 1, using 5.0 grams (0.029 mole) of 6-aminonaphthol, 200 mL of acetonitrile, 4 grams (0.03 mole) of copper (II) chloride, and 3.3 grams (0.032 mole) of t-butyl nitrite. The yield of the title compound was 1.4 grams.

Step B Compound 216

This compound was prepared in the manner of Step E, Example 1, using 0.4 gram (0.0022 mole) of 4,6-dichloronaphthol, 0.49 gram (0.0022 mole) of (4-(2-diethylamino)ethoxy)phenyl)methan-1-ol, 80 mL of THF, 0.5 gram (0.0025 mole) of tributylphosphine, and 0.55 gram (0.0022 mole) of 1-1'-(azodicarbomyl)dipiperidine. The yield of Compound 216 was 0.3 gram.

EXAMPLE 9

This example illustrates one protocol for the preparation of (2-(4-(((4-chloronaphthyl)amino)methyl)phenoxy)ethyl) diethylamine (Compound 84).

A stirred solution of 0.2 gram (0.0001 mole) of 4-(2-(diethylamino)ethoxy)benzaldehyde (prepared in the manner of Step A, Example 3), 0.22 gram (0.0001 mole) of 1-amino-4-chloronaphthalene (available from Aldrich Chemical Company), and one drop of p-toluenesulfonic acid monohydrate (available from Aldrich Chemical Company) in 5 mL of toluene was heated at reflux for ten hours. At the conclusion of this period, the reaction mixture was concentrated under reduced pressure, yielding a residue. The residue was taken up in 5 mL of methanol and about 0.2 grams (0.004 mole) of sodium borohydride was added. The resulting mixture was stirred at ambient temperature for about 18 hours. After this time, the mixture was quenched with water and extracted with several portions of diethyl ether. The extracts were combined, dried with sodium sulfate and filtered. The filtrate was concentrated under reduced pressure, yielding 0.8 gram of Compound 84. The NMR spectrum was consistent with the proposed structure.

EXAMPLE 10

This example illustrates one protocol for the preparation of (2-(4-(((4-chloronaphthyl)amino)methyl)phenylthio) ethyl)diethylamine (Compound 71).

Step A (4-(2-diethylamino)ethylthio)phenyl)-methan-1-ol

Under a nitrogen atmosphere, 0.6 gram (0.017 mole) of lithium aluminum hydride (available from Aldrich Chemical Company) was taken up in 20 mL of THF. The resulting mixture was stirred to effect dissolution and a solution of one gram (0.007 mole) of 2-mercaptobenzoic acid (available from Aldrich Chemical Company) 10 mL of THF was added. The resulting was stirred for 70 minutes. At the conclusion of this period, the solution was cooled in an ice bath and 10 mL of ethyl acetate was carefully added during a 30 minute period. Upon completion of addition, 5 mL of water followed by 1.3 grams (0.008 mole) of 2-(diethylamino)ethyl chloride hydrochloride was added. Upon completion of addition, the reaction mixture was allowed to warm to ambient temperature where it stirred for about 18 hours. After this time, about 10 mL of aqueous 10% sodium hydroxide followed by an addition 10 mL of ethyl acetate was added. The resulting mixture was filtered. The organic layer of the filtrate was separated from the aqueous layer, washed with an aqueous solution saturated with sodium chloride, dried with sodium sulfate and filtered, yielding 3.32 grams of a yellow liquid. The yellow liquid was purified by column chromatography on silica gel, yielding 0.5 gram of title compound. The NMR spectrum was consistent with the proposed structure.

Step B 4-(2-(diethylamino)ethylthio)benzaldehyde

Under a nitrogen atmosphere, a stirred solution of 0.2 mL (0.003 mole) of dimethyl sulfoxide (DMSO, available from Aldrich Chemical Company) in 10 mL of methylene chloride of was cooled to –60° C. and 0.2 mL (0.002 mole) of oxalyl chloride (available from Aldrich Chemical Company) was added. The resulting solution was stirred at –60° C. for 15 minutes. At the conclusion of this period, a solution of 0.5 gram (0.002 mole) of (4-(2-diethylamino)ethylthio)phenyl) methan-1-ol in about 20 mL of methylene chloride was added. The mixture was stirred at –60° C. to –40° C. of 30 minutes and 1.5 mL (0.011 mole) of triethylamine was added. Upon completion of addition, the reaction mixture was stirred at –40° C. for 1.5 hours. At the conclusion of this period, the reaction mixture was filtered through a silica gel plug. The filter cake was washed with one 150 mL portion of ethyl acetate. The filtrate was concentrated under reduced pressure, yielding 0.2 gram of title compound. The NMR spectrum was consistent with the proposed structure.

Step C Mixture of (2-(4-(2-aza-2-(4-chloronaphthyl)vinyl)phenylthio)ethyl)-diethylamine and Compound 71

A solution of 0.2 (0.001 mole) of 4-(2-(diethylamino) ethylthio)benzaldehyde, 0.2 gram 6-amino-4-chloronaphthalene, 0.4 gram (0.002 mole) of sodium triacetoxyborohydride and 10 drops of glacial acetic acid in 10 mL of DCE was stirred at ambient temperature for about 18 hours. At the conclusion of this period, 50 mL of 10% aqueous sodium hydroxide followed by 75 mL of ethyl acetate was added. The organic layer was separated from the aqueous layer and filtered through phase separated filter paper, yielding 0.4 gram of crude product. This crude product was combined with 0.1 gram of crude product prepared in a similar experiment to yield a total of 0.5 gram of crude product. The 0.5 gram of crude product was purified by column chromatography on silica gel, yielding 0.1 gram of mixture of (2-(4-(2-aza-2-(4-chloronaphthyl)vinyl)phenylthio)ethyl)diethylamine and Compound 71. The NMR spectrum was consistent with the proposed structure.

Step D Compound 71

A stirred solution of 0.1 gram (0.0008 mole) of borane-dimethylamine complex (available from Aldrich Chemical Company) and 0.1 gram (0.0003 mole) of the mixture of (2-(4-(2-aza-2-(4-chloronaphthyl)vinyl)phenylthio)ethyl)diethylamine and Compound 71 in 2 mL of glacial acetic acid was heated at 60° C. for three hours. After this time, the reaction mixture was allowed to cool to ambient temperature and 5 ml of ethyl acetate was added. The resulting mixture was washed with an aqueous 10% sodium hydroxide solution. The organic layer was separated from the aqueous layer and filtered through phase separation filter paper, yielding 0.1 gram of an oil. The oil was purified by column chromatography on silica gel, yielding 0.1 gram of product The 0.1 gram of product was combined with 0.1 gram of product from a previous experiment to yield 0.2 gram of Compound 71. The NMR spectrum was consistent with the proposed structure.

EXAMPLE 11

This example illustrates one protocol for the preparation of diethyl(2-(4-((2,3,4-trichlorophenoxy)methyl)phenoxy)ethyl)amine (Compound 308).

Step A (2-(4-chloromethyl)phenoxy)ethyl)diethylamine Hydrochloride

Under a nitrogen atmosphere, 2 mL (0.027 mole) of thionyl chloride (available from J. T. Baker Inc.) was added dropwise to a stirred solution of 5.8 grams (0.026 mole) of 4-(2-(diethylamino)ethoxy)benzaldehyde (prepared in the manner of Step A, Example 3) in 150 mL of methylene chloride. Upon completion of addition, the reaction mixture was stirred at ambient temperature for about 2.5 hours. After this time, the reaction mixture was heated to 50° C. and the solvent was removed under reduced pressure, yielding 7.2 grams of title compound. The NMR spectrum was consistent with the proposed structure.

Step B Compound 308

A stirred solution of 0.3 gram (0.001 mole) of (2-(4-chloromethyl)phenoxy)ethyl)diethylamine hydrochloride, 0.2 gram (0.0009 mole) of 2,3,4-trichlorophenol (available from Aldrich Chemical Company), 0.9 gram (0.003 mole) of cesium carbonate (available from Aldrich Chemical Company) and a catalytic amount of sodium iodide (available from Aldrich Chemical Company) in 10 mL of acetone (available from J. T. Baker Inc.) was heated to 60 C. for about 18 hours. After this time, the solvent was removed under reduced pressure and about 10 mL of methylene chloride was added. The resulting solution was filtered, and the filtrate was filtered through a silica gel pad, yielding 0.2 gram of Compound 308. The NMR spectrum was consistent with the proposed structure.

EXAMPLE 12

This example illustrates one protocol for the preparation of diethyl(2-(4-((2,5-difluorophenoxy)methyl)phenoxy)ethyl)amine (Compound 346).

This compound was prepared in the manner of Step B, Example 11, using 0.3 gram (0.001 mole) of (2-(4-chloromethyl)phenoxy)ethyl)diethylamine hydrochloride, 0.1 gram (0.0009 mole) of 2,5-difluorophenol (available from Aldrich Chemical Company), 0.9 gram (0.003 mole) of cesium carbonate and a catalytic amount of sodium iodide in 10 mL of acetone. The yield of Compound 346 was 0.2 gram. The NMR spectrum was consistent with the proposed structure.

EXAMPLE 13

This example illustrates one protocol for the preparation of 1,2-dichloro-5-{[4-(4-ethylpiperazinyl)phenyl]methoxy}naphthalene (Compound 355).

Step A 4-piperazinylbenzonitrile

Under a nitrogen atmosphere, a stirred mixture of 10.0 grams (0.055 mole) of 4-bromobenzonitrile (available from Aldritch Chemical Company) and 23.7 grams (0.28 mole) of piperazine (available from Aldritch Chemical Company) was heated at 120° C. for about 45 hours. After this time, the reaction mixture was taken up in 150 ml of aqueous 10% sodium hydroxide. The resulting solution was extracted with three 50 mL portions of methylene chloride. The combined extracts were washed with one 50 mL portion of an aqueous saturated sodium chloride solution, dried with sodium sulfate, and filtered. The filtrate was concentrated under reduced pressure, yielding 8.6 grams of a green paste. The green paste was purified by column chromatography on silica gel, yielding 3.8 grams of a paste. The paste was taken up in 50 mL of diethyl ether. The resulting solution was warmed on a rotovap and decanted away from the insoluble paste. The decantate was concentrated, yielding 3.2 grams of the title compound. The NMR spectrum was consistent with the proposed structure.

Step B 4-(4-ethyl)piperazinylbenzonitrile

Under a nitrogen atmosphere, a stirred solution of 3.16 grams (0.017 mole) of 4-piperazinylbenzonitrile, 2.0 mL (0.025 mole) of iodoethane (available from Aldritch Chemical Company), and 7.1 mL (0.051 mole) of triethylamine in 50 mL of THF was heated at reflux for about three hours. At the conclusion of this period, the reaction mixture was allowed to cool to ambient temperature and 100 mL of water was added. The resulting solution was extracted with two 50 mL portions of diethyl ether. The combined extracts were washed with 100 mL portion of water, dried with sodium sulfate, and filtered. The filtrate was concentrated under reduced pressure, yielding 3,2 grams of crude product. The crude product was purified by column chromatography on silica gel, yielding 2.9 grams of tilte compound. The NMR spectrum was consistent with the proposed structure.

Step C [4-(4-ethylpiperazinyl)benzaldehyde

Under a nitrogen atmosphere, a stirred solution of 2.8 grams (0.013 mole) of 4-(4-ethyl)piperazinylbenzonitrile in 35 mL of anhydrous toluene (available from Aldrich Chemical Company) was cooled to −70° C. and 12 mL (0.02 mole) of diisobutylaluminum hydride (1.5M in toluene, available from Aldritch Chemical Company) was added dropwise at a rate to maintain the temperature below −60° C. during about a 15 minute period. Upon completion of addition, the reaction mixture was stirred at −60° C. for two hours. At the conclusion of this period, 10 mL of methanol was added dropwise followed by 10 mL of water. The resulting solution was allowed to warm to ambient temperature. Once at the prescribed temperature, 10 mL of methylene chloride was added. The resulting mixture was filtered and the filtrate was transferred to a separatory funnel. The organic layer was separated from the aqueous layer, dried with sodium sulfate, and filtered. The filtrate was concentrated under reduced pressure, yielding 1.6 grams of an orange paste. The orange pasted was was filtered through a silica gel plug. The filter cake was washed with one 75 mL portion of methylene chloride followed by one 50 mL portion of a 5% methanol/95% methylene chloride solution. The filtrate was concentrated under reduced pressure, yielding 0.5 gram of title compound. The NMR spectrum was consistent with the proposed structure.

Step D [4-(4-ethylpiperazinyl)phenyl]methan-1-ol

This compound was prepared in the manner of Step A, Example 5, using 0.4 gram (0.019 mole) of [4-(4-ethylpiperazinyl)benzaldehyde and 0.4 gram (0.01 mole) of sodium borohydride in 40 mL of absolute ethanol (available from J. T. Baker Inc.) The yield of the title compound was 0.3 gram. The NMR Spectrum was consistend with the proposed structure.

Step E Compound 355

This compound was prepared in the manner of Step E, Example 1, using 0.23 gram gram (0.0011 mole) of 5,6-dichloronapthol, 0.25 gram (0.0011 mole) of [4-(4-ethylpiperazinyl)phenyl]methan-1-ol, 0.36 mL (0.0014 mole) of tributylphosphine, and 0.35 gram (0.0014 mole) of 1-1'-(azadicarbomyl)dipiperidine in 15 mL of THF. The yield of compound 355 was 0.04 gram. The NMR spectrum was consistent with the proposed structure.

EXAMPLE 14

This example illustrates one protocol for the preparation of 5-{[4-(8-aza-1,4-dioxaspiro[4.5]dec-8-yl)phenyl]methoxy}-1,2-dichloronaphthalene (Compound 362).

Step A 5-[(4-bromophenyl)methoxy]-1,2-dichloronaphthalene

A stirred mixture of 4.0 grams (0.019 mole) of 5,6-dichloronapthol in 60 mL of THF was cooled in an ice bath and 1.1 grams (0.023 mole) of Sodium hydride (60% dispersion in mineral oil) was added during a ten minute period. Upon completion of addition, the mixture was stirred for twenty minutes. After this time, a solution of 5.8 grams (0.023 mole) of 4-bromobenzyl bromide (available from Aldrich Chemical Company) in 40 mL of THF was added dropwise. Upon completion of addition, the reaction mixture was allowed to warm to ambient temperature where it stirred for seven days. After this time, the reaction mixture was taken up in 100 ml of water. The resulting solution was extracted with two 200 mL portions of diethyl ether. The combined extracts were washed with one 75 mL portion of a 10% aqueous lithium chloride solution, dried with sodium sulfate, and filtered. The filtrate was concentrated under reduced pressure, yielding the crude product. The crude product was triturated with a mixture of diethyl ether and petroleum ether. The resulting solid was collected by filtration, yielding 5.3 grams of the title compound. The NMR spectrum was consistent with the proposed structure.

Step B Compound 362

To a 100 mL roundbottom flask was added 0.02 gram (0.00002 mole) of tris(dibenzylideneacetone)dipalladium (o) (available from Strem Chemical, Newburyport, Mass.), 0.04 gram (0.00006 mole) of racemic 2,2'-bis(diphenylphosphino)-1,1'-binaphthyl (available from Strem Chemical), and 35 mL of toluene. The resulting mixture was evacuated and then backfilled with nitrogen. This evacuation and backfill procedure was repeated two more times. The resulting mixture was stirred at ambient temperature for 30 minutes. After this time, 0.75 gram (0.002 mole) of 5-[(4-bromophenyl)methoxy]-1,2-dichloronaphthalene, 0.52 gram (0.004 mole) of 4-piperidone ethylene ketal (available from Lancaster Synthesis Inc.), and 0.38 gram (0.004 mole) of sodium t-butoxide (available from Aldrich Chemical Company) were added to the 100 mL round bottom flask. Upon completion of addition, the above set forth evacuation and backfill procedure was repeated three times. The reaction mixture was heated to 80–85° C. were it stirred for 4 to 4.5 hours. After this time, the heating was discontinued and the reaction mixture was stirred for about 18 hours. After this time, the reaction mixture was filtered through a celite pad and rinsed with toluene. The filtrate was concentrated under reduced pressure yielding the crude product. The crude product was purified by column chromatography on neutral alumina (deactivated with 6% water), yielding 0.7 gram of title compound. The NMR spectrum was consistent with the proposed structure.

It is well known to one of ordinary skill in the art that the compounds of formula I of the present invention can contain optically-active and racemic forms. It is also well known in the art that the compounds of formula I may contain stereoisomeric forms and/or exhibit polymorphism. It is to be understood that the present invention encompasses any racemic, optically-active, polymorphic or stereoisomeric form, or mixtures thereof. It should be noted that it is well known in the art how to prepare optically-active forms, for example by resolution of a racemic mixture or by synthesis from optically-active starting materials.

Representative compounds prepared by the methods exemplified above are listed in Table 1. Characterizing properties are given in Table 2.

Biological Data

Candidate insecticides are evaluated for activity against the tobacco budworm (*Heliothis virescens* [Fabricius]) in a surface-treated diet test.

In this test one mL of molten (65–70° C.) wheat germ-based artificial diet is pipetted into each well of a four by six (24 well) multi-well plate (ID# 430345-15.5 mm dia.×17.6 mm deep; Corning Costar Corp., One Alewife Center, Cambridge, Mass. 02140). The diet is allowed to cool to ambient temperature before treatment with candidate insecticide.

For a determination of insecticidal activity, solutions of the candidate insecticides are prepared for testing using a Packard 204DT Multiprobe® Robotic System (Packard Instrument Company, 800 Research Parkway, Meriden, Conn. 06450), in which the robot first dilutes a standard 50 millimolar DMSO solution of candidate insecticide with a 1:1 water/acetone solution (V/V) in a ratio of 1:7 stock solution to water/acetone. The robot subsequently pipettes 40 microliters of the so-prepared solution onto the surface of the diet in each of three wells in the 24 multi-well plate. The process is repeated with solutions of seven other candidate insecticides. Once treated, the contents of the multi-well plate are allowed to dry, leaving 0.25 millimoles of candidate insecticide on the surface of the diet, or a concentration of 0.25 millimolar. Appropriate untreated controls containing only DMSO on the diet surface are also included in this test.

For evaluations of the insecticidal activity of a candidate insecticide at varying rates of application, the test is established as described above using sub-multiples of the standard 50 millimolar DMSO solution of candidate insecticide. For example, the standard 50 millimolar solution is diluted by the robot with DMSO to give 5, 0.5, 0.05, 0.005, 0.0005 millimolar, or more dilute solutions of the candidate insecticide. In these evaluations there are six replicates of each rate of application placed on the surface of the diet in the 24 multi-well plate, for a total of four rates of application of candidate insecticide in each plate.

In each well of the test plate is placed one second instar tobacco budworm larvea, each weighing approximately five milligrams. After the larvae are placed in each well, the plate is sealed with clear polyfilm adhesive tape. The tape over each well is perforated to ensure an adequate air supply. The plates are then held in a growth chamber at 25° C. and 60% relative humidity for five days (light 14 hours/day).

After the five-day exposure period insecticidal activity for each rate of application of candidate insecticide is assessed as percent inhibition of insect weight relative to the weight of insects from untreated controls, and percent mortality when compared to the total number of insects infested.

The compounds of the present invention were active in the diet test against the tobacco budworm. Over fifteen of the compounds listed in Table 1 exhibited percent growth inhibition values of 70% or greater. Compounds 224, 353, 354, 355, 357, 364, 366, 367, 368, 369, 372, and 373–379 exhibited percent growth inhibition values of 80% or greater. Table 3 gives the insecticidal activity data for compounds tested in the diet test.

For insecticidal application, the active compounds are formulated into insecticidal compositions by admixture in insecticidally effective amount with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present insecticidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These insecticidal compositions may be applied either as water-diluted sprays, or dusts, or granules to the areas in which insect control is desired. These formulations may contain as little as 0.1%, 0.2% or 0.5% to as much as 95% or more by weight of active ingredient.

Dusts are free flowing admixtures of the active ingredients with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders are in the form of finely divided particles which disperse readily in water or other dispersant. The wettable powder is ultimately applied to the locus where insect control is desired either as a dry dust or as an emulsion in water or other liquid. Typical carriers for wettable powders include Fuller's earth, kaolin clays, silicas, and other highly absorbent, readily wet, inorganic diluents. Wettable powders normally are prepared to contain about 5–80% of active ingredient, depending on the absorbency of the carrier, and usually also contain a small amount of a wetting, dispersing, or emulsifying agent to facilitate dispersion. For example, a useful wettable powder formulation contains 80.8 parts of the insecticidal compound, 17.9 parts of Palmetto clay, and 1.0 part of sodium lignosulfonate and 0.3 part of sulfonated aliphatic polyester as wetting agents. By way of illustration, compound 223 was formulated as a 25% wettable powder (25% WP) as follows:

| COMPONENT | AMOUNT (wt/wt %) |
|---|---|
| Compound 223 (91% pure) | 27.5% |
| Diluent | 5.0% |
| Wetting Agent | 1.0% |
| Dispersing Agent | 16.0% |
| UV Stabilizer | 0.5% |
| Carrier/Diluent | 50.0% |

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isophorone, or other non-volatile organic solvent. For insecticidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing, or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agents, when used, normally comprise from 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as carbon dioxide, propane, or butane, may also be used. Water-soluble or water-dispersible granules are also useful formulations for insecticidal application of the present compounds. Such granular formulations are free-flowing, non-dusty, and readily water-soluble or water-miscible. The soluble or dispersible granular formulations described in U.S. Pat. No. 3,920,442 are useful herein with the present insecticidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active insecticidal compounds of this invention may be formulated and/or applied with other insecticides, fungicides, nematicides, plant growth regulators, fertilizers, or other agricultural chemicals. In using an active compound of this invention, whether formulated alone or with other agricultural chemicals, to control insects, an effective amount and concentration of the active compound is applied to the locus where control is desired. The locus may be, e.g., the insects themselves, plants upon which the insects feed, or the insect habitat. When the locus is the soil, e.g., soil in which agricultural crops have been or will be planted, the composition of the active compound may be applied to and optionally incorporated into the soil. For most applications the effective amount may be as low as, e.g. about 10 to 500 g/ha, preferably about 100 to 250 g/ha.

In a further embodiment of the present invention, several of the compounds disclosed above have themselves been found to be novel and useful intermediates in the preparation of the 1,4-disubstituted benzene insecticides disclosed and claimed herein.

Included among these intermediates are those compounds having the formula XII:

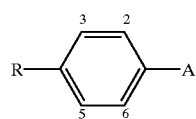

XII wherein:

A is —(CH$_2$)$_n$—U—R$^2$ wherein n is 0 or 1;

U is —C(O)—, —CH$_2$—, oxygen, or —NR$^5$, where R$^5$ is selected from the group consisting of hydrogen, hydroxy, alkyl, sulfonylalkyl, cabonylamino, and carbonylalkyl;

R$^2$ is selected from hydrogen, halo, hydroxy, and 1-R$^4$, wherein:

R$^4$ is

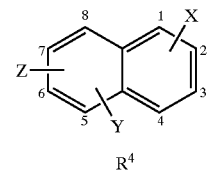

where

X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

R is —T—(CH$_2$)$_m$—R$^1$, where

T is selected from the group consisting of oxygen, nitrogen, and sulfur;

m is 0, 1, 2, 3, or 4;

R$^1$ is hydrogen, halo, alkyl, or —N(R$^8$)(R$^9$); where R$^8$ and R$^9$ are independently selected from the group consisting of hydrogen, alkyl, acetyl, alkoxycarbonyl, alkoxyalkyl, aminoalkyl, carbonylamino, and —(CH$_2$)$_p$—N(R$^{16}$)(R$^{17}$), where p is 1 or 2;

R$^{16}$ and R$^{17}$ are independently selected from the group consisting of hydrogen, alkyl, alkoxyalkyl, and aminoalkyl.

Some preferred intermediates of formula XII are those in which:

n is 1; U is oxygen; R$^2$ is 1-R$^4$, wherein:

R$^4$ is

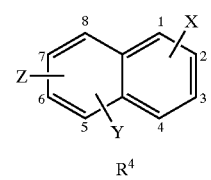

where

X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

T is oxygen or sulfur;

m is 2; and

R$^1$ is halo;

Additional preferred intermediates of formula XII are those in which n is 1; U is —CH$_2$—; R$^2$ is 1-R$^4$, wherein:

$R^4$ is

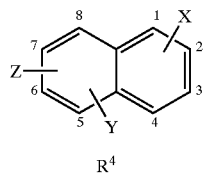

where
X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

T is oxygen;
m is 0; and
$R^1$ is hydrogen or alkyl.

Preferred intermediates of formula XII also include those compounds in which n is 0; U is —C(O); $R^2$ is hydrogen; T is oxygen; m is 2; and $R^1$ is —N($R^8$)($R^9$), where $R^8$ and $R^9$ are alkyl as well as those in which n is 0; U is —CH$_2$—; $R^2$ is halo or hydroxy; T is oxygen; m is 2; and $R^1$ is —N($R^8$)($R^9$); where $R^8$ and $R^9$ are alkyl.

In addition to the compounds set forth above, compounds of formula UU, described generally in Schema 3 above and in greater detail below, have also been found to be novel and useful intermediates in the preparation of the 1,4-disubstituted benzene insecticides disclosed and claimed herein:

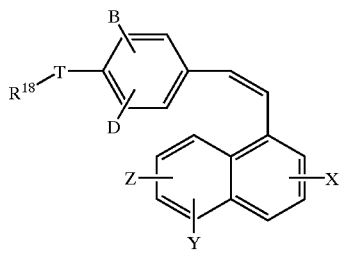

UU where X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy; T is selected from the group consisting of oxygen, nitrogen, and sulfur; and $R^{18}$ is alkyl.

While the invention has been described in detail and with reference to specific embodiments thereof, it will be apparent to one skilled in the art that various changes and modifications can be made therein without departing from the spirit and scope thereof.

TABLE 1

Insecticidal Optionally Substituted Benzenes

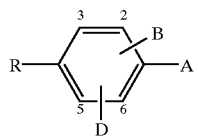

Formula I (FI)
—T—(CH$_2$)$_m$—$R^1$
Formula II (FII)
—(CH$_2$)$_n$—U—$R^2$
Formula III (FIII)

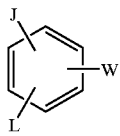

$R^3$

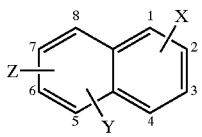

$R^4$

TABLE 1-continued

Insecticidal Optionally Substituted Benzenes

Formula I
A and D are H; R is FII; T is O; m is 2; R¹ is N(C₂H₅)₂

| Cmpnd No. | B | n | U | R² | X | Y | Z |
|---|---|---|---|---|---|---|---|
| 1 | 2-FIII | 1 | N | 1-R⁴ | 4-Cl | H | H |
| 2 | 3-FIII | 1 | N | 1-R⁴ | 4-Cl | H | H |

Formula I
B and D are H; R is FII; T is O; m is 2; R¹ is N(C₂H₅)₂

| Cmpnd No. | A |
|---|---|
| 3 | |
| 4 | |
| 5 | |
| 6 | |
| 7 | |

TABLE 1-continued
Insecticidal Optionally Substituted Benzenes
Formula I
A is FIII; B and D are H; R is FII; T is O; m is 2; $R^1$ is $N(C_2H_5)_2$; n is 1
| Cmpnd No. | U | $R^2$ |
|---|---|---|
| 8 | O | 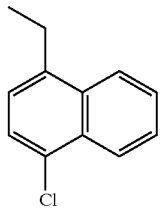 |
| 9 | O | 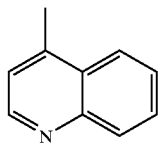 |
| 10 | O | 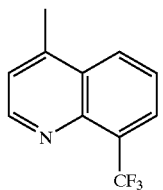 |
| 11 | O | 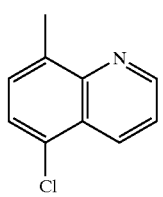 |
| 12 | O | 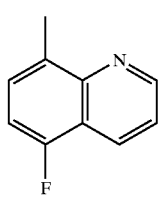 |
| 13 | N | 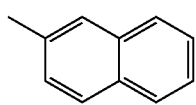 |
| 14 | N | 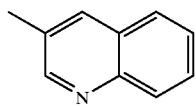 |
| 15 | N | 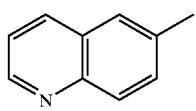 |

TABLE 1-continued

Insecticidal Optionally Substituted Benzenes

| 16 | N | 1-methylisoquinoline |
| 17 | N | 4-chloro-2,2,7-trimethyl-2,3-dihydrobenzofuran |
| 18 | N | 2-chloro-5-methylpyridine |
| 19 | N | 7-chloro-2-isopropyl-4-methylisoindolin-1-one |
| 20 | N | 5-chloro-8-methyl-1,2,3,4-tetrahydronaphthalene |
| 21 | O | 2-methyldibenzofuran |
| 22 | O | 4-methylquinazoline |
| 23 | O | 8-chloro-4-methylquinazoline |

TABLE 1-continued
Insecticidal Optionally Substituted Benzenes
| 24 | O | 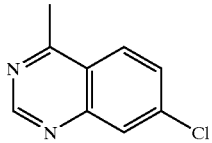 |
| 25 | O | 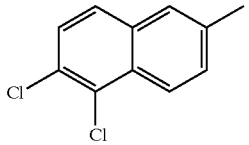 |
| 26 | O | 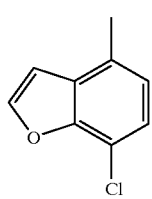 |
| 27 | O | 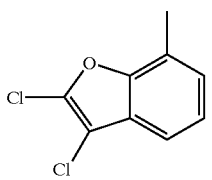 |
| 28 | O | 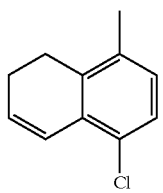 |
| 29 | O | 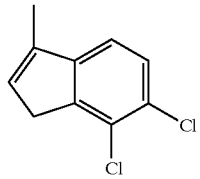 |
| 30 | O | 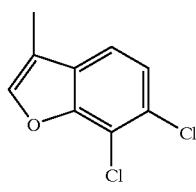 |
| 31 | O | 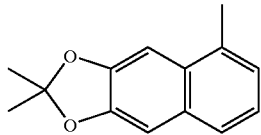 |

TABLE 1-continued
Insecticidal Optionally Substituted Benzenes
| | | |
|---|---|---|
| 32 | O | 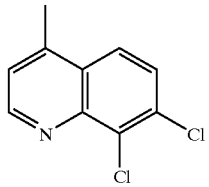 |
| 33 | O | 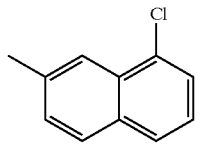 |
| 34 | O | 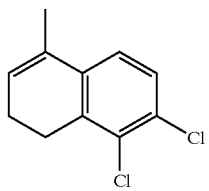 |
| 35 | O | 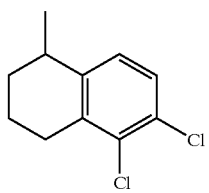 |
| 36 | O | 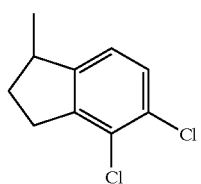 |
| 37 | O | 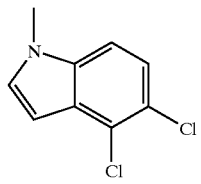 |
| 38 | N | 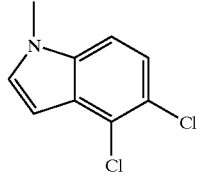 |
| 38 | O | 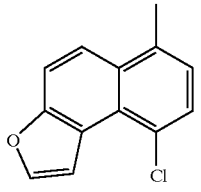 |

TABLE 1-continued

Insecticidal Optionally Substituted Benzenes

Formula I
A is FIII; B and D are H; n is 1; U is N; $R^2$ is 1-$R^4$; X is 4-Cl; Y and Z are H

| Cmpnd No. | R |
|---|---|
| 39 | —N($C_2H_5$)$_2$ |
| 40 | CH$_3$-N(C(=O)CH$_3$)-CH$_2$CH$_2$-N($C_2H_5$)$_2$ |
| 41 | CH$_3$-N(C(=O)O-C(CH$_3$)$_3$)-CH$_2$CH$_2$-N($C_2H_5$)$_2$ |
| 42 | CH$_3$-NH-CH$_2$CH$_2$-N($C_2H_5$)$_2$ |

Formula I
A is FIII; B and D are H; R is FII; T is O; n is 0; $R^2$ is 1-$R^4$; Y and Z are H

| Cmpnd No. | m | $R^1$ | U | X |
|---|---|---|---|---|
| 43 | 0 | $CH_3$ | $C_2H_4$ | 4-Br |
| 44 | 0 | $CH_3$ | —N(C(=O))N— | 4-Cl |
| 45 | 1 | 1-$C_6H_5$ | —O$C_2H_4$O— | 4-Cl |
| 46 | 1 | —C(=O)—N($C_2H_5$)$_2$ | —CH=N— | 4-Cl |
| 47 | 2 | N($C_2H_5$)$_2$ | —O$C_2H_4$O— | 4-Cl |
| 48 | 2 | N($C_2H_5$)$_2$ | —N(C(=O))N— | 4-Cl |
| 49 | 2 | N($C_2H_5$)$_2$ | —NH$C_2H_4$— | 4-Cl |
| 50 | 2 | N($C_2H_5$)$_2$ | O$CH_2$ | 4-Cl |
| 51 | 2 | N($C_2H_5$)$_2$ | O | 4-Cl |
| 52 | 2 | N($C_2H_5$)$_2$ | $CH_2$ | 4-Cl |
| 53 | 2 | N($C_2H_5$)$_2$ | $SO_2$ | 4-Cl |
| 54 | 2 | N($C_2H_5$)$_2$ | CO | 4-Cl |
| 55 | 2 | N($C_2H_5$)$_2$ | $CF_2$ | 4-Cl |
| 56 | 2 | N($C_2H_5$)$_2$ | —CH(OH) | 4-Cl |
| 57 | 2 | N($C_2H_5$)$_2$ | —$CH_2$S— | 4-Cl |
| 58 | 2 | N($C_2H_5$)$_2$ | $CH_2$SO | 4-Cl |
| 59 | 2 | N($C_2H_5$)$_2$ | $CH_2SO_2$ | 4-Cl |
| 60 | 2 | —O$C_2H_5$ | —$CH_2$NH— | 4-Cl |

TABLE 1-continued

Insecticidal Optionally Substituted Benzenes

Formula I
A is FIII; B and D are H; R is FII; T is O; m is 1; n is 1; R² is 1-R⁴; X is 4-Cl; Y and Z are H

| Cmpnd No. | U | R¹ |
|---|---|---|
| 61 | O | —CH₂=C(Cl)₂ |
| 62 | N | —C(O)O |
| 63 | N | 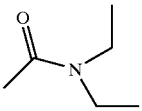 |

Formula I
A is FIII; B and D are H; R is FII; n is 1; R² is 1-R⁴;

| Cmpnd No. | m | T | U | R¹ | X | Y | Z |
|---|---|---|---|---|---|---|---|
| 64 | 1 | O | N | —CH₃ | 4-Cl | H | H |
| 65 | 1 | O | N | —CH₂F | 4-Cl | H | H |
| 66 | 1 | O | O | 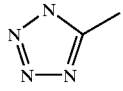 | 4-Cl | H | H |
| 67 Hydrochloride Salt | 1 | O | O | 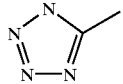 | 4-Cl | H | H |
| 68 | 1 | O | O | 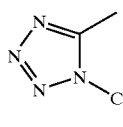 | 4-Cl | H | H |
| 69 | 1 | O | O | 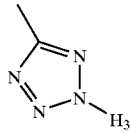 | 4-Cl | H | H |
| 70 | 1 | O | O | 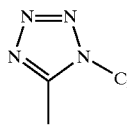 | 4-Cl | H | H |
| 71 | 2 | S | N | —N(C₂H₅)₂ | 4-Cl | H | H |
| 72 | 2 | O | CH₂ | —N(C₂H₅)₂ | 4-Br | H | H |
| 73 | 2 | O | CH₂ | —N(C₂H₅)₂ | 4-Cl | H | H |
| 74 | 2 | O | N | —N(CH₃)₂ | H | H | H |
| 75 | 2 | O | N | —N(C₂H₅)₂ | H | H | H |
| 76 | 2 | O | N | 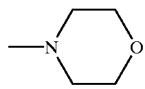 | H | H | H |
| 77 | 2 | O | N | —N(CH₃)₂ | 4-Br | H | H |
| 78 | 2 | O | N | —N(C₂H₅)₂ | 4-Br | H | H |
| 79 | 2 | O | N | —N(isopropyl)₂ | 4-Br | H | H |
| 80 | 2 | O | N | 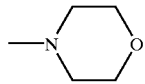 | 4-Br | H | H |

TABLE 1-continued
Insecticidal Optionally Substituted Benzenes
| | | | | | | | |
|---|---|---|---|---|---|---|---|
| 81 | 2 | O | N | 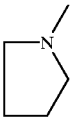 | 4-Br | H | H |
| 82 | 2 | O | N | —NH(C$_2$H$_5$) | 4-Cl | H | H |
| 83 | 2 | O | N | —N(CH$_3$)$_2$ | 4-Cl | H | H |
| 84 | 2 | O | N | —N(C$_2$H$_5$)$_2$ | 4-Cl | H | H |
| 85 Chloride Salt | 2 | O | N | —N(C$_2$H$_5$)$_2$ | 4-Cl | H | H |
| 86 | 2 | O | N | —N(C$_2$H$_5$)$_2$ | 8-Cl | H | H |
| 87 | 2 | O | N | —N(isopropyl)$_2$ | 4-Cl | H | H |
| 88 | 2 | O | N | —N(C$_4$H$_9$)$_2$ | 4-Cl | H | H |
| 89 | 2 | O | N |  | 4-Cl | H | H |
| 90 | 2 | O | N | 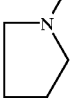 | 4-Cl | H | H |
| 91 | 2 | O | N | 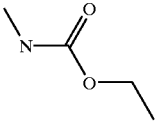 | 4-Cl | H | H |
| 92 | 2 | O | N | 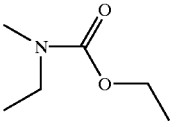 | 4-Cl | H | H |
| 93 | 2 | O | N | 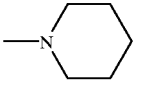 | 4-Cl | H | H |
| 94 | 3 | O | N | —N(CH$_3$)$_2$ | 4-Cl | H | H |
| 95 | 3 | O | N | —N(C$_4$H$_9$)$_2$ | 4-Cl | H | H |
| 96 | 3 | O | N | 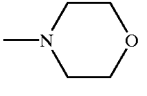 | 4-Cl | H | H |
| 97 | 4 | O | N | —N(C$_4$H$_9$)$_2$ | 4-Cl | H | H |
| 98 | 2 | O | O | 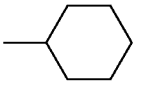 | 4-Cl | H | H |
| 99 | 2 | O | O | 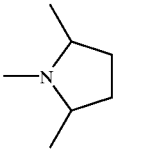 | 4-Cl | H | H |
| 100 | 2 | O | O | 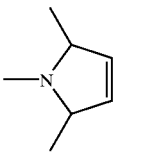 | 4-Cl | H | H |

TABLE 1-continued
Insecticidal Optionally Substituted Benzenes
| | | | | | | | |
|---|---|---|---|---|---|---|---|
| 101 | 2 | O | O | 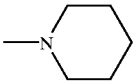 | 4-Cl | H | H |
| 102 | 2 | O | O | 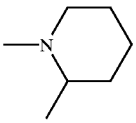 | 4-Cl | H | H |
| 103 | 2 | O | O | 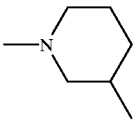 | 4-Cl | H | H |
| 104 | 2 | O | O |  | 4-Cl | H | H |
| 105 | 2 | O | O | 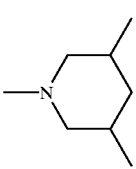 | 4-Cl | H | H |
| 106 | 2 | O | O | 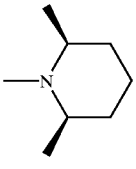 | 4-Cl | H | H |
| 107 | 2 | O | O | 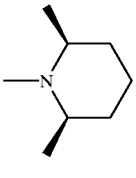 | 4-Cl | 6-Cl | H |
| 108 | 2 | O | O | 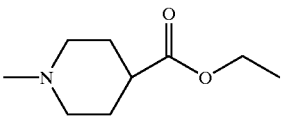 | 4-Cl | H | H |
| 109 | 2 | O | O | 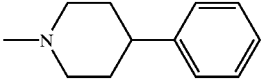 | 4-Cl | H | H |
| 110 | 2 | O | O | 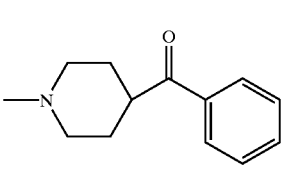 | 4-Cl | H | H |
| 111 | 2 | O | O | 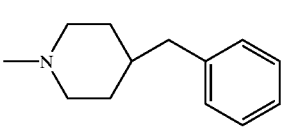 | 4-Cl | H | H |

TABLE 1-continued
Insecticidal Optionally Substituted Benzenes
| | | | | | | | |
|---|---|---|---|---|---|---|---|
| 112 | 2 | O | O | 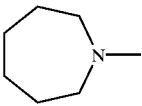 | 4-Cl | H | H |
| 113 | 2 | O | O | 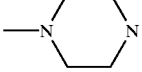 | 4-Cl | H | H |
| 114 | 2 | O | O | 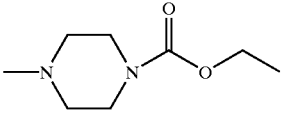 | 4-Cl | H | H |
| 115 | 2 | O | O | 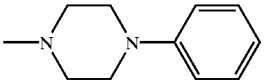 | 4-Cl | H | H |
| 116 | 2 | O | O | 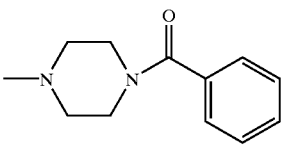 | 4-Cl | H | H |
| 117 | 2 | O | O | 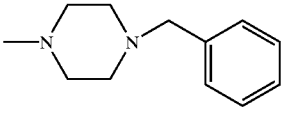 | 4-Cl | H | H |
| 118 | 2 | O | O | 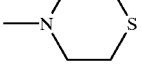 | 4-Cl | H | H |
| 119 | 2 | O | O | 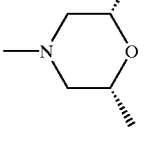 | 4-Cl | H | H |
| 120 | 2 | O | O | 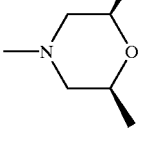 | 4-Cl | H | H |
| 121 | 2 | O | O | 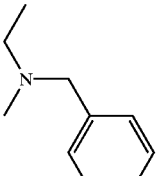 | 4-Cl | H | H |
| 122 | 2 | O | O | 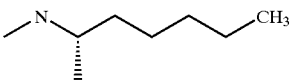 | 4-Cl | H | H |

TABLE 1-continued
Insecticidal Optionally Substituted Benzenes
| | | | | | | | |
|---|---|---|---|---|---|---|---|
| 123 | 2 | O | O | 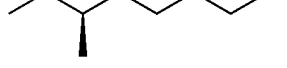 | 4-Cl | H | H |
| 124 | 2 | O | O | 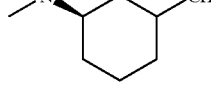 | 4-Cl | H | H |
| 125 | 2 | O | O | 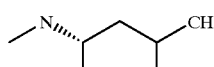 | 4-Cl | H | H |
| 126 | 2 | O | O | 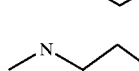 | 4-Cl | H | H |
| 127 | 2 | O | O | 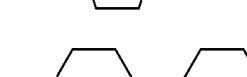 | 4-Cl | H | H |
| 128 | 2 | O | O | 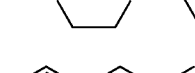 | 4-Cl | H | H |
| 129 | 2 | O | O | 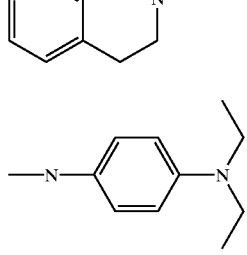 | 4-Cl | H | H |
| 130 | 2 | O | O | 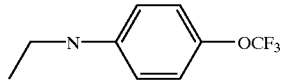 | 4-Cl | H | H |
| 131 | 2 | O | O | 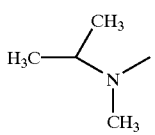 | 4-Cl | H | H |
| 132 | 2 | O | O | 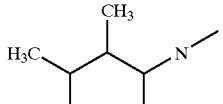 | 4-Cl | H | H |
| 133 | 2 | O | O | 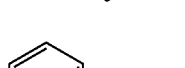 | 4-Cl | H | H |
| 134 | 2 | O | O | 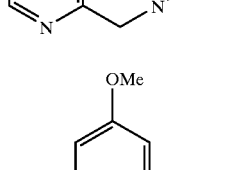 | 4-Cl | H | H |

TABLE 1-continued
Insecticidal Optionally Substituted Benzenes
| 135 | 2 | O | O | 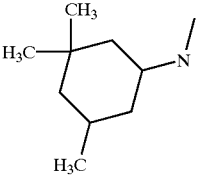 | 4-Cl | H | H |
| 136 | 2 | O | O | 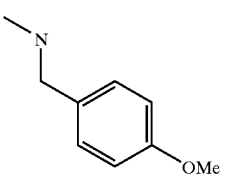 | 4-Cl | H | H |
| 137 | 2 | O | O | 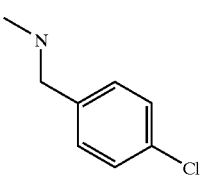 | 4-Cl | H | H |
| 138 | 2 | O | O | 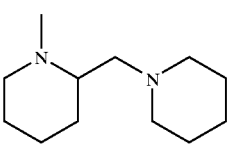 | 4-Cl | H | H |
| 139 | 2 | O | O | 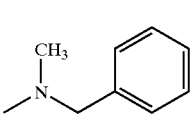 | 4-Cl | H | H |
| 140 | 2 | O | O | 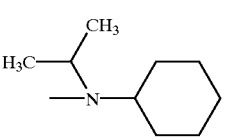 | 4-Cl | H | H |
| 141 | 2 | O | O | 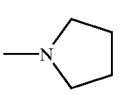 | 4-Cl | H | H |
| 142 | 2 | O | O | 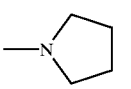 | 5-Cl | 6-Cl | H |
| 143 | 2 | O | O | 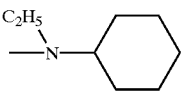 | 4-Cl | H | H |
| 144 | 2 | O | O | 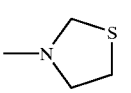 | 4-Cl | H | H |

TABLE 1-continued

Insecticidal Optionally Substituted Benzenes

| # | | | | Structure | X | Y | Z |
|---|---|---|---|---|---|---|---|
| 145 | 2 | O | O | N-methyl-N-allyl-cyclohexylamine | 4-Cl | H | H |
| 146 | 2 | O | O | N,N-dimethyl-cyclohexylamine | 4-Cl | H | H |
| 147 | 2 | O | O | N-methyl-N-(cyclopropylmethyl)-propylamine | 4-Cl | H | H |
| 148 | 2 | O | O | N-methyl-azocane | 4-Cl | H | H |
| 149 | 2 | O | O | 2-methyl-2,3,4,9-tetrahydro-1H-β-carboline | 4-Cl | H | H |
| 150 | 2 | O | O | 1-methyl-2,5-dihydro-1H-pyrrole | 4-Cl | H | H |
| 151 | 2 | O | O | N-methyl-tryptamine | 4-Cl | H | H |
| 152 | 2 | O | O | 5-methoxy-N-methyl-tryptamine | 4-Cl | H | H |
| 153 | 2 | O | O | 1-methyl-4-(2-methoxyphenyl)-piperazine | 4-Cl | H | H |

TABLE 1-continued
Insecticidal Optionally Substituted Benzenes
| | | | | | | | |
|---|---|---|---|---|---|---|---|
| 154 | 2 | O | O | 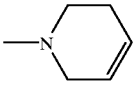 | 4-Cl | H | H |
| 155 | 2 | O | O | 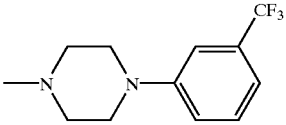 | 4-Cl | H | H |
| 156 | 2 | O | O | 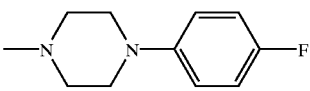 | 4-Cl | H | H |
| 157 | 2 | O | O | 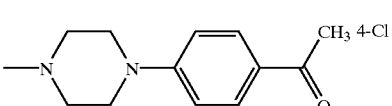 | 4-Cl | H | H |
| 158 | 2 | O | O | 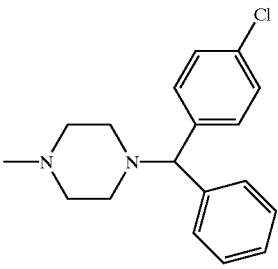 | 4-Cl | H | H |
| 159 | 2 | O | O | 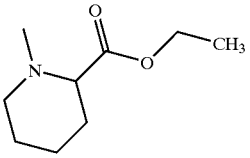 | 4-Cl | H | H |
| 160 | 2 | O | O | 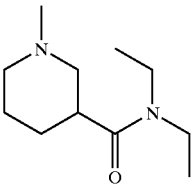 | 4-Cl | H | H |
| 161 | 2 | O | O | 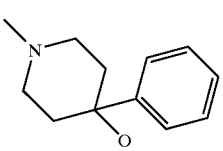 | 4-Cl | H | H |
| 162 | 2 | O | O | 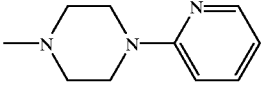 | 4-Cl | H | H |
| 163 | 2 | O | O | 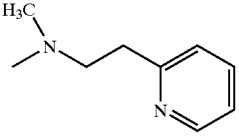 | 4-Cl | H | H |

US 6,753,429 B2
TABLE 1-continued
Insecticidal Optionally Substituted Benzenes
| 164 | 2 | O | O | 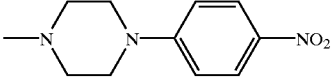 | 4-Cl | H | H |
| 165 | 2 | O | O | 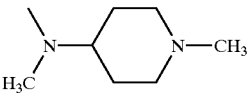 | 4-Cl | H | H |
| 166 | 2 | O | O | 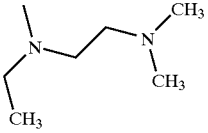 | 4-Cl | H | H |
| 167 | 2 | O | O | 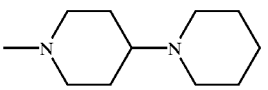 | 4-Cl | H | H |
| 168 | 2 | O | O | 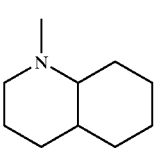 | 4-Cl | H | H |
| 169 | 2 | O | O | 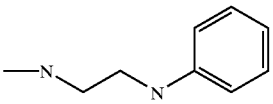 | 4-Cl | H | H |
| 170 | 2 | O | O | 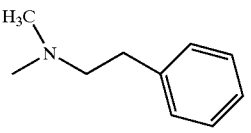 | 4-Cl | H | H |
| 171 | 2 | O | O | 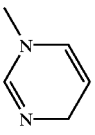 | 4-Cl | H | H |
| 172 | 2 | O | O | 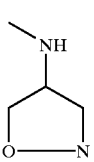 | 4-Cl | H | H |
| 173 | 2 | O | O | 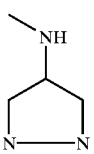 | 4-Cl | H | H |
| 174 | 2 | O | O | 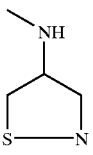 | 4-Cl | H | H |

TABLE 1-continued

Insecticidal Optionally Substituted Benzenes

| 175 | 2 O O | 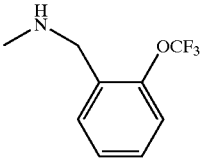 | 4-Cl | H | H |
| 176 | 2 O O | 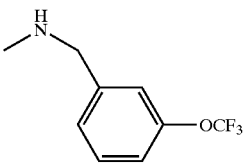 | 4-Cl | H | H |
| 177 | 2 O O | —OC$_4$H$_9$ | 4-Cl | H | H |
| 178 | 2 O O | —N(C$_2$H$_5$)(OCH$_3$) | 4-Cl | H | H |
| 179 | 2 O O | —N(C$_2$H$_5$)$_2$(OCH$_3$) | 4-Cl | H | H |
| 180 | 2 O O | —NHC$_6$H$_5$ | 4-Cl | H | H |
| 181 | 2 O O | 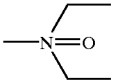 | 4-Cl | 6-Cl | H |
| 182 Hydrochloride Salt | 2 O O | 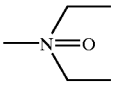 | 4-Cl | 6-Cl | H |
| 183 | 2 O O | 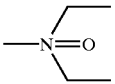 | 5-Cl | 6-Cl | H |
| 184 | 2 O O | —NH(C$_2$H$_5$) | 4-Cl | H | H |
| 185 Hydrochloride Salt | 2 O O | —NH(C$_2$H$_5$) | 4-Cl | H | H |
| 186 | 2 O O | —N(C$_2$H$_5$)$_2$ | 2-Cl | H | H |
| 187 | 2 O O | —N(C$_2$H$_5$)$_2$ | 3-Cl | H | H |
| 188 | 2 O O | —N(C$_2$H$_5$)$_2$ | 4-Cl | H | H |
| 189 Chloride Salt | 2 O O | —N(C$_2$H$_5$)$_2$ | 4-Cl | H | H |
| 190 Iodide Salt | 2 O O | —N(C$_2$H$_5$)(CH$_3$)$_2$ | 4-Cl | H | H |
| 191 | 2 O O | —N(CH$_2$CN(C$_2$H$_5$) | 4-Cl | H | H |
| 192 | 2 O O | —N(C$_2$H$_5$)(CH$_3$) | 4-Cl | H | H |
| 193 Hydrochloride Salt | 2 O O | —N(C$_2$H$_5$)(CH$_3$) | 4-Cl | H | H |
| 194 | 2 O O | —NHtBu | 4-Cl | H | H |
| 195 | 2 O O | —N(C$_3$H$_6$)(OC$_2$H$_5$) | 4-Cl | H | H |
| 196 | 2 O O | —N(CH$_2$CH=CH$_2$)$_2$ | 4-Cl | H | H |
| 197 | 2 O O | —NCH$_2$C(OCH$_3$)$_2$ | 4-Cl | H | H |
| 198 | 2 O O | —NC$_3$H$_6$OCH$_3$ | 4-Cl | H | H |
| 199 | 2 O O | —NC$_4$H$_9$ | 4-Cl | H | H |
| 200 | 2 O O | —N(CH$_3$)C$_2$H$_4$CN | 4-Cl | H | H |
| 201 | 2 O O | —N(C$_2$H$_5$)C$_4$H$_9$ | 4-Cl | H | H |
| 202 | 2 O O | —N(C$_4$H$_9$)$_2$ | 4-Cl | H | H |
| 203 | 2 O O | —N(isopropyl)$_2$ | 4-Cl | H | H |
| 204 | 2 O O | —N(C$_6$H$_{13}$)$_2$ | 4-Cl | H | H |
| 205 | 2 O O | —N(CH$_3$)C$_{17}$H$_{35}$ | 4-Cl | H | H |
| 206 | 2 O O | —N(C$_2$H$_5$)$_2$ | 5-Cl | H | H |
| 207 | 2 O O | —N(C$_2$H$_5$)$_2$ | 6-Cl | H | H |
| 208 | 2 O O | —N(C$_2$H$_5$)$_2$ | 7-Cl | H | H |
| 209 | 2 O O | —N(C$_2$H$_5$)$_2$ | 8-Cl | H H | |
| 210 | 2 O O | —N(C$_2$H$_5$)$_2$ | 2-Cl | 4-Cl | H |
| 211 | 2 O O | —N(C$_2$H$_5$)$_2$ | 2-Cl | 5-Cl | H |
| 212 | 2 O O | —N(C$_2$H$_5$)$_2$ | 2-Cl | 6-Cl | H |
| 213 | 2 O O | —N(C$_2$H$_5$)$_2$ | 2-Cl | 8-Cl | H |
| 214 | 2 O O | —N(C$_2$H$_5$)$_2$ | 4-Cl | 5-Cl | 6-Cl |
| 215 | 2 O O | —N(C$_2$H$_5$)$_2$ | 4-Cl | 5-Cl | H |
| 216 | 2 O O | —N(C$_2$H$_5$)$_2$ | 4-Cl | 6-Cl | H |
| 217 | 2 O O | —N(C$_2$H$_5$)$_2$ | 4-Cl | 6-Cl | H |

TABLE 1-continued

Insecticidal Optionally Substituted Benzenes

| | | | | | | | |
|---|---|---|---|---|---|---|---|
| Chloride Salt | | | | | | | |
| 218 | 2 | O | O | —N(C$_2$H$_5$)$_2$ | 4-Cl | 6-Cl | H |
| Sulfonic Salt | | | | | | | |
| 219 | 2 | O | O | —N(C$_2$H$_5$)$_2$ | 4-Cl | 6-Cl | H |
| Trifluoroacetic Salt | | | | | | | |
| 220 | 2 | O | O | —N(C$_2$H$_5$)$_2$ | 4-Cl | 6-Cl | H |
| Methylbenzene-sulfonic Salt | | | | | | | |
| 221 | 2 | O | O | —N(C$_2$H$_5$)$_2$ | 4-Cl | 7-Cl | H |
| 222 | 2 | O | O | —N(C$_2$H$_5$)$_2$ | 4-Cl | 8-Cl | H |
| 223 | 2 | O | O | —N(C$_2$H$_5$)$_2$ | 5-Cl | 6-Cl | H |
| 224 | 2 | O | O | —N(C$_2$H$_5$)$_2$ | 5-Cl | 6-Cl | H |
| Chloride Salt | | | | | | | |
| 225 | 2 | O | O | —N(C$_2$H$_5$)$_2$ | 5-Cl | 6-Cl | H |
| Phosphoric salt | | | | | | | |
| 226 | 2 | O | O | —NHtBu | 5-Cl | 6-Cl | H |
| 227 | 2 | O | O | —N(C$_2$H$_5$)$_2$ | 6-Cl | 8-Cl | H |
| 228 | 2 | O | O | —N(C$_2$H$_5$)$_2$ | 4-Br | H | H |
| 229 | 2 | O | O | —N(C$_2$H$_5$)$_2$ | 6-Br | H | H |
| 230 | 2 | O | O | —N(C$_2$H$_5$)$_2$ | 5-Br | H | H |
| 231 | 2 | O | O | —N(C$_2$H$_5$)$_2$ | 4-F | H | H |
| 232 | 2 | O | O | —N(C$_2$H$_5$)$_2$ | 4-CF$_3$ | H | H |
| 233 | 2 | O | O | —N(C$_2$H$_5$)$_2$ | 6-CF$_3$ | H | H |
| 234 | 2 | O | O | —N(C$_2$H$_5$)$_2$ | 4-N$_3$ | H | H |
| 235 | 2 | O | O | —N(C$_2$H$_5$)$_2$ | 4-OCH$_3$ | H | H |
| 236 | 2 | O | O | —N(C$_2$H$_5$)$_2$ | 4-OCH$_3$ | H | H |
| Chloride Salt | | | | | | | |
| 237 | 2 | O | O | —N(C$_2$H$_5$)$_2$ | 5-OCH$_3$ | H | H |
| 238 | 2 | O | O | —N(C$_2$H$_5$)$_2$ | 4-NO$_2$ | H | H |
| 239 | 2 | O | O | —N(C$_2$H$_5$)$_2$ | 4-CN | H | H |
| 240 | 2 | O | O | —N(C$_2$H$_5$)$_2$ | 2-CH$_3$ | H | H |
| 241 | 2 | O | O | —N(C$_2$H$_5$)$_2$ | 6-CH$_3$ | | H H |
| 242 | 2 | O | O | —N(C$_2$H$_5$)$_2$ | —⟨C$_6$H$_4$⟩—F | H | H |
| 243 | 2 | O | O | —N(C$_2$H$_5$)$_2$ | —O—⟨C$_6$H$_4$⟩—Cl | H | H |
| 244 | 2 | O | O | —N(C$_2$H$_5$)$_2$ | 5-Cl | 6-CF$_3$ | H |
| 245 | 2 | O | O | —N(C$_2$H$_5$)$_2$ | 5-Cl | 6-Br | H |
| 246 | 2 | O | O | —N(C$_2$H$_5$)$_2$ | 5-Cl | 6-I | H |
| 247 | 2 | O | O | —N(C$_2$H$_5$)$_2$ | 5-I | 6-Cl | H |
| 248 | 2 | O | O | —N(C$_2$H$_5$)$_2$ | 5-Cl | 6-OCF$_3$ | H |
| 249 | 2 | O | O | —N(C$_2$H$_5$)$_2$ | 5-Cl | 6-CN | H |
| 250 | 2 | O | O | —N(C$_2$H$_5$)$_2$ | 5-Cl | 6-NO$_2$ | H |
| 251 | 2 | O | O | —N(C$_2$H$_5$)$_2$ | 5-CF$_3$ | 6-Cl | H |
| 252 | 2 | O | O | —N(C$_2$H$_5$)$_2$ | 5-OCH$_3$ | 6-Cl | H |
| 253 | 2 | O | O | —N(C$_2$H$_5$)$_2$ | 4-CF$_3$ | 6-Cl | H |
| 254 | 2 | O | O | (2,6-dimethylpiperidin-1-yl) | 5-Cl | 6-Cl | H |
| 255 | 2 | O | CH$_2$ | (2,6-dimethylpiperidin-1-yl) | 5-Cl | 6-Cl | H |
| 256 | 2 | O | O | (piperidin-1-yl) | 5-Cl | 6-Cl | H |

TABLE 1-continued

Insecticidal Optionally Substituted Benzenes

| 257 | 2 | O | S    | —N(C$_2$H$_5$)$_2$ | 5-Cl | 6-Cl | H |
| --- | - | - | ---- | ------------------ | ---- | ---- | - |
| 258 | 2 | O | SO$_2$ | —N(C$_2$H$_5$)$_2$ | 5-Cl | 6-Cl | H |
| 259 | 3 | O | O    | —N(C$_2$H$_5$)$_2$ | 4-Cl | H    | H |
| 260 | 4 | O | O    | —N(C$_2$H$_5$)$_2$ | 4-Cl | H    | H |

Please note that Compound No. 261 is a mixture of Compound 212 and (2-(4-((2,4,6-trichloronaphthyloxy)phenoxy)ethyl) diethylamine.

Formula I
A is FIII; R is FII; T is O; m is 2; R$^1$ is —N(C$_2$H$_5$)$_2$; R$^2$ is 1-R$^4$; X is 4-Cl; Y and Z are H

| Cmpnd No. | B | D | n | U |
| --- | --- | --- | --- | --- |
| 262 | 2-F | H | 1 | N |
| 263 | 2-OCH$_3$ | H | 1 | N |
| 264 | 4-OCH$_3$ | H | 1 | N |
| 265 | 3-OCH$_3$ | 5-OCH$_3$ | 1 | N |
| 266 | 5-(OC$_2$H$_4$N(C$_2$H$_5$)$_2$) | H | 1 | N |
| 267 | 2-Cl | H | 1 | N |
| 268 | 3-Cl | H | 1 | N |
| 269 | 2-Cl | 3-Cl | 1 | N |
| 270 | 2-Cl | 6-Cl | 1 | N |
| 271 | 3-Cl | 5-Cl | 1 | N |
| 272 | 3-Cl | 5-Cl | 0 | —C(=O)—N(CH$_3$)— |

Formula I
A and D are H; R is FII; T is O; m is 2; R$^1$ is N(C$_2$H$_5$)$_2$

| Cmpnd No. | B | n | U | R$^2$ | J | L | W |
| --- | --- | --- | --- | --- | --- | --- | --- |
| 273 | 5-FIII | 1 | N | 1-R$^3$ | 4-Cl | H | H |
| 274 | 6-FIII | 1 | N | 1-R$^3$ | 4-Cl | H | H |

Formula I
A is FIII; B and D are H; R is FII; T is O; m is 2; n is 1; U is O

| Cmpnd No. | R$^1$ | R$^2$ |
| --- | --- | --- |
| 275 | 4-methylpiperazin-1-yl | 4-chlorophenyl |
| 276 | 4-(tert-butoxycarbonyl)piperazin-1-yl (N-methyl) | 4-chlorophenyl |
| 277 | —N(C$_2$H$_5$)$_2$ | 2-chloro-6-ethylphenyl |

Formula I
A is FIII; B and D are H; R is FII; m is 2; T is O; R$^1$ is —N(C$_2$H$_5$)$_2$; n is 1; R$^2$ is 1-R$^3$;

| mpnd No. | U | J | L | W |
| --- | --- | --- | --- | --- |
| 278 | N | H | H | H |
| 279 | N | 2-OCF$_3$ | H | H |
| 280 | N | 4-OCF$_3$ | H | H |
| 281 | N | 2-OC$_2$H$_5$ | H | H |
| 282 | N | 3-OC$_6$H$_5$ | H | H |
| 283 | N | 2-Cl | H | H |
| 284 | N | 4-Cl | H | H |
| 285 | N | 2-Cl | 3-Cl | H |
| 286 | N | 2-Cl | 3-Cl | 4-Cl |
| 287 | N | 2-Cl | 4-Cl | H |
| 288 | N | 2-Cl | 4-Cl | 5-Cl |
| 289 | N | 3-Cl | 4-Cl | H |

TABLE 1-continued

Insecticidal Optionally Substituted Benzenes

| | | | | |
|---|---|---|---|---|
| 290 | N | 3-Cl | 5-Cl | H |
| 291 | N | 2-C$_6$H$_5$ | H | H |
| 292 | N | 2-C$_6$H$_5$ | 4-Cl | H |
| 293 | N | 3-C$_6$H$_5$ | 4-Cl | H |
| 294 | N | 2-F | 3-F | H |
| 295 | N | 2-F | 3-F | 4-F |
| 296 | N | 2-F | 4-F | H |
| 297 | N | 2-F | 4-F | 5-F |
| 298 | N | 2-CH$_3$ | 3-CH$_3$ | H |
| 299 | N | 2-CH$_3$ | 4-CH$_3$ | H |
| 300 | N | 2-OCH$_3$ | 4-OCH$_3$ | H |
| 301 | N | 2-OCH$_3$ | 5-OCH$_3$ | H |
| 302 | N | 3-OCH$_3$ | 5-OCH$_3$ | H |
| 303 | O | 3-OCH$_3$ | 5-OCH$_3$ | H |
| 304 | O | H | H | H |
| 305 | O | 2-Cl | H | H |
| 306 | O | 4-Cl | H | H |
| 307 | O | 2-Cl | 3-Cl | H |
| 308 | O | 2-Cl | 3-Cl | 4-Cl |
| 309 | O | 2-Cl | 4-Cl | H |
| 310 | O | 2-Cl | 4-Cl | 5-Cl |
| 311 | O | 2-Cl | 5-Cl | H |
| 312 | O | 2-Cl | 6-Cl | H |
| 313 | O | 3-Cl | 4-Cl | H |
| 314 | O | 3-Cl | 5-Cl | H |
| 315 | O | 2-Cl | 4-Br | H |
| 316 | O | 2-Cl | 6-Br | H |
| 317 | O | 2-Cl | 5-CH$_3$ | H |
| 318 | O | 2-C(CH$_3$)$_3$ | H | H |
| 319 | O | 3-C(CH$_3$)$_3$ | H | H |
| 320 | O | 4-C(CH$_3$)$_3$ | H | H |
| 321 | O | 2-isopropyl | H | H |
| 322 | O | 4-C$_3$H$_7$ | H | H |
| 323 | O | 4-OCH$_3$ | H | H |
| 324 | O | 4-OCF$_3$ | H | H |
| 325 | O | 2-CN | H | H |
| 326 | O | 5-CN | H | H |
| 327 | O | 2-NC(O)CH$_3$ | H | H |
| 328 | O | 2-C(O)OC$_2$H$_5$ | H | H |
| 329 | O | 4-C(O)CH$_3$ | H | H |
| 330 | O | 2-C(O)CH$_3$ | 3-OCH$_3$ | H |
| 331 | O | 2-C(O)CH$_3$ | 4-OCH$_3$ | H |
| 332 | O | 2-CH$_3$ | 4-Cl | H |
| 333 | O | 3-CH$_3$ | 4-Cl | H |
| 334 | O | 2-NO$_2$ | 4-Cl | H |
| 335 | O | 2-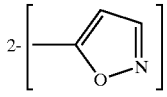 | 4-Cl | H |
| 336 | O | 2-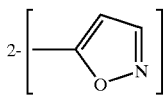 | 4-Cl | 5-CH$_3$ |
| 337 | O | 2-CH$_3$ | 4-CH$_3$ | H |
| 338 | O | 2-CH$_3$ | 3-CH$_3$ | 5-CH$_3$ |
| 339 | O | 2-CH$_3$ | 3-CH$_3$ | 6-CH$_3$ |
| 340 | O | 2-OCH$_3$ | 4-CH$_3$ | H |
| 341 | O | 2-Br | 4-Br | H |
| 342 | O | 2-Br | 6-Br | H |
| 343 | O | 2-Br | 4-CH$_3$ | H |
| 344 | O | 2-Br | 4-CH$_3$ | 6-Br |
| 345 | O | 2-F | 3-F | H |
| 346 | O | 2-F | 5-F | H |
| 347 | O | 2-F 6-F | H | |
| 348 | O | 3-F | 5-F | H |
| 349 | O | 4-F | 6-F | H |
| 350 | O | 3-F 4-F | 6-F | |
| 351 | O | 3-CF$_3$ | H | H |
| 352 | O | 2-CF$_3$ | 5-CF$_3$ | H |

TABLE 1-continued

Insecticidal Optionally Substituted Benzenes

Formula I
A is FIII; B and D are H; n is 1; U is O; R² is 1-R⁴

| Cmpnd No. | R | X | Y | Z |
|---|---|---|---|---|
| 353 | —N(piperazine)N—CH₂CH₃ | 4-Cl | H | H |
| 354 | —N(piperazine)N—CH₂CH₃ | 4-Cl | 6-Cl | H |
| 355 | —N(piperazine)N—CH₂CH₃ | 5-Cl | 6-Cl | H |
| 356 | —N(piperazine)N—C(O)O—C(CH₃)₃ | 5-Cl | 6-Cl | H |
| 357 | —N(piperazine)N—CH₂CH₃ | 5-Cl | 6-Br | H |
| 358 | —N(piperidine)-(piperidin-1-yl) | 5-Cl | 6-CL | H |
| 359 | —N(piperidine)-(pyrrolidin-1-yl) | 5-Cl | 6-Cl | H |
| 360 | —N(bicyclic)N—CH₃ | 5-Cl | 6-Cl | H |
| 361 | —N(pyrrolidin-3-yl)N(Et)₂ | 5-Cl | 6-Cl | H |
| 362 | —N(piperidine-dioxolane spiro) | 5-Cl | 6-Cl | H |
| 363 | —N(2-methylpiperazine)N—CH₂CH₃ | 4-Cl | 6-Cl | H |
| 364 | —N(piperazine)N—CH₂CH(CH₃)₂ | 5-Cl | 6-Cl | H |

TABLE 1-continued

Insecticidal Optionally Substituted Benzenes

| No. | R¹ | X | Y | Z |
|---|---|---|---|---|
| 365 | —N(piperazine)N—CH2—(2-Cl-phenyl) | 5-Cl | 6-Cl | H |
| 366 | —N(piperazine)N— | 5-Cl | 6-Cl | H |
| 367 | —N(piperazine)N—CH₃ | 5-Cl | 6-Cl | H |
| 368 | —N(piperazine)N—CH₂CH₂CH₃ | 5-Cl | 6-Cl | H |
| 369 | —N(piperazine)N—CH(CH₃)₂ | 5-Cl | 6-Cl | H |
| 369 | —N(piperazine)N—CH(CH₃)₂ | 5-Cl | 6-Cl | H |
| 370 | —N(piperazine)N—CH₂CH₂F | 5-Cl | 6-Cl | H |
| 371 | —N(piperazine)N—phenyl | 5-Cl | 6-Cl | H |

Formula I
A is FIII; B and D are H; R is FII; T is O; n is 1; R² is 1-R⁴; Z is H

| Cmpnd No. | m | n | R¹ | X | Y | U |
|---|---|---|---|---|---|---|
| 372 | 0 | 1 | isobutyl-N(Et)₂ | 5-Cl | 6-Cl | O |
| 373 | 0 | 1 | (2-methylcyclohexyl)-N(Et)₂ | 5-Cl | 6-Cl | O |
| 374 | 0 | 1 | 1,3-dimethylpiperidin-N | 4-Cl | H | O |

TABLE 1-continued

Insecticidal Optionally Substituted Benzenes

| | | | | | | |
|---|---|---|---|---|---|---|
| 375 | 0 | 1 | 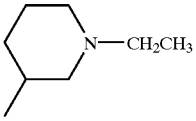 | 4-Cl | H | O |
| 376 | 1 | 1 | 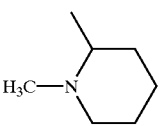 | 5-Cl | 6-Cl | O |
| 377 | 1 | 1 | 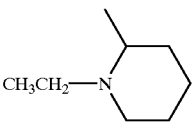 | 5-Cl | 6-Cl | O |
| 378 | 1 | 1 | 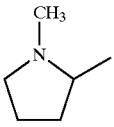 | 5-CL | 6-Cl | O |
| 379 | 2 | 0 | —N(C$_2$H$_5$)$_2$ | 4-Cl | H | —CH$_2$OCH$_2$ |

TABLE 2

Characterizing Data

| Cmpd No | Empirical Formula | Melting Point/Physical State |
|---|---|---|
| 1 | C$_{23}$H$_{27}$ClN$_2$O | OIL |
| 2 | C$_{23}$H$_{27}$ClN$_2$O | OIL |
| 3 | C$_{20}$H$_{33}$N$_3$O$_3$ | OIL |
| 4 | C$_{23}$H$_{29}$ClN$_2$O | OIL |
| 5 | C$_{24}$H$_{30}$ClN$_3$O$_2$ | OIL |
| 6 | C$_{24}$H$_{29}$ClN$_2$O | OIL |
| 7 | C$_{23}$H$_{25}$ClN$_2$O$_2$ | SOLID |
| 8 | C$_{24}$H$_{28}$ClNO$_2$ | SOLID |
| 9 | C$_{22}$H$_{26}$N$_2$O$_2$ | SOLID |
| 10 | C$_{23}$H$_{25}$F$_3$N$_2$O$_2$ | SOLID |
| 11 | C$_{22}$H$_{25}$ClN$_2$O$_2$ | OIL |
| 12 | C$_{22}$H$_{25}$FN$_2$O$_2$ | OIL |
| 13 | C$_{23}$H$_{28}$N$_2$O | OIL |
| 14 | C$_{22}$H$_{27}$N$_3$O | LIQUID |
| 15 | C$_{22}$H$_{27}$N$_3$O | LIQUID |
| 16 | C$_{22}$H$_{27}$N$_3$O | SOLID |
| 17 | C$_{23}$H$_{31}$ClN$_2$O$_2$ | OIL |
| 18 | C$_{18}$H$_{24}$ClN$_3$O | LIQUID |
| 19 | C$_{24}$H$_{32}$ClN$_3$O$_2$ | 93–95° C. |
| 20 | C$_{23}$H$_{31}$ClN$_2$O | OIL |
| 21 | C$_{25}$H$_{27}$NO$_3$ | SOLID |
| 22 | C$_{21}$H$_{25}$N$_3$O$_2$ | OIL |
| 23 | C$_{21}$H$_{24}$ClN$_3$O$_2$ | OIL |
| 24 | C$_{13}$H$_8$F$_5$NO$_2$S | |
| 39 | C$_{21}$H$_{23}$ClN$_2$ | OIL |
| 40 | C$_{25}$H$_{30}$ClN$_3$O | OIL |
| 41 | C$_{28}$H$_{36}$ClN$_3$O$_2$ | FOAM |
| 43 | C$_{19}$H$_{17}$BrO | OIL |
| 44 | C$_{18}$H$_{15}$ClN$_2$O$_2$ | 220° C.> |
| 45 | C$_{25}$H$_{21}$ClO$_3$ | 106–107° C. |
| 46 | C$_{23}$H$_{23}$ClN$_2$O$_2$ | OIL |
| 47 | C$_{24}$H$_{28}$ClNO$_3$ | OIL |
| 48 | C$_{23}$H$_{26}$ClN$_3$O$_2$ | 210° C.> |
| 49 | C$_{25}$H$_{31}$ClN$_2$O | OIL |
| 60 | C$_{21}$H$_{22}$ClNO$_2$ | OIL |
| 61 | C$_{20}$H$_{15}$Cl$_3$O$_2$ | SOLID |
| 62 | C$_{19}$H$_{16}$ClNO$_3$ | 90–92° C. |
| 63 | C$_{23}$H$_{25}$ClN$_2$O$_2$ | 123–125° C. |
| 64 | C$_{19}$H$_{18}$ClNO | 92–93° C. |
| 65 | C$_{19}$H$_{17}$ClFNO | SOLID |
| 66 | C$_{20}$H$_{17}$ClN$_4$O$_2$ | 122–124° C. |
| 67 | C$_{19}$H$_{16}$ClN$_4$O$_2$.Cl | SOLID |
| 68 | C$_{20}$H$_{17}$ClN$_4$O$_2$ | 159–161° C. |
| 69 | C$_{21}$H$_{19}$ClN$_4$O$_2$ | 104–106° C. |
| 70 | C$_{21}$H$_{19}$ClN$_4$O$_2$ | SOLID |
| 71 | C$_{23}$H$_{27}$ClN$_2$S | OIL |
| 72 | C$_{24}$H$_{28}$BrNO | OIL |
| 73 | C$_{24}$H$_{28}$ClNO | OIL |
| 74 | C$_{21}$H$_{24}$N$_2$O | LIQUID |
| 75 | C$_{23}$H$_{28}$N$_2$O | OIL |
| 76 | C$_{23}$H$_{26}$N$_2$O$_2$ | SOLID |
| 77 | C$_{21}$H$_{23}$BrN$_2$O | LIQUID |
| 78 | C$_{23}$H$_{27}$BrN$_2$O | SOLID |
| 79 | C$_{25}$H$_{31}$BrN$_2$O | SOLID |
| 80 | C$_{23}$H$_{25}$BrN$_2$O$_2$ | SOLID |
| 81 | C$_{23}$H$_{25}$BrN$_2$O | SOLID |
| 82 | C$_{21}$H$_{23}$ClN$_2$O | 184–187° C. |
| 83 | C$_{21}$H$_{23}$ClN$_2$O | LIQUID |
| 84 | C$_{23}$H$_{27}$ClN$_2$O | OIL |
| 85 | C$_{23}$H$_{27}$ClN$_2$O.ClH | |
| 86 | C$_{23}$H$_{27}$ClN$_2$O | PASTE |
| 87 | C$_{25}$H$_{31}$ClN$_2$O | SOLID |
| 88 | C$_{27}$H$_{35}$ClN$_2$O | LIQUID |
| 89 | C$_{23}$H$_{25}$ClN$_2$O$_2$ | SOLID |
| 90 | C$_{23}$H$_{25}$ClN$_2$O | SOLID |
| 91 | C$_{22}$H$_{23}$ClN$_2$O$_3$ | 102–104° C. |
| 92 | C$_{24}$H$_{27}$ClN$_2$O$_3$ | OIL |
| 93 | C$_{24}$H$_{27}$ClN$_2$O | SOLID |
| 94 | C$_{22}$H$_{25}$ClN$_2$O | SOLID |
| 95 | C$_{28}$H$_{37}$ClN$_2$O | LIQUID |
| 96 | C$_{24}$H$_{27}$ClN$_2$O$_2$ | LIQUID |
| 97 | C$_{29}$H$_{39}$ClN$_2$O | LIQUID |
| 98 | C$_{25}$H$_{27}$ClO$_2$ | LIQUID |
| 99 | C$_{25}$H$_{28}$ClNO$_2$ | SOLID |

TABLE 2-continued

Characterizing Data

| Cmpd No | Empirical Formula | Melting Point/Physical State |
|---|---|---|
| 100 | $C_{25}H_{26}ClNO_2$ | SOLID |
| 101 | $C_{24}H_{26}ClNO_2$ | 89–90° C. |
| 102 | $C_{25}H_{28}ClNO_2$ | OIL |
| 103 | $C_{25}H_{28}ClNO_2$ | OIL |
| 104 | $C_{25}H_{28}ClNO_2$ | OIL |
| 105 | $C_{26}H_{30}ClNO_2$ | 60–65° C. |
| 106 | $C_{26}H_{30}ClNO_2$ | OIL |
| 107 | $C_{26}H_{29}Cl_2NO_2$ | OIL |
| 108 | $C_{27}H_{30}ClNO_4$ | 85–87° C. |
| 109 | $C_{30}H_{30}ClNO_2$ | 89–91° C. |
| 110 | $C_{31}H_{30}ClNO_3$ | 112–115° C. |
| 111 | $C_{31}H_{32}ClNO_2$ | 88–91° C. |
| 112 | $C_{25}H_{28}ClNO_2$ | SOLID |
| 113 | $C_{23}H_{25}ClN_2O_2$ | OIL |
| 114 | $C_{26}H_{29}ClN_2O_4$ | OIL |
| 115 | $C_{29}H_{29}ClN_2O_2$ | OIL |
| 116 | $C_{30}H_{29}ClN_2O_3$ | OIL |
| 117 | $C_{30}H_{31}ClN_2O_2$ | 71–73° C. |
| 118 | $C_{23}H_{24}ClNO_2S$ | OIL |
| 119 | $C_{25}H_{28}ClNO_3$ | OIL |
| 120 | $C_{25}H_{28}ClNO_3$ | OIL |
| 121 | $C_{28}H_{28}ClNO_2$ | LIQUID |
| 122 | $C_{26}H_{32}ClNO_2$ | 88–90° C. |
| 123 | $C_{26}H_{32}ClNO_2$ | OIL |
| 124 | $C_{26}H_{30}ClNO_2$ | OIL |
| 125 | $C_{26}H_{30}ClNO_2$ | OIL |
| 126 | $C_{24}H_{26}ClNO_2$ | SEMI SOLID |
| 127 | $C_{29}H_{35}ClN_2O_2$ | 91–92° C. |
| 128 | $C_{28}H_{26}ClNO_2$ | SYRUP |
| 129 | $C_{29}H_{31}ClN_2O_2$ | SYRUP |
| 130 | $C_{27}H_{23}ClF_3NO_3$ | SYRUP |
| 131 | $C_{23}H_{26}ClNO_2$ | 58–59° C. |
| 132 | $C_{27}H_{32}ClNO_2$ | OIL |
| 133 | $C_{25}H_{23}ClN_2O_2$ | OIL |
| 134 | $C_{28}H_{28}ClNO_4$ | 96–98° C. |
| 135 | $C_{28}H_{34}ClNO_2$ | OIL |
| 136 | $C_{27}H_{26}ClNO_3$ | 95–96° C. |
| 137 | $C_{26}H_{23}Cl_2NO_2$ | 87–88° C. |
| 138 | $C_{30}H_{37}ClN_2O_2$ | OIL |
| 139 | $C_{27}H_{26}ClNO_2$ | OIL |
| 140 | $C_{28}H_{34}ClNO_2$ | OIL |
| 141 | $C_{23}H_{24}ClNO_2$ | 75–77° C. |
| 142 | $C_{23}H_{23}Cl_2NO_2$ | 152–154° C. |
| 143 | $C_{27}H_{32}ClNO_2$ | OIL |
| 144 | $C_{22}H_{22}ClNO_2S$ | 83–86° C. |
| 145 | $C_{28}H_{32}ClNO_2$ | OIL |
| 146 | $C_{26}H_{30}ClNO_2$ | OIL |
| 147 | $C_{26}H_{30}ClNO_2$ | OIL |
| 148 | $C_{26}H_{30}ClNO_2$ | OIL |
| 149 | $C_{30}H_{27}ClN_2O_2$ | 131–135° C. |
| 150 | $C_{23}H_{22}ClNO_2$ | OIL |
| 151 | $C_{29}H_{27}ClN_2O_2$ | OIL |
| 152 | $C_{30}H_{29}ClN_2O_3$ | 133–136° C. |
| 153 | $C_{30}H_{31}ClN_2O_3$ | OIL |
| 154 | $C_{24}H_{24}ClNO_2$ | 90–91° C. |
| 155 | $C_{30}H_{28}ClF_3N_2O_2$ | 80–82° C. |
| 156 | $C_{29}H_{28}ClFN_2O_2$ | 120–121° C. |
| 157 | $C_{31}H_{31}ClN_2O_3$ | OIL |
| 158 | $C_{36}H_{34}Cl_2N_2O_2$ | OIL |
| 159 | $C_{27}H_{30}ClNO_4$ | OIL |
| 160 | $C_{29}H_{35}ClN_2O_3$ | OIL |
| 161 | $C_{30}H_{30}ClNO_3$ | 123–125° C. |
| 162 | $C_{28}H_{28}ClN_3O_2$ | OIL |
| 163 | $C_{27}H_{27}ClN_2O_2$ | OIL |
| 164 | $C_{29}H_{28}ClN_3O_4$ | 164–166° C. |
| 165 | $C_{26}H_{31}ClN_2O_2$ | 83–89° C. |
| 166 | $C_{25}H_{31}ClN_2O_2$ | OIL |
| 167 | $C_{29}H_{35}ClN_2O_2$ | 135–140° C. |
| 168 | $C_{28}H_{32}ClNO_2$ | OIL |
| 169 | $C_{27}H_{27}ClN_2O_2$ | OIL |
| 170 | $C_{28}H_{28}ClNO_2$ | OIL |
| 181 | $C_{23}H_{25}Cl_2NO_3$ | OIL |
| 183 | $C_{23}H_{25}Cl_2NO_3$ | 81–87° C. |
| 184 | $C_{21}H_{22}ClNO_2$ | LIQUID |
| 185 | $C_{21}H_{23}ClNO_2.Cl$ | 201–203° C. |
| 186 | $C_{23}H_{26}ClNO_2$ | LIQUID |
| 187 | $C_{23}H_{26}ClNO_2$ | OIL |
| 188 | $C_{23}H_{26}ClNO_2$ | OIL |
| 189 | $C_{23}H_{26}ClNO_2.ClH$ | SOLID |
| 190 | $C_{23}H_{27}ClNO_2.I$ | LIQUID |
| 191 | $C_{23}H_{23}ClN_2O_2$ | LIQUID |
| 192 | $C_{22}H_{24}ClNO_2$ | SOLID |
| 193 | $C_{22}H_{25}ClNO_2.Cl$ | SOLID |
| 194 | $C_{23}H_{26}ClNO_2$ | 84–85° C. |
| 195 | $C_{24}H_{28}ClNO_3$ | SYRUP |
| 196 | $C_{25}H_{26}ClNO_2$ | OIL |
| 197 | $C_{23}H_{26}ClNO_4$ | OIL |
| 198 | $C_{23}H_{26}ClNO_3$ | SEMI-SOLID |
| 199 | $C_{23}H_{26}ClNO_2$ | 138–145° C. |
| 200 | $C_{23}H_{23}ClN_2O_2$ | OIL |
| 201 | $C_{25}H_{30}ClNO_2$ | OIL |
| 202 | $C_{27}H_{34}ClNO_2$ | OIL |
| 203 | $C_{25}H_{30}ClNO_2$ | OIL |
| 204 | $C_{31}H_{42}ClNO_2$ | OIL |
| 205 | $C_{38}H_{56}ClNO_2$ | 63–64° C. |
| 206 | $C_{23}H_{26}ClNO_2$ | LIQUID |
| 207 | $C_{23}H_{26}ClNO_2$ | LIQUID |
| 208 | $C_{23}H_{26}ClNO_2$ | OIL |
| 209 | $C_{23}H_{26}ClNO_2$ | LIQUID |
| 210 | $C_{23}H_{25}Cl_2NO_2$ | OIL |
| 211 | $C_{23}H_{25}Cl_2NO_2$ | OIL |
| 213 | $C_{23}H_{25}Cl_2NO_2$ | LIQUID |
| 214 | $C_{23}H_{24}Cl_3NO_2$ | SOLID |
| 215 | $C_{23}H_{25}Cl_2NO_2$ | LIQUID |
| 216 | $C_{23}H_{25}Cl_2NO_2$ | OIL |
| 217 | $C_{23}H_{25}C_{12}NO_2.ClH$ | 200° C.> |
| 218 | $C_{23}H_{25}Cl_2NO_2.CH_4O_3S$ | SOLID |
| 219 | $C_{23}H_{25}Cl_2NO_2.C_2HF_3O_2$ | SOLID |
| 220 | $C_{23}H_{25}Cl_2NO_2.C_7H_8O_3S$ | SOLID |
| 221 | $C_{23}H_{25}Cl_2NO_2$ | PASTE |
| 222 | $C_{23}H_{25}Cl_2NO_2$ | PASTE |
| 223 | $C_{23}H_{25}Cl_2NO_2$ | OIL |
| 224 | $C_{23}H_{26}Cl_2NO_2.Cl$ | 204–206° C. |
| 225 | $C_{23}H_{25}Cl_2NO_2.H_3O_4P$ | SOLID |
| 226 | $C_{23}H_{25}Cl_2NO_2$ | 215–217° C. |
| 227 | $C_{23}H_{25}Cl_2NO_2$ | OIL |
| 228 | $C_{23}H_{26}BrNO_2$ | OIL |
| 229 | $C_{23}H_{26}BrNO_2$ | SOLID |
| 230 | $C_{23}H_{26}BrNO_2$ | SOLID |
| 231 | $C_{23}H_{26}FNO_2$ | SOLID |
| 232 | $C_{24}H_{26}F_3NO_2$ | OIL |
| 233 | $C_{24}H_{26}F_3NO_2$ | COLORLESS OIL |
| 234 | $C_{23}H_{28}N_2O_2$ | OIL |
| 235 | $C_{24}H_{29}NO_3$ | OIL |
| 236 | $C_{24}H_{29}NO_3.ClH$ | SOLID |
| 237 | $C_{24}H_{29}NO_3$ | OIL |
| 238 | $C_{23}H_{26}N_2O_4$ | OIL |
| 239 | $C_{24}H_{26}N_2O_2$ | OIL |
| 240 | $C_{24}H_{29}NO_2$ | OIL |
| 241 | $C_{24}H_{29}NO_2$ | SOLID |
| 242 | $C_{29}H_{30}FNO_2$ | 67–71° C. |
| 243 | $C_{29}H_{30}ClNO_3$ | OIL |
| 259 | $C_{24}H_{28}ClNO_2$ | LIQUID |
| 260 | $C_{25}H_{30}ClNO_2$ | LIQUID |
| 261 | $C_{23}H_{25}Cl_2NO_2.C_{23}H_{24}Cl_3NO_2$ | LIQUID |
| 262 | $C_{23}H_{26}ClFN_2O$ | LIQUID |
| 263 | $C_{24}H_{29}ClN_3O_2$ | LIQUID |
| 264 | $C_{24}H_{29}ClN_2O_2$ | SOLID |
| 265 | $C_{25}H_{31}ClN_2O_3$ | LIQUID |
| 266 | $C_{29}H_{40}ClN_3O_2$ | LIQUID |
| 267 | $C_{23}H_{26}Cl_2N_2O$ | LIQUID |
| 268 | $C_{23}H_{26}Cl_2N_2O$ | LIQUID |
| 269 | $C_{23}H_{25}Cl_3N_2O$ | SOLID |
| 270 | $C_{23}H_{25}Cl_3N_2O$ | SOLID |
| 271 | $C_{23}H_{25}Cl_3N_2O$ | SOLID |
| 272 | $C_{23}H_{23}Cl_3N_2O_2$ | SOLID |
| 273 | $C_{19}H_{25}ClN_2O$ | LIQUID |
| 274 | $C_{19}H_{25}ClN_2O$ | LIQUID |

TABLE 2-continued

Characterizing Data

| Cmpd No | Empirical Formula | Melting Point/Physical State |
|---|---|---|
| 275 | $C_{20}H_{25}ClN_2O_2$ | OIL |
| 276 | $C_{24}H_{31}ClN_2O_4$ | OIL |
| 277 | $C_{20}H_{26}ClNO_2$ | OIL |
| 278 | $C_{19}H_{26}N_2O$ | OIL |
| 279 | $C_{20}H_{25}F_3N_2O_2$ | OIL |
| 280 | $C_{20}H_{25}F_3N_2O_2$ | OIL |
| 281 | $C_{25}H_{30}N_2O_2$ | OIL |
| 282 | $C_{25}H_{30}N_2O_2$ | OIL |
| 283 | $C_{19}H_{25}ClN_2O$ | OIL |
| 284 | $C_{19}H_{25}ClN_2O$ | OIL |
| 285 | $C_{19}H_{24}Cl_2N_2O$ | OIL |
| 286 | $C_{19}H_{23}Cl_3N_2O$ | OIL |
| 287 | $C_{19}H_{24}Cl_2N_2O$ | OIL |
| 288 | $C_{19}H_{23}Cl_3N_2O$ | OIL |
| 289 | $C_{19}H_{24}Cl_2N_2O$ | OIL |
| 290 | $C_{19}H_{24}Cl_2N_2O$ | OIL |
| 291 | $C_{25}H_{30}N_2O$ | LIQUID |
| 292 | $C_{25}H_{29}ClN_2O$ | LIQUID |
| 293 | $C_{25}H_{29}ClN_2O$ | LIQUID |
| 294 | $C_{19}H_{24}F_2N_2O$ | OIL |
| 295 | $C_{19}H_{23}F_3N_2O$ | OIL |
| 296 | $C_{19}H_{24}F_2N_2O$ | OIL |
| 297 | $C_{19}H_{23}F_3N_2O$ | OIL |
| 298 | $C_{21}H_{30}N_2O$ | OIL |
| 299 | $C_{21}H_{30}N_2O$ | OIL |
| 300 | $C_{21}H_{30}N_2O_3$ | OIL |
| 301 | $C_{21}H_{30}N_2O_3$ | OIL |
| 302 | $C_{21}H_{30}N_2O_3$ | OIL |
| 303 | $C_{21}H_{29}NO_4$ | LIQUID |
| 304 | $C_{26}H_{31}NO_3$ | SOLID |
| 305 | $C_{19}H_{24}ClNO_2$ | SOLID |
| 306 | $C_{19}H_{24}ClNO_2$ | SOLID |
| 307 | $C_{19}H_{23}Cl_2NO_2$ | LIQUID |
| 308 | $C_{19}H_{22}Cl_3NO_2$ | SOLID |
| 309 | $C_{19}H_{23}Cl_2NO_2$ | LIQUID |
| 310 | $C_{19}H_{22}Cl_3NO_2$ | LIQUID |
| 311 | $C_{19}H_{23}Cl_2NO_2$ | LIQUID |
| 312 | $C_{19}H_{23}Cl_2NO_2$ | LIQUID |
| 313 | $C_{19}H_{23}Cl_2NO_2$ | SOLID |
| 314 | $C_{19}H_{23}Cl_2NO_2$ | SEMI-SOLID |
| 315 | $C_{19}H_{23}BrClNO_2$ | SOLID |
| 316 | $C_{19}H_{23}BrClNO_2$ | LIQUID |
| 317 | $C_{20}H_{26}ClNO_2$ | LIQUID |
| 318 | $C_{23}H_{33}NO_2$ | LIQUID |
| 319 | $C_{23}H_{33}NO_2$ | SOLID |
| 320 | $C_{23}H_{33}NO_2$ | LIQUID |
| 321 | $C_{22}H_{31}NO_2$ | LIQUID |
| 322 | $C_{22}H_{31}NO_2$ | SOLID |
| 323 | $C_{20}H_{27}NO_3$ | SOLID |
| 324 | $C_{20}H_{24}F_3NO_3$ | SOLID |
| 325 | $C_{20}H_{24}N_2O_2$ | LIQUID |
| 326 | $C_{20}H_{24}N_2O_2$ | LIQUID |
| 327 | $C_{21}H_{28}N_2O_3$ | SOLID |
| 328 | $C_{22}H_{29}NO_4$ | SOLID |
| 329 | $C_{21}H_{27}NO_3$ | LIQUID |
| 330 | $C_{22}H_{29}NO_4$ | LIQUID |
| 331 | $C_{22}H_{29}NO_4$ | SOLID |
| 332 | $C_{20}H_{26}ClNO_2$ | LIQUID |
| 333 | $C_{20}H_{26}ClNO_2$ | SOLID |
| 334 | $C_{19}H_{23}ClN_2O_4$ | LIQUID |
| 335 | $C_{22}H_{25}ClN_2O_3$ | LIQUID |
| 336 | $C_{23}H_{27}ClN_2O_3$ | LIQUID |
| 337 | $C_{21}H_{29}NO_2$ | LIQUID |
| 338 | $C_{22}H_{31}NO_2$ | SOLID |
| 339 | $C_{22}H_{31}NO_2$ | SOLID |
| 340 | $C_{21}H_{29}NO_3$ | LIQUID |
| 341 | $C_{19}H_{23}Br_2NO_2$ | SOLID |
| 342 | $C_{19}H_{23}Br_2NO_2$ | LIQUID |
| 343 | $C_{20}H_{26}BrNO_2$ | LIQUID |
| 344 | $C_{20}H_{25}Br_2NO_2$ | SOLID |
| 345 | $C_{19}H_{23}F_2NO_2$ | SOLID |
| 346 | $C_{19}H_{23}F_2NO_2$ | LIQUID |
| 347 | $C_{19}H_{23}F_2NO_2$ | LIQUID |
| 348 | $C_{19}H_{23}F_2NO_2$ | LIQUID |
| 349 | $C_{19}H_{23}F_2NO_2$ | LIQUID |
| 350 | $C_{19}H_{22}F_3NO_2$ | LIQUID |
| 351 | $C_{20}H_{24}F_3NO_2$ | LIQUID |
| 352 | $C_{21}H_{23}F_6NO_2$ | LIQUID |
| 353 | $C_{23}H_{24}ClN_2O$ | SOLID |
| 354 | $C_{23}H_{24}Cl_2N_2O$ | SOLID |
| 355 | $C_{23}H_{24}Cl_2N_2O$ | SOLID |
| 356 | $C_{26}H_{28}Cl_2N_2O_3$ | SOLID |
| 357 | $C_{23}H_{24}BrClN_2O$ | 150–151° C. |
| 358 | $C_{27}H_{30}Cl_2N_2O$ | 142–145° C. |
| 359 | $C_{26}H_{28}Cl_2N_2O$ | 131–133° C. |
| 360 | $C_{23}H_{22}Cl_2N_2O$ | 135–137° C. |
| 361 | $C_{25}H_{28}Cl_2N_2O$ | SOLID |
| 363 | $C_{24}H_{26}Cl_2N_2O$ | SOLID |
| 364 | $C_{25}H_{28}Cl_2N_2O$ | SOLID |
| 365 | $C_{28}H_{25}Cl_3N_2O$ | SOLID |
| 366 | $C_{21}H_{20}Cl_2N_2O$ | SOLID |
| 267 | $C_{22}H_{22}Cl_2N_2O$ | SOLID |
| 368 | $C_{24}H_{26}Cl_2N_2O$ | SOLID |
| 369 | $C_{24}H_{26}Cl_2N_2O$ | SOLID |
| 370 | $C_{23}H_{23}Cl_2FN_2O$ | SOLID |
| 371 | $C_{27}H_{24}Cl_2N_2O$ | SOLID |
| 372 | $C_{24}H_{27}Cl_2NO_2$ | OIL |
| 373 | $C_{27}H_{31}Cl_2NO_2$ | OIL |
| 374 | $C_{23}H_{24}ClNO_2$ | SEMI-SOLID |
| 375 | $C_{24}H_{26}ClNO_2$ | OIL |
| 376 | $C_{24}H_{25}Cl_2NO_2$ | OIL |
| 377 | $C_{25}H_{27}Cl_2NO_2$ | OIL |
| 378 | $C_{23}H_{23}Cl_2NO_2$ | SOLID |
| 379 | $C_{24}H_{28}ClNO_2$ | SOLID |

TABLE 3

Insecticidal Activity of 1,4-Disubstituted Benzenes Incorporated into the Diet (SRTD) of Tobacco Budworm

| Cmpd No. | Rate of Application[1] | Percent Growth Inhibition[2] | Percent Mortality[3] |
|---|---|---|---|
| 8 | 4.6 | 11 | — |
| 10 | 4.6 | 35 | — |
| 20 | 5.6 | 12 | — |
| 21 | 5.6 | 20 | — |
| 47 | 4.6 | 23 | — |
| 49 | 4.6 | 16 | — |
| 66 | 4.6 | 9 | — |
| 68 | 5.6 | 16 | — |
| 72 | 5.6 | 23 | — |
| 73 | 5.6 | 24 | — |
|  | 5.6 | 20 | — |
| 77 | 5.6 | 17 | — |
| 78 | 5.6 | 12 | — |
|  | 5.6 | 0 | — |
| 79 | 6.6 | −4 | — |
| 80 | 5.6 | 12 | — |
| 82 | 5.6 | 12 | — |
| 84 | 6.6 | −20 | — |
|  | 6.6 | 34 | — |
|  | 5.6 | 11 | — |
| 85 | 6.6 | 20 | — |
|  | 5.6 | 15 | — |
| 87 | 6.6 | −2 | — |
| 88 | 5.6 | 1 | — |
| 89 | 5.6 | 12 | — |
| 93 | 6.6 | 3 | — |
| 94 | 4.6 | 18 | — |
| 99 | 6.6 | 6 | — |
| 100 | 6.6 | 6 | — |
| 101 | 6.6 | 14 | — |
| 102 | 6.6 | 7 | — |
| 103 | 5.6 | 25 | — |

TABLE 3-continued

Insecticidal Activity of 1,4-Disubstituted Benzenes
Incorporated into the Diet (SRTD) of Tobacco Budworm

| Cmpd No. | Rate of Application[1] | Percent Growth Inhibition[2] | Percent Mortality[3] |
|---|---|---|---|
| 104 | 5.6 | 21 | — |
| 105 | 4.6 | 24 | — |
| 106 | 6.6 | 35 | — |
| 107 | 6.6 | 17 | — |
| 111 | 5.6 | 1 | — |
| 112 | 5.6 | 26 | — |
| 113 | 5.6 | −3 | — |
| 114 | 5.6 | 0 | — |
| 117 | 5.6 | 10 | — |
| 118 | 4.6 | 6 | — |
| 121 | 4.6 | 12 | — |
| 122 | 5.6 | 23 | — |
| 123 | 5.6 | 30 | — |
| 124 | 5.6 | 20 | — |
| 125 | 5.6 | 18 | — |
| 126 | 6.6 | 14 | — |
| 130 | 6.6 | 17 | — |
| 131 | 6.6 | 25 | — |
| 132 | 5.6 | 27 | — |
| 133 | 4.6 | 28 | — |
| 134 | 4.6 | 12 | — |
| 135 | 5.6 | 24 | — |
| 136 | 4.6 | 33 | — |
| 137 | 4.6 | 28 | — |
| 138 | 4.6 | 27 | — |
| 139 | 4.6 | 26 | — |
| 140 | 5.6 | 32 | — |
| 141 | 6.6 | 24 | — |
| 142 | 6.6 | 32 | — |
| 143 | 4.6 | 22 | — |
| 144 | 4.6 | 20 | — |
| 145 | 5.6 | 29 | — |
| 146 | 5.6 | 25 | — |
| 147 | 5.6 | 33 | — |
| 148 | 5.6 | 4 | — |
| 149 | 5.6 | 22 | — |
| 150 | 5.6 | 12 | — |
| 151 | 5.6 | 5 | — |
| 152 | 4.6 | 16 | — |
| 153 | 4.6 | 19 | — |
| 154 | 6.6 | 27 | — |
| 161 | 5.6 | 23 | — |
| 163 | 5.6 | 24 | — |
| 166 | 5.6 | 24 | — |
| 181 | 6.6 | 43 | — |
| 183 | 6.6 | 28 | — |
|  | 6.6 | 18 | — |
| 184 | 5.6 | 43 | — |
| 187 | 4.6 | 14 | — |
| 188 | 6.6 | 1 | — |
|  | 6.6 | 19 | — |
|  | 6.6 | −1 | — |
| 190 | 5.6 | 4 | — |
| 191 | 6.6 | 6 | — |
| 192 | 6.6 | 2 | — |
| 193 | 6.6 | 4 | — |
| 194 | 6.6 | 19 | — |
| 195 | 5.6 | 30 | — |
| 196 | 5.6 | 20 | — |
| 197 | 4.6 | 43 | — |
| 198 | 5.6 | 21 | — |
| 199 | 5.6 | 9 | — |
| 200 | 5.6 | 19 | — |
| 201 | 5.6 | 13 | — |
| 202 | 5.6 | 20 | — |
| 203 | 6.6 | 14 | — |
| 206 | 6.6 | 12 | — |
| 207 | 6.6 | 20 | — |
| 209 | 6.6 | 17 | — |
| 213 | 4.6 | 3 | — |
| 214 | 6.6 | 18 | — |
| 215 | 6.6 | 8 | — |
| 216 | 6.6 | 2 | — |
|  | 6.6 | 1 | — |
|  | 6.6 | 1 | — |
|  | 6.6 | 14 | — |
| 217 | 6.6 | 26 | — |
|  | 6.6 | 34 | — |
| 218 | 6.6 | 28 | — |
| 219 | 6.6 | 16 | — |
| 220 | 6.6 | 28 | — |
| 221 | 6.6 | 13 | — |
| 222 | 6.6 | 24 | — |
| 223 | 6.6 | 63 | — |
|  | 7.6 | 3 | — |
|  | 7.6 | 17 | — |
| 224 | 6.6 | 81 | — |
|  | 6.6 | 20 | — |
|  | 6.6 | 32 | — |
| 226 | 6.6 | 59 | — |
| 227 | 4.6 | 7 | — |
| 228 | 6.6 | 17 | — |
|  | 6.6 | 5 | — |
|  | 6.6 | 0 | — |
| 229 | 6.6 | 14 | — |
| 230 | 6.6 | 12 | — |
| 231 | 5.6 | 3 | — |
| 232 | 6.6 | 25 | — |
|  | 6.6 | 1 | — |
| 233 | 6.6 | 17 | — |
| 234 | 5.6 | −3 | — |
| 236 | 4.6 | 14 | — |
| 237 | 5.6 | 12 | — |
| 238 | 6.6 | 22 | — |
| 239 | 5.6 | 5 | — |
| 241 | 5.6 | 8 | — |
| 242 | 6.6 | 11 | — |
| 243 | 6.6 | 10 | — |
| 262 | 4.6 | 7 | — |
| 263 | 5.6 | 26 | — |
| 264 | 6.6 | 19 | — |
| 267 | 4.6 | 7 | — |
| 273 | 5.6 | 5 | — |
| 290 | 5.6 | 1 | — |
| 306 | 4.6 | −2 | — |
| 308 | 5.6 | 18 | — |
| 313 | 4.6 | 37 | — |
| 350 | 4.6 | 21 | — |
| 353 | 3.6 | 100 | 100 |
|  | 4.6 | 100 | 67 |
|  | 5.6 | 45 | — |
|  | 6.6 | 21 | — |
| 354 | 3.6 | 100 | 100 |
|  | 4.6 | 100 | 100 |
|  | 5.6 | 96 | 17 |
|  | 6.6 | −2 | — |
| 355 | 3.6 | 100 | 100 |
|  | 4.6 | 100 | 100 |
|  | 5.6 | 96 | 17 |
|  | 6.6 | −2 | — |
| 356 | 3.6 | 2 | — |
|  | 4.6 | −4 | — |
| 357 | 3.6 | 100 | 100 |
|  | 4.6 | 50 | 99 |
|  | 5.6 | — | 15 |
| 360 | 3.6 | 73 | — |
|  | 4.6 | 11 | — |
| 364 | 4.6 | 83 | — |
|  | 5.6 | −1 | — |
| 365 | 3.6 | 28 | — |
|  | 4.6 | 18 | — |
| 366 | 3.6 | 82 | — |
|  | 4.6 | 47 | — |
|  | 5.6 | 3 | — |
| 367 | 3.6 | 100 | 100 |
|  | 4.6 | 100 | 100 |

TABLE 3-continued

Insecticidal Activity of 1,4-Disubstituted Benzenes
Incorporated into the Diet (SRTD) of Tobacco Budworm

| Cmpd No. | Rate of Application[1] | Percent Growth Inhibition[2] | Percent Mortality[3] |
|---|---|---|---|
| | 5.6 | 98 | 33 |
| | 6.6 | 25 | — |
| 368 | 3.6 | 100 | 100 |
| | 4.6 | 100 | 100 |
| | 5.6 | 102 | 50 |
| | 6.6 | 36 | — |
| 369 | 3.6 | 100 | 100 |
| | 4.6 | 100 | 100 |
| | 5.6 | 100 | 83 |
| | 6.6 | 28 | — |
| 372 | 3.6 | 100 | 100 |
| | 4.6 | 100 | 100 |
| | 5.6 | 100 | 100 |
| | 6.6 | 42 | — |
| 373 | 3.6 | 100 | 100 |
| | 4.6 | 97 | 17 |
| | 5.6 | 37 | — |
| | 6.6 | −1 | — |
| 374 | 3.6 | 100 | 100 |
| | 4.6 | 98 | 50 |
| | 5.6 | 41 | — |
| | 6.6 | −1 | — |
| 375 | 3.6 | 101 | 100 |
| | 4.6 | 85 | 17 |
| | 5.6 | 23 | — |
| 376 | 3.6 | 100 | 100 |
| | 4.6 | 100 | 100 |
| | 5.6 | 89 | — |
| | 6.6 | 22 | — |
| 377 | 3.6 | 100 | 100 |
| | 4.6 | 99 | 67 |
| | 5.6 | 59 | — |
| | 6.6 | 4 | — |
| 378 | 3.6 | 100 | 100 |
| | 4.6 | 100 | 100 |
| | 5.6 | 101 | 83 |
| | 6.6 | 48 | — |
| 379 | 3.6 | 86 | 33 |
| | 4.6 | 11 | — |

FOOTNOTES
[1]The rate of application is expressed as the negative log of the molar concentration of the test compound in the diet.
[2]Percent growth inhibition is derived from the total weight of the insects (IW) at each rate of application in the test relative to the total weight of insects in an untreated control, % Gr. Inh. = [IW (control) − I (test)/IW (control)] × 100.
[3]Percent mortality is derived from the number of dead insects (TD) relative to the total number of insects (TI) used in the test, % Mortality = TD/TI × 100

We claim:

1. A compound of formula I:

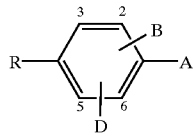

wherein:
A is selected from the group consisting of hydrogen; aryl; alkylheterocyclyl; alkenylaminopolycyclyl; alkenylaminoheterocyclyl; alkylaminopolycyclyl; carbonylaminopolycyclyl; where the aryl, heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and Formula III, where Formula III is $$-(CH_2)_n-U-R^2 \qquad III$$

wherein
n is 0 or 1;
U is selected from the group consisting of —CH$_2$—, —O—CH$_2$—, oxygen, sulfur, sulfonyl, alkyl, oxyalkyloxy, alkenylamino, cabonylamino and —NR$^5$, where R$^5$ is selected from the group consisting of hydrogen, hydroxy, alkyl, haloalkyl, sulfonylalkyl, cabonylamino, and carbonylalkyl;
R$^2$ is selected from aryl; alkylpolycyclyl; heterocyclyl; polycyclyl; where the aryl, heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; 1-R$^3$; 1-R$^4$; and 2-R$^4$, wherein:
R$^3$ is

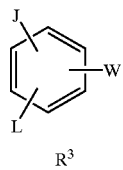

where J, L, and W are independently selected from the group consisting of hydrogen, halogen, cyano, nitro, amino, carboxyl, alkyl, haloalkyl, alkenyl, alkoxy, haloalkoxy, aminoalkoxy, nitrilyl, carbonyl, alkylcarbonyl, haloalkylcarbonyl, alkoxycarbonyl, haloalkoxycarbonyl, aryl, aryloxy, and heterocyclyl, where the aryl and heterocyclyl moieties may be optionally substituted with halogen, alkyl, haloalkyl, alkoxy, or haloalkoxy;
R$^4$ is

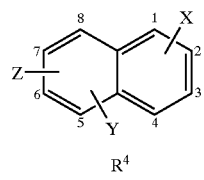

where X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, aryloxy, and heterocyclyl, where the phenyl, aryl, and heterocyclyl moieties may be optionally substituted with halogen, haloalkyl, haloalkyl, alkoxy, or haloalkoxy;
with the proviso that X, Y and Z cannot all be hydrogen;
B and D are independently selected from hydrogen, halogen, alkyl, haloalkyl, alkoxy, haloalkoxy, alkoxyaminoalkyl, 2-(Formula III), 3-(Formula III), 5-(Formula III), and 6-(Formula III), wherein Formula III, n, U, $R^2$, $R^3$, $R^4$, $R^5$, J, L, W, X, Y, and Z are as defined above;

R is —T—$(CH_2)_m$—$R^1$, —$N(R^6)(R^7)$ or heterocyclyl, where the heterocyclyl moiety may be optionally substituted with halogen, hydroxy, alkyl, haloalkyl, alkoxy, haloalkoxy, alkoxycarbonyl, aryl, alkylaza, arylcarbonyl, benzyl, allyl, propargyl, alkylamino; where the aryl moiety may be optionally substituted with halogen, hydroxy, alkyl, haloalkyl, alkoxy, haloalkoxy, alkoxycarbonyl, aryl, arylcarbonyl;

T is selected from the group consisting of —$CH_2$—, carbonyl, oxygen, nitrogen, and sulfur;

m is 0, 1, 2, 3, or 4;

$R^1$ is selected from the group consisting of —$N(R^8)$ $(R^9)$; aryl; —$C(O)N(R^{12})(R^{13})$; oxyalkyl; haloalkyl; heterocyclyl; cycloalkyl; —$N(O)(R^{14})(R^{15})$; —$P(O)$ $(R^{14})(R^{15})$; —$P(S)(R^{14})(R^{15})$; alkylamino, where the cycloalkyl, aryl and heterocyclyl moieties may be optionally substituted with halogen, hydroxy, alkyl, haloalkyl, alkoxy, haloalkoxy, alkoxycarbonyl, aryl, arylcarbonyl, alkylamino; where $R^6$, $R^7$, $R^8$, $R^9$, $R^{12}$, $R^{13}$, $R^{14}$, and $R^{15}$ are independently selected from the group consisting of hydrogen, alkyl, alkoxy, alkylthio, acetyl, alkoxycarbonyl, alkoxyalkyl, aminoalkyl, carbonylamino, and —$(CH_2)_p$—$N(R^{16})(R^{17})$, where p is 1 or 2;

$R^{16}$ and $R^{17}$ are independently selected from the group consisting of hydrogen, alkyl, alkoxy, alkoxyalkyl, and aminoalkyl;

with the provisos that (i) when A, B and D are hydrogen, R is other than heterocyclyl; (ii) when A, B, and D are hydrogen, R is —T—$(CH_2)_m$—$R^1$, T is oxygen, m is 2, $R^1$ is —$N(R^8)(R^9)$, and $R^8$ is hydrogen, $R^9$ is other than hydrogen; and (iii) when B and D are hydrogen, A is —$(CH_2)_n$—U—$R^2$, R is —T—$(CH_2)_m$—$R^1$, T is oxygen, U is oxygen, m is 2, n is 1, $R^1$ is —$N(R^8)(R^9)$, $R^2$ is 1-$R^3$, J, L, W, are hydrogen; and $R^8$ is alkyl, $R^9$ is other than the same alkyl;

and the corresponding agriculturally acceptable salts thereof.

2. A compound of claim 1 wherein

A is selected from the group consisting of hydrogen; alkylaminopolycyclyl; carbonylaminopolycyclyl; where the polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and Formula III, where Formula III is

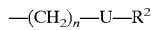  III wherein n is 0 or 1;

U is selected from the group consisting of —$CH_2$—, oxygen, and —$NR^5$, where $R^5$ is selected from the group consisting of hydrogen, hydroxy, alkyl, sulfonylalkyl, cabonylamino, and carbonylalkyl;

$R^2$ is selected from aryl, alkylpolycyclyl; heterocyclyl; polycyclyl; where the aryl, heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and 1-$R^3$, wherein $R^3$ is:

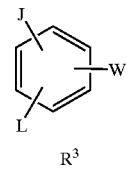

where J, L, and W are independently selected from the group consisting of hydrogen, halogen, cyano, nitro, amino, carboxyl, alkyl, haloalkyl, alkenyl, alkoxy, haloalkoxy, nitrilyl, carbonyl, alkylcarbonyl, haloalkylcarbonyl, alkoxycarbonyl, haloalkoxycarbonyl, aryl, and aryloxy, where the aryl moieties may be optionally substituted with halogen, alkyl, haloalkyl, alkoxy, or haloalkoxy;

B and D are independently selected from hydrogen, halogen, alkyl, haloalkyl, alkoxy, haloalkoxy, alkoxyaminoalkyl;

R is —T—$(CH_2)_m$—$R^1$, where

T is selected from the group consisting of —$CH_2$—, oxygen, nitrogen, and sulfur;

m is 1, 2, 3, or 4;

$R^1$ is —$N(R^8)(R^9)$; where $R^8$ and $R^9$ are independently selected from the group consisting of hydrogen, alkyl, alkoxy, acetyl, alkoxycarbonyl, alkoxyalkyl, aminoalkyl, carbonylamino, and —$(CH_2)_p$—$N(R^{16})(R^{17})$, where p is 1 or 2;

$R^{16}$ and $R^{17}$ are independently selected from the group consisting of hydrogen, alkyl, alkoxy, alkoxyalkyl, and aminoalkyl;

and the corresponding agriculturally acceptable salts thereof.

3. A compound of claim 2 wherein

A is hydrogen or Formula III, where Formula III is

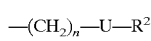  III wherein n is 0 or 1;

U is selected from the group consisting of —$CH_2$—, oxygen, and —$NR^5$, where $R^5$ is selected from the group consisting of hydrogen, hydroxy, alkyl, sulfonylalkyl, cabonylamino, and carbonylalkyl;

$R^2$ is selected from heterocyclyl; polycyclyl; where the heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and 1-$R^3$, wherein $R^3$ is:

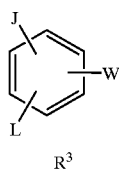

R³ where J, L, and W are independently selected from the group consisting of hydrogen, halogen, cyano, nitro, amino, carboxyl, alkyl, haloalkyl, alkenyl, alkoxy, haloalkoxy, nitrilyl, carbonyl, alkylcarbonyl, haloalkylcarbonyl, alkoxycarbonyl, haloalkoxycarbonyl, aryl, and aryloxy, where the aryl moieties may be optionally substituted with halogen, alkyl, haloalkyl, alkoxy, or haloalkoxy;

B and D are independently selected from hydrogen, halogen, alkyl, haloalkyl, alkoxy, haloalkoxy, alkoxyaminoalkyl;

T is oxygen or nitrogen m is 2, 3, or 4;

$R^1$ is —$N(R^8)(R^9)$; where $R^8$ and $R^9$ are independently selected from the group consisting of hydrogen, alkyl, alkoxy, acetyl, alkoxycarbonyl, alkoxyalkyl, aminoalkyl, carbonylamino, and —$(CH_2)_p$—$N(R^{16})(R^{17})$, where p is 1 or 2;

$R^{16}$ and $R^{17}$ are independently selected from the group consisting of hydrogen, alkyl, alkoxy, alkoxyalkyl, and aminoalkyl.

4. A compound of claim 3 wherein

A is Formula III, where Formula III is

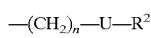  III wherein n is 1;

U is oxygen or —$NR^5$, where $R^5$ is selected from the group consisting of hydrogen, hydroxy, alkyl, sulfonylalkyl, cabonylamino, and carbonylalkyl;

$R^2$ is 1-$R^3$, wherein $R^3$ is:

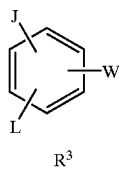

R³ where J, L, and W are independently selected from the group consisting of hydrogen, halogen, cyano, nitro, amino, carboxyl, alkyl, haloalkyl, alkenyl, alkoxy, haloalkoxy, nitrilyl, carbonyl, alkylcarbonyl, haloalkylcarbonyl, alkoxycarbonyl, haloalkoxycarbonyl, aryl, and aryloxy, where the aryl moieties may be optionally substituted with halogen, alkyl, haloalkyl, alkoxy, or haloalkoxy;

B and D are independently selected from hydrogen, halogen, alkyl, haloalkyl, alkoxy, haloalkoxy, alkoxyaminoalkyl;

T is oxygen or nitrogen m is 2;

$R^1$ is —$N(R^8)(R^9)$; where $R^8$ and $R^9$ are independently selected from the group consisting of hydrogen, alkyl, alkoxy, acetyl, alkoxycarbonyl, alkoxyalkyl, aminoalkyl, carbonylamino, and —$(CH_2)_p$—$N(R^{16})(R^{17})$, where p is 1 or 2;

$R^{16}$ and $R^{17}$ are independently selected from the group consisting of hydrogen, alkyl, alkoxy, alkoxyalkyl, and aminoalkyl.

5. A compound of claim 1 wherein

A is selected from the group consisting of hydrogen; alkylaminopolycyclyl; and carbonylaminopolycyclyl; where the polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and Formula III, where Formula III is

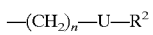  III wherein n is 0 or 1;

U is selected from the group consisting of —$CH_2$—, oxygen, alkyl, oxyalkyloxy, alkenylamino, cabonylamino and —$NR^5$, where $R^5$ is selected from the group consisting of hydrogen, hydroxy, alkyl, sulfonylalkyl, cabonylamino, and carbonylalkyl;

$R^2$ is selected from aryl; alkylpolycyclyl; heterocyclyl; polycyclyl; where the aryl, heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and 1-$R^4$, wherein $R^4$ is

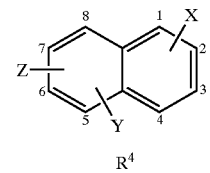

R⁴ where X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

B and D are independently selected from hydrogen, halogen, alkyl, haloalkyl, alkoxy, haloalkoxy, and alkoxyaminoalkyl;

R is —T—$(CH_2)_m$—$R^1$ or heterocyclyl, where
the heterocyclyl moiety may be optionally substituted with halogen, alkyl, haloalkyl, alkoxy, haloalkoxy, alkoxycarbonyl, aryl, arylcarbonyl, benzyl, allyl, propargyl;

T is selected from the group consisting of —$CH_2$—, oxygen, nitrogen, and sulfur;

m is 1, 2, 3, or 4;

$R^1$ is selected from the group consisting of —$N(R^8)(R^9)$; alkyl; aryl; —$C(O)N(R^{12})(R^{13})$; oxyalkyl;

haloalkyl; heterocyclyl; cycloalkyl; and —N(O)(R$^{14}$)(R$^{15}$), where the aryl and heterocyclyl moieties may be optionally substituted with halogen, alkyl, haloalkyl, alkoxy, haloalkoxy, alkoxycarbonyl, aryl, arylcarbonyl; where R$^8$, R$^9$, R$^{12}$, R$^{13}$, R$^{14}$ and R$^{15}$ are independently selected from the group consisting of hydrogen, alkyl, alkoxy, acetyl, alkoxycarbonyl, alkoxyalkyl, aminoalkyl, carbonylamino, and —(CH$_2$)$_p$—N(R$^{16}$)(R$^{17}$), where
p is 1 or 2;
R$^{16}$ and R$^{17}$ are independently selected from the group consisting of hydrogen, alkyl, alkoxy, alkoxyalkyl, and aminoalkyl;
and the corresponding agriculturally acceptable salts thereof.

6. A compound of claim 5 wherein
A is hydrogen or Formula III, where Formula III is

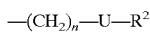   III wherein
n is 0 or 1;
U is selected from the group consisting of —CH$_2$—, oxygen, and —NR$^5$, where R$^5$ is selected from the group consisting of hydrogen, hydroxy, alkyl, sulfonylalkyl, cabonylamino, and carbonylalkyl;
R$^2$ is selected from alkylpolycyclyl; heterocyclyl; polycyclyl; where the heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and 1-R$^4$, wherein R$^4$ is

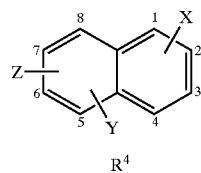

where X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;
B and D are independently selected from hydrogen, halogen, alkyl, haloalkyl, alkoxy, haloalkoxy, and alkoxyaminoalkyl;
R is —T—(CH$_2$)$_m$—R$^1$ or heterocyclyl, where
the heterocyclyl moiety may be optionally substituted with halogen, alkyl, haloalkyl, alkoxy, haloalkoxy, alkoxycarbonyl, aryl, arylcarbonyl, benzyl, allyl, propargyl;
T is selected from the group consisting of oxygen, nitrogen, and sulfur;
m is 1, 2, 3, or 4;
R$^1$ is selected from the group consisting of —N(R$^8$)(R$^9$); alkyl; aryl; —C(O)N(R$^{12}$)(R$^{13}$); oxyalkyl;

haloalkyl; heterocyclyl; cycloalkyl; and —N(O)(R$^{14}$)(R$^{15}$), where the aryl and heterocyclyl moieties may be optionally substituted with halogen, alkyl, haloalkyl, alkoxy, haloalkoxy, alkoxycarbonyl, aryl, arylcarbonyl; where R$^8$, R$^9$, R$^{12}$, R$^{13}$, R$^{14}$ and R$^{15}$ are independently selected from the group consisting of hydrogen, alkyl, alkoxy, acetyl, alkoxycarbonyl, alkoxyalkyl, aminoalkyl, carbonylamino, and —(CH$_2$)$_p$—N(R$^{16}$)(R$^{17}$), where
p is 1 or 2;
R$^{16}$ and R$^{17}$ are independently selected from the group consisting of hydrogen, alkyl, alkoxy, alkoxyalkyl, and aminoalkyl;
and the corresponding agriculturally acceptable salts thereof.

7. A compound of formula I:

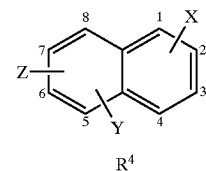

wherein:
A is Formula III, where Formula III is

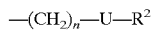   III wherein
n is 1;
U is oxygen or —NR$^5$, where R$^5$ is selected from the group consisting of hydrogen, hydroxy, alkyl, sulfonylalkyl, cabonylamino, and carbonylalkyl;
R$^2$ is 1-R$^4$, wherein R$^4$ is

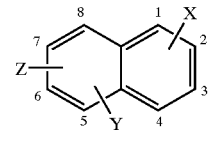

where X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;
B and D are independently selected from hydrogen, halogen, alkyl, haloalkyl, alkoxy, haloalkoxy, and alkoxyaminoalkyl;
R is —T—(CH$_2$)$_m$—R$^1$ or heterocyclyl, where
the heterocyclyl moiety may be optionally substituted with halogen, alkyl, haloalkyl, alkoxy, haloalkoxy, alkoxycarbonyl, aryl, arylcarbonyl, benzyl, allyl, propargyl;
T is oxygen or nitrogen;
m is 1, 2, 3, or 4;

$R^1$ is selected from the group consisting of —N($R^8$)($R^9$); alkyl; aryl; —C(O)N($R^{12}$)($R^{13}$); oxyalkyl; haloalkyl; heterocyclyl; cycloalkyl; and —N(O)($R^{14}$)($R^{15}$), where the aryl and heterocyclyl moieties may be optionally substituted with halogen, alkyl, haloalkyl, alkoxy, haloalkoxy, alkoxycarbonyl, aryl, arylcarbonyl; where $R^8$, $R^9$, $R^{12}$, $R^{13}$, $R^{14}$ and $R^{15}$ are independently selected from the group consisting of hydrogen, alkyl, alkoxy, acetyl, alkoxycarbonyl, alkoxyalkyl, aminoalkyl, carbonylamino, and —(CH$_2$)$_p$—N($R^{16}$)($R^{17}$), where p is 1 or 2;

$R^{16}$ and $R^{17}$ are independently selected from the group consisting of hydrogen, alkyl, alkoxy, alkoxyalkyl, and aminoalkyl;

and the corresponding agriculturally acceptable salts thereof.

8. A compound of claim 7 wherein

A is Formula III, where Formula III is

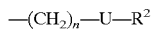 —(CH$_2$)$_n$—U—R$^2$    III wherein

U is oxygen or —NR$^5$, where R$^5$ is hydrogen;

R$^2$ is 1-R$^4$, wherein R$^4$ is

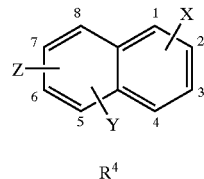

where X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

B and D are independently selected from hydrogen, halogen, alkyl, haloalkyl, alkoxy, haloalkoxy, and alkoxyaminoalkyl;

R is —T—(CH$_2$)$_m$—R$^1$ or heterocyclyl; where the heterocyclyl moiety may be optionally substituted with halogen, alkyl, haloalkyl, alkoxy, haloalkoxy, alkoxycarbonyl, aryl, arylcarbonyl, benzyl, allyl, propargyl;

T is oxygen or nitrogen;

m is 2;

R$^1$ is —N(R$^8$)(R$^9$) or —N(O)(R$^{14}$)(R$^{15}$), where R$^8$, R$^9$, R$^{14}$, and R$^{15}$ are independently selected from the group consisting of hydrogen, alkyl, alkoxy, acetyl, alkoxycarbonyl, alkoxyalkyl, aminoalkyl, carbonylamino, and —(CH$_2$)$_p$—N(R$^{16}$)(R$^{17}$), where p is 1 or 2;

R$^{16}$ and R$^{17}$ are independently selected from the group consisting of hydrogen, alkyl, alkoxy, alkoxyalkyl, and aminoalkyl;

and the corresponding agriculturally acceptable salts thereof.

9. A compound of claim 8 wherein

A is Formula III, where Formula III is

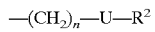 —(CH$_2$)$_n$—U—R$^2$    III wherein

U is O or —NR$^5$, where R$^5$ is hydrogen;

R$^2$ is selected from 1-R$^4$, wherein R$^4$ is

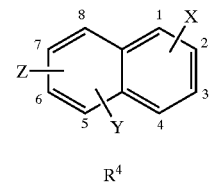

where X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

B and D are hydrogen;

R is —T—(CH$_2$)$_m$—R$^1$; where

T is oxygen;

R$^1$ is —N(R$^8$)(R$^9$) or —N(O)(R$^{14}$)(R$^{15}$), where R$^8$, R$^9$, R$^{14}$, and R$^{15}$ are independently selected from the group consisting of hydrogen, alkyl, alkoxy, acetyl, alkoxycarbonyl, alkoxyalkyl, aminoalkyl, and carbonylamino;

and the corresponding agriculturally acceptable salts thereof.

10. A compound of claim 9 wherein

A is Formula III, where Formula III is

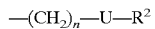 —(CH$_2$)$_n$—U—R$^2$    III wherein

U is O;

R$^2$ is selected from 1-R$^4$, wherein R$^4$ is

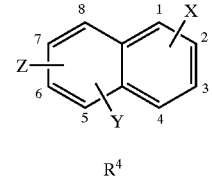

where X, Y, and Z are independently selected from the group consisting of hydrogen, halogen, cyano, nitro, amino, azido, carboxyl, alky, haloalkyl, nitrilyl, alkenyl, alkoxy, haloalkoxy, carbonyl, alkylcarbonyl, haloalkylcarbonyl, alkoxycarbonyl, haloalkoxycarbonyl, aryl, and aryloxy, where the aryl moieties may be optionally substituted with halogen, alkyl, haloalkyl, alkoxy, or haloalkoxy;

R$^1$ is —N(R$^8$)(R$^9$) or —N(O)(R$^{14}$)(R$^{15}$), where R$^8$, R$^9$, R$^{14}$ and R$^{15}$ are alkyl;

and the corresponding agriculturally acceptable salts thereof.

11. A compound of claim 10 wherein $R^1$ is —N($R^8$)($R^9$), X is 4-chloro or 5-chloro, Y is 6-chloro, Z is hydrogen, and $R^8$ and $R^9$ are ethyl.

12. A hydrochloride salt of the compound of claim 11.

13. A compound of claim 10 wherein $R^1$ is —N(O)($R^{14}$)($R^{15}$), X is 5-chloro, Y is 6-chloro, Z is hydrogen, and $R^{14}$ and $R^{15}$ are ethyl.

14. A compound of claim 8 wherein
A is Formula III, where Formula III is

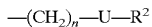  III wherein
U is O;
$R^2$ is selected from 1-$R^4$, wherein $R^4$ is

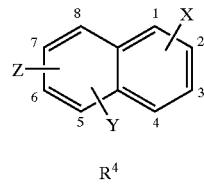

where X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;
B and D are hydrogen;
R is heterocyclyl; where
the heterocyclyl moiety may be optionally substituted with halogen, alkyl, haloalkyl, alkoxy, haloalkoxy, alkoxycarbonyl, aryl, arylcarbonyl, benzyl, allyl, propargyl;
and the corresponding agriculturally acceptable salts thereof.

15. A compound of claim 14 wherein
A is Formula III, where Formula III is

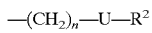  III wherein
$R^2$ is selected from 1-$R^4$, wherein $R^4$ is

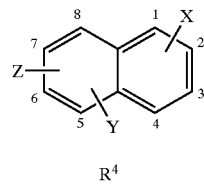

where X, Y, and Z are independently selected from the group consisting of hydrogen, halogen, cyano, nitro, amino, azido, carboxyl, alkyl, haloalkyl, nitrilyl, alkenyl, alkoxy, haloalkoxy, carbonyl, alkylcarbonyl, haloalkylcarbonyl, alkoxycarbonyl, haloalkoxycarbonyl, aryl, and aryloxy, where the aryl moieties may be optionally substituted with halogen, alkyl, haloalkyl, alkoxy, or haloalkoxy;
R is a piperazinyl moiety; where
the piperazinyl moiety may be optionally substituted with halogen, alkyl, haloalkyl, alkoxy, haloalkoxy, alkoxycarbonyl, aryl, arylcarbonyl, benzyl, allyl, propargyl;
and the corresponding agriculturally acceptable salts thereof.

16. A compound of claim 15 wherein the piperazinyl moiety is substituted with 4-ethyl; X is 5-chloro, Y is 6-chloro or 6-bromo, and Z is hydrogen.

17. A compound of formula I:

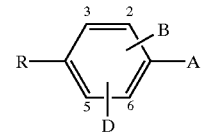  I wherein:
A is selected from the group consisting of aryl; alkylheterocyclyl; alkenylaminopolycyclyl; alkenylaminoheterocyclyl; alkylaminopolycyclyl; carbonylaminopolycyclyl; where the aryl, heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and Formula III, where Formula III is

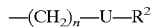  III wherein
n is 0 or 1;
U is selected from the group consisting of —CH$_2$—, —O—CH$_2$—, oxygen, sulfur, sulfonyl, alkyl, oxyalkyloxy, alkenylamino, cabonylamino and —NR$^5$, where R$^5$ is selected from the group consisting of hydrogen, hydroxy, alkyl, haloalkyl, sulfonylalkyl, cabonylamino, and carbonylalkyl;
$R^2$ is selected from aryl; alkylpolycyclyl; heterocyclyl; polycyclyl; where the aryl, heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; 1-$R^4$; and 2-$R^4$, wherein:
$R^4$ is

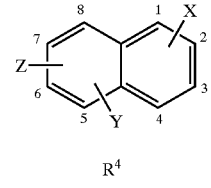

where X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, aryloxy, and heterocyclyl, where the phenyl, aryl, and heterocyclyl moieties may be optionally substituted with halogen, haloalkyl, haloalkyl, alkoxy, or haloalkoxy;

with the proviso that X, Y and Z cannot all be hydrogen;

B and D are independently selected from hydrogen, halogen, alkyl, haloalkyl, alkoxy, haloalkoxy, alkoxyaminoalkyl, 2-(Formula III), 3-(Formula III), 5-(Formula III), and 6-(Formula III), wherein Formula III, n, U, $R^2$, $R^4$, $R^5$, X, Y, and Z are as defined above;

R is —T—$(CH_2)_m$—$R^1$, —$N(R^6)(R^7)$ or heterocyclyl, where
the heterocyclyl moiety may be optionally substituted with halogen, hydroxy, alkyl, haloalkyl, alkoxy, haloalkoxy, alkoxycarbonyl, aryl, alkylaza, arylcarbonyl, benzyl, allyl, propargyl, alkylamino; where the aryl moiety may be optionally substituted with halogen, hydroxy, alkyl, haloalkyl, alkoxy, haloalkoxy, alkoxycarbonyl, aryl, arylcarbonyl;
T is selected from the group consisting of —$CH_2$—, carbonyl, oxygen, nitrogen, and sulfur;
m is 0, 1, 2, 3, or 4;
$R^1$ is selected from the group consisting of —$N(R^8)(R^9)$; aryl; —$C(O)N(R^{12})(R^{13})$; oxyalkyl; haloalkyl; heterocyclyl; cycloalkyl; —$N(O)(R^{14})(R^{15})$; —$P(O)(R^{14})(R^{15})$; —$P(S)(R^{14})(R^{15})$; alkylamino, where the cycloalkyl, aryl and heterocyclyl moieties may be optionally substituted with halogen, hydroxy, alkyl, haloalkyl, alkoxy, haloalkoxy, alkoxycarbonyl, aryl, arylcarbonyl, alkylamino; where
$R^6$, $R^7$, $R^8$, $R^9$, $R^{12}$, $R^{13}$, $R^{14}$ and $R^{15}$ are independently selected from the group consisting of hydrogen, alkyl, alkoxy, alkylthio, acetyl, alkoxycarbonyl, alkoxyalkyl, aminoalkyl, carbonylamino, and —$(CH_2)_p$—$N(R^{16})(R^{17})$, where
p is 1 or 2;
$R^{16}$ and $R^{17}$ are independently selected from the group consisting of hydrogen, alkyl, alkoxy, alkoxyalkyl, and aminoalkyl;

and the corresponding agriculturally acceptable salts thereof.

18. A compound of claim 17 wherein

A is selected from the group consisting of alkylaminopolycyclyl; and carbonylaminopolycyclyl; where the polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxy[]arbonyl, haloalkoxycarbonyl, or aryl; and Formula III, where Formula III is

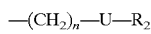  III wherein
n is 0 or 1;
U is selected from the group consisting of —$CH_2$—, oxygen, alkyl, oxyalkyloxy, alkenylamino, cabonylamino and —$NR^5$, where $R^5$ is selected from the group consisting of hydrogen, hydroxy, alkyl, sulfonylalkyl, cabonylamino, and carbonylalkyl;
$R^2$ is selected from aryl; alkylpolycyclyl; heterocyclyl; polycyclyl; where the aryl, heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and 1-$R^4$, wherein $R^4$ is

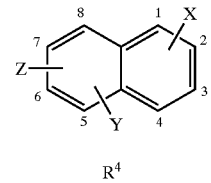

where X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkylcarbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

B and D are independently selected from hydrogen, halogen, alkyl, haloalkyl, alkoxy, haloalkoxy, and alkoxyaminoalkyl;

R is —T—$(CH_2)_m$—$R^1$ or heterocyclyl, where
the heterocyclyl moiety may be optionally substituted with halogen, alkyl, haloalkyl, alkoxy, haloalkoxy, alkoxycarbonyl, aryl, arylcarbonyl, benzyl, allyl, propargyl;
T is selected from the group consisting of —$CH_2$—, oxygen, nitrogen, and sulfur;
m is 1, 2, 3, or 4;
$R^1$ is selected from the group consisting of —$N(R^8)(R^9)$; alkyl; aryl; —$C(O)N(R^{12})(R^{13})$; oxyalkyl; haloalkyl; heterocyclyl; cycloalkyl; and —$N(O)(R^{14})(R^{15})$, where the aryl and heterocyclyl moieties may be optionally substituted with halogen, alkyl, haloalkyl, alkoxy, haloalkoxy, alkoxycarbonyl, aryl, arylcarbonyl; where
$R^8$, $R^9$, $R^{12}$, $R^{13}$, $R^{14}$ and $R^{15}$ are independently selected from the group consisting of hydrogen, alkyl, alkoxy, acetyl, alkoxycarbonyl, alkoxyalkyl, aminoalkyl, carbonylamino, and —$(CH_2)_p$—$N(R^{16})(R^{17})$, where
p is 1 or 2;
$R^{16}$ and $R^{17}$ are independently selected from the group consisting of hydrogen, alkyl, alkoxy, alkoxyalkyl, and aminoalkyl;
and the corresponding agriculturally acceptable salts thereof.

19. A compound of claim 18 wherein

A is Formula III, where Formula III is

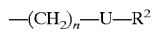  III wherein
n is 0 or 1;
U is selected from the group consisting of —$CH_2$—, oxygen, and —$NR^5$, where $R^5$ is selected from the group consisting of hydrogen, hydroxy, alkyl, sulfonylalkyl, cabonylamino, and carbonylalkyl;
$R^2$ is selected from alkylpolycyclyl; heterocyclyl; polycyclyl; where the heterocyclyl and polycyclyl moieties are optionally substituted with one or more of the following: halogen, cyano, nitro, amino, carboxyl, alkyl, haloalkyl, alkoxy, haloalkoxy, carbonyl, alkylcarbonyl, haloalkylcarbonyl, alkoxycarbonyl, haloalkoxycarbonyl, or aryl; and 1-R⁴, wherein R⁴ is

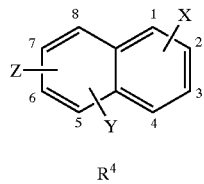

where X, Y, and Z are independently selected from the group consisting of hydrogen, halogen, cyano, nitro, amino, azido, carboxyl, alkyl, alkynyl, haloalkyl, haloalkylthio, nitrilyl, alkenyl, alkoxy, haloalkoxy, carbonyl, alkylcarbonyl, haloalkyl-carbonyl, alkoxycarbonyl, haloalkoxycarbonyl, phenyl, aryl, and aryloxy, where the phenyl and aryl moieties may be optionally substituted with halogen, haloalkyl, haloalkyl, alkoxy, or haloalkoxy;

B and D are independently selected from hydrogen, halogen, alkyl, haloalkyl, alkoxy, haloalkoxy, and alkoxyaminoalkyl;

R is —T—(CH$_2$)$_m$—R$^1$ or heterocyclyl, where the heterocyclyl moiety may be optionally substituted with halogen, alkyl, haloalkyl, alkoxy, haloalkoxy, alkoxycarbonyl, aryl, arylcarbonyl, benzyl, allyl, propargyl;

T is selected from the group consisting of oxygen, nitrogen, and sulfur;

m is 1, 2, 3, or 4;

R$^1$ is selected from the group consisting of —N(R$^8$)(R$^9$); alkyl; aryl; —C(O)N(R$^{12}$)(R$^{13}$); oxyalkyl; haloalkyl; heterocyclyl; cycloalkyl; and —N(O)(R$^{14}$)(R$^{15}$), where the aryl and heterocyclyl moieties may be optionally substituted with halogen, alkyl, haloalkyl, alkoxy, haloalkoxy, alkoxycarbonyl, aryl, arylcarbonyl; where R$^8$, R$^9$, R$^{12}$, R$^{13}$, R$^{14}$ and R$^{15}$ are independently selected from the group consisting of hydrogen, alkyl, alkoxy, acetyl, alkoxycarbonyl, alkoxyalkyl, aminoalkyl, carbonylamino, and —(CH$_2$)$_p$—N(R$^{16}$)(R$^{17}$), where p is 1 or 2;

R$^{16}$ and R$^{17}$ are independently selected from the group consisting of hydrogen, alkyl, alkoxy, alkoxyalkyl, and aminoalkyl;

and the corresponding agriculturally acceptable salts thereof.

* * * * *